US008329393B2

(12) United States Patent
Miller et al.

(10) Patent No.: US 8,329,393 B2
(45) Date of Patent: *Dec. 11, 2012

(54) METHOD FOR DETECTING AND REMOVING ENDOTOXIN

(75) Inventors: Stefan Miller, Regensburg (DE);
Roman Meyer, Schmidmuhlen (DE);
Renate Grassl, Regensburg (DE);
Manfred Biebl, Regensburg (DE);
Holger Grallert, Regensburg (DE)

(73) Assignee: Hyglos Invest GmbH, Bernried (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/181,199

(22) Filed: Jul. 12, 2011

(65) Prior Publication Data
US 2011/0306068 A1 Dec. 15, 2011

Related U.S. Application Data

(62) Division of application No. 11/814,358, filed as application No. PCT/DE2006/000098 on Jan. 23, 2006, now Pat. No. 8,003,313.

(30) Foreign Application Priority Data

Jan. 21, 2005 (DE) .......................... 10 2005 002 969

(51) Int. Cl.
C12Q 1/70 (2006.01)
G01N 33/53 (2006.01)
C07K 14/005 (2006.01)
C07K 17/00 (2006.01)

(52) U.S. Cl. .................. 435/5; 435/7.1; 530/350
(58) Field of Classification Search .................. None
See application file for complete search history.

(56) References Cited

U.S. PATENT DOCUMENTS

| 5,179,018 | A | 1/1993 | Bogard, Jr. et al. | 530/388.15 |
| 5,506,121 | A | 4/1996 | Skerra et al. | 435/69.7 |
| 5,510,242 | A | 4/1996 | Blais et al. | 435/7.32 |
| 5,627,266 | A | 5/1997 | Wainwright et al. | 530/350 |
| 5,747,455 | A | 5/1998 | Wainwright et al. | 514/12 |
| 5,760,177 | A | 6/1998 | Iwanaga et al. | 530/350 |
| 5,917,022 | A | 6/1999 | Davies | 530/390.1 |
| 5,990,301 | A | 11/1999 | Colpan et al. | 536/25.4 |
| 6,365,147 | B1 | 4/2002 | Luo et al. | 424/93.1 |
| 6,376,462 | B1 | 4/2002 | Gazzano-Santoro et al. | 514/12 |
| 6,384,188 | B1 | 5/2002 | Hoess et al. | 530/326 |
| 6,942,802 | B2 | 9/2005 | Sundberg et al. | 210/635 |
| 7,585,620 | B2 | 9/2009 | Schulz et al. | 435/5 |
| 2002/0130082 | A1 | 9/2002 | Todokoro et al. | 210/660 |
| 2002/0147315 | A1 | 10/2002 | Pyo et al. | 530/416 |
| 2004/0248298 | A1 | 12/2004 | Schutz et al. | 435/383 |

FOREIGN PATENT DOCUMENTS

| DE | 10129815 | 1/2003 |
| DE | 10228133 | 1/2004 |
| DE | 10307793 | 9/2004 |
| EP | 0074240 | 3/1983 |
| EP | 0232754 | 7/1992 |
| EP | 0592989 | 4/1994 |
| GB | 2192633 | 1/1988 |
| WO | WO 94/14837 | 7/1994 |
| WO | WO 95/05393 | 2/1995 |
| WO | WO 95/08560 | 3/1995 |
| WO | WO 95/25117 | 9/1995 |
| WO | WO 99/15676 | 4/1999 |
| WO | WO 00/08463 | 2/2000 |
| WO | WO 01/27289 | 4/2001 |
| WO | WO 01/66718 | 9/2001 |
| WO | WO 02/083710 | 10/2002 |
| WO | WO 04/001418 | 12/2003 |

OTHER PUBLICATIONS

Database EMBL, "Gp12 short tail fiber," Database accession No. AAQ17871, Jul. 2003.
Galanos and Luderitz, "Electrodialysis of lipopolysaccharides and their conversion to uniform salt forms," Eur. J. Biochem. , 54:603-610, 1975.
Hancock and Reeves, "Bacteriophage resistance in Escherichia coli K-12: general pattern of resistance," J. Bacteriol. , 121:983-993, 1975.
Hantke, "Major outer membrane proteins of E. coli K12 serve as receptors for the phages T2 (protein Ia) and 434 (protein Ib)," Mol .Gen Genet. , 164:131-135, 1978.
Leiman et al., "Structure and morphogenesis of bacteriophage T4m" Cell Mol. Life Sci., 60:2356-2370, 2003.
Merino et al., "Identification of the cell surface receptor for bacteriophage 18 from Aeromonas hydrophila," Research in Microbiology, 141:173-180, 1990.
NCBI Databank, Databank Accession No. AAQ17871, dated Jul. 11, 2003.
NCBI Databank, Databank Accession No. AY266303, dated Jul. 11, 2003.
Office Communication, issued in U.S. Appl. No. 11/814,358, dated Jun. 1, 2010.
Office Communication, issued in U.S. Appl. No. 11/814,358, dated Sep. 14, 2010.
Office Communication, issued in U.S. Appl. No. 11/814,358, dated Mar. 3, 2011.
Petsch and Anspach, "Endotoxin removal from protein solutions," J. Biotechnol., 76:97-119, 2000.
Riede et al., "DNA sequence heterogeneity in the genes of T-even type Escherichia coli phages encoding the receptor recognizing protein of the long tail fibers," Mol. Gen. Genet., 195:144-152, 1984.

(Continued)

Primary Examiner — Zachariah Lucas
Assistant Examiner — Nicole Kinsey White
(74) Attorney, Agent, or Firm — Parker Highlander PLLC

(57) ABSTRACT

The present invention relates to bacteriophage tail proteins and the derivatives and fragments thereof that are capable of binding endotoxins in the absence of bivalent positive ions, especially $Ca^{2+}$ or $Mg^{2+}$. Further, the present invention relates to methods for depleting endotoxins from solutions and samples using the bacteriophage tail proteins according to the present invention and to a detection method for endotoxins.

22 Claims, 17 Drawing Sheets

OTHER PUBLICATIONS

Figure 2:
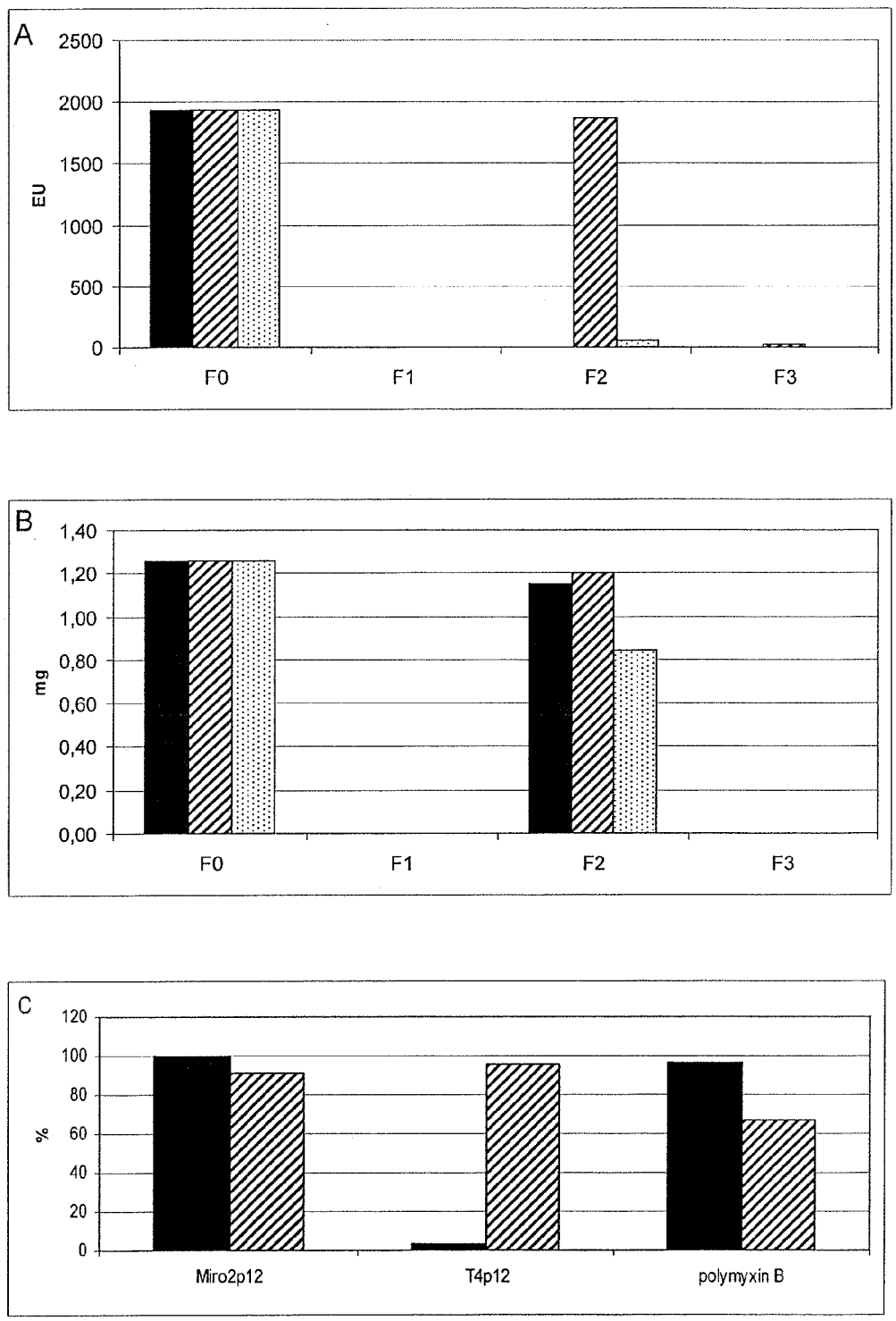

Seckler, "Folding and function of repetitive structure in the homotrimeric phage P22 tailspike protein," *J. Struct. Biol.*, 122:216-222, 1998.

Triantafilou et al., "Lipopolysaccharide (LPS) labeled with Alexa 488 hydrazide as a novel probe for LPS binding studies," *Cytometry*, 41:316-320, 2000.

Troelstra et al., "Dual effects of soluble CD14 on LPS priming of neutrophils," *J. Leukoc. Biol.*, 61:173-178, 1997.

Fig. 1
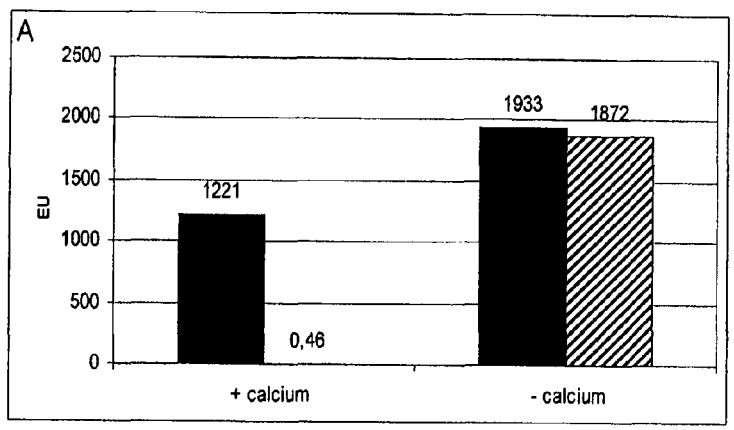
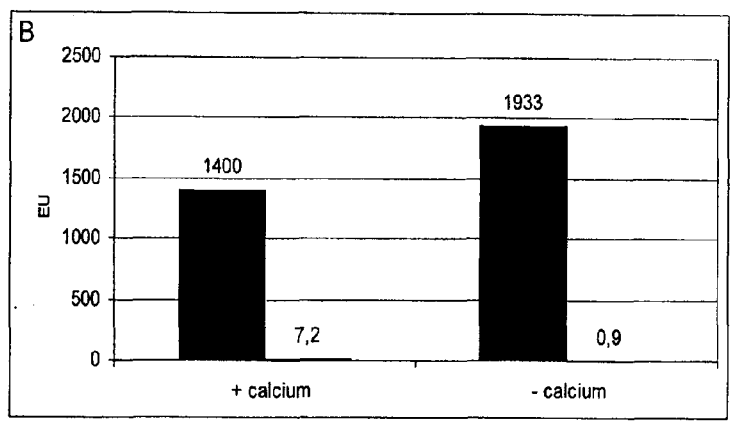
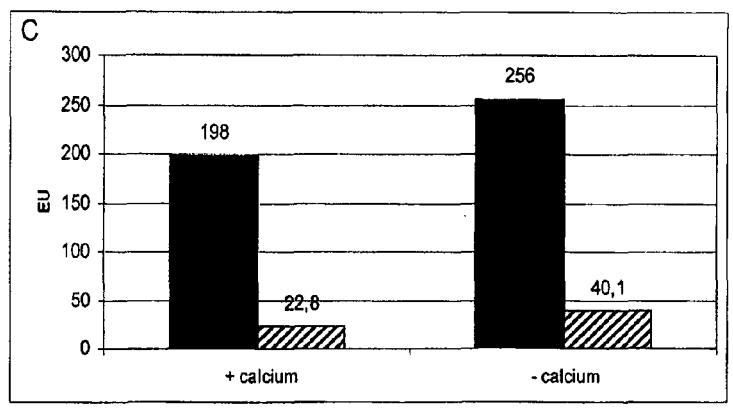

Fig. 4
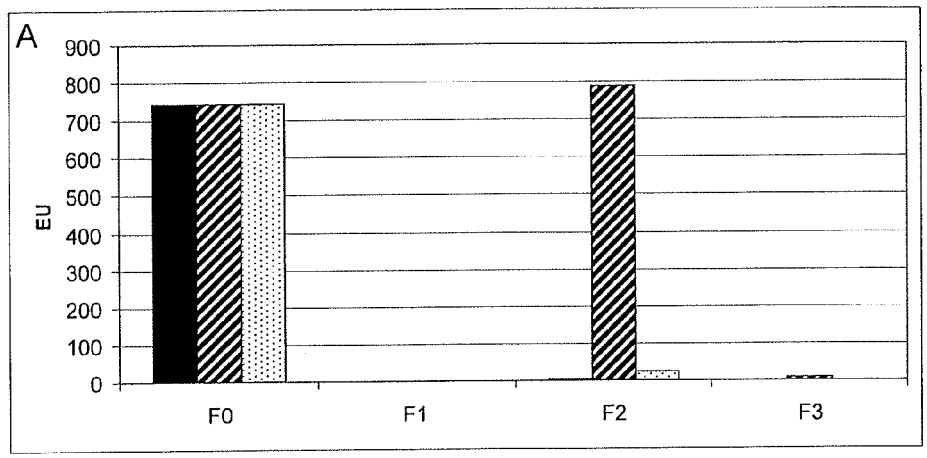
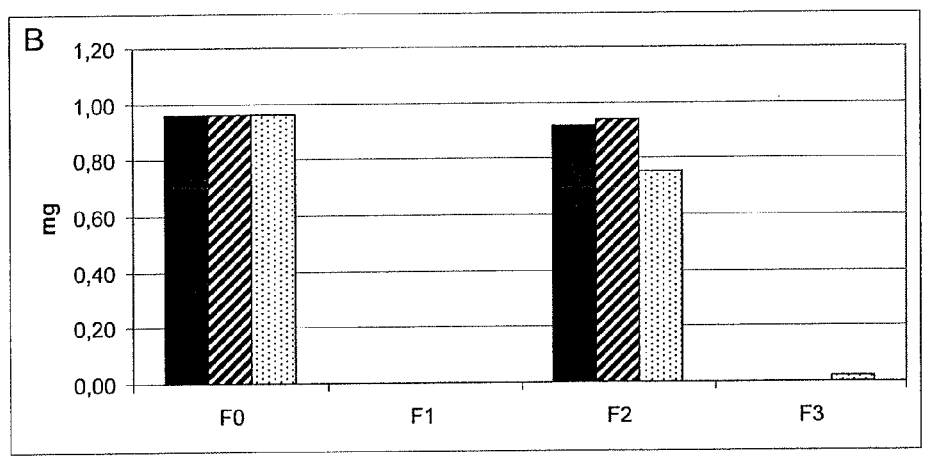
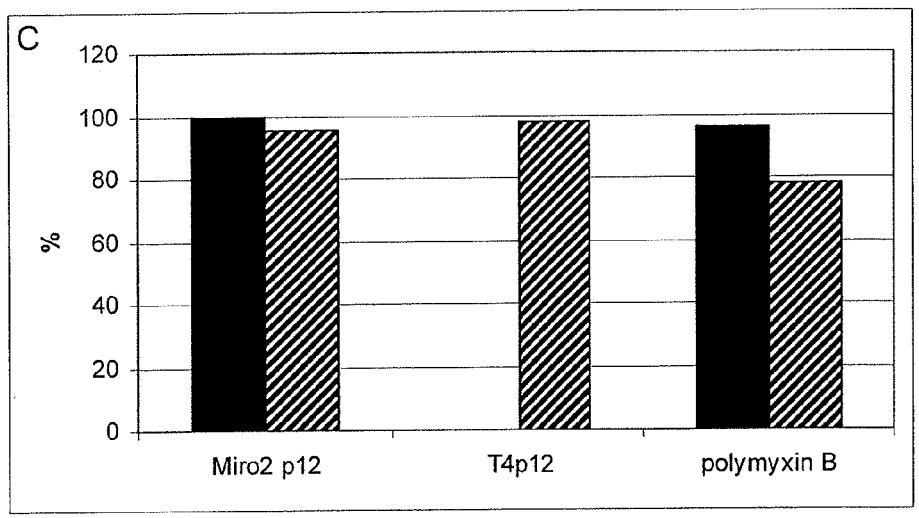

FIG.11 A

```
K3p12           --------------MSNNTYQHVSNESRYVKFDPTDTNFPPEI---TDVQAAIAAISPAG
T2p12           --------------MSNNTYQHVSNESRYVKFDPTDTNFPPEI---TDVQAAIAAISPAG
T4p12           --------------MSNNTYQHVSNESRYVKFDPTDTNFPPEI---TDVHAAIAAISPAG
RB32-33         --------------MSNNTYQHVSNESKYVKFDPVGSNFPDTV---TTVQSALSKISNIG
AR1p12          --------------MSNNTYQHVSNESKYVKFDPTGSNFPDTV---TTVQSALSKISNIG
PP01p12         --------------MSNNTYQHVSNESKYVKFDPVGSNFPDTV---TTVQSALSKISNIG
RB69            --------------MSNNTYQHVSNESVYVEFDPTGSNFDSSI---TNVQAALASISAYG
Eff04_p12       MASASWSHPQFEKGASNNTINHVSDKSIYVTFDPTGTDWPDTI---TNVQDALEKIGSWA
RB43p12         --------------MSNNTINHVSDASVYVTFDPAGTQWPSTF---VNVQQALASIGPWA
RB49p12         --------------MANNTINHVKDDAQYVKFNPVN-DWPQSI---TNVQAALAAINGFA
Miro1p12        ----MLEPPAVEKGAAQNNYNHYSDLAKYTIFDPTNTQWPVAI---KDVQSALELIGSWA
Miro2p12        --MASWSHPQFEKGAAQNNYNHYSDLAKYTIFDPTNTQWPVAI---KDVQSALELIGSWA
44RR2           --------------MVANNIKNHISDSAESVNY--TGDNWPAIV---TTVADALDRVAPWA
PHG31p12        --------------MVANNIKNHISDSAESVNY--TGDTWPAIV---TTVADALDRVAPWA
AehIp12         ------------MRTNNITQHISSKAGSVVFDPASAPAFDTT---ITDLQKLGNKIDAHA
KVP40p12        ------------MSKGTQIFNHVIDDAGTVTVEVAGTAFDGQTGGNDDLQTCLELIQDHA
                              :   :*   .  :   .     ..          :     :   .

K3p12           VN--GVP---DASSTTKGILFLATEQEVIDGTNNTKAVTPATLATRLS-YPNATETVYGL
T2p12           VN--GVP---DASSTTKGILFLATEQEVIDGTNNTKAVTPATLATRLS-YPNATEAVYGL
T4p12           VN--GVP---DASSTTKGILFIPTEQEVIDGTNNTKAVTPATLATRLS-YPNATETVYGL
RB32-33         VN--GIP---DATMEVKGIAMIASEQEVLDGTNNSKIVTPATLATRLL-YPNATETKYGL
AR1p12          VN--GIP---DATMEVKGIAMIASEQEVLDGTNNSKIVTPATLATRLL-YPNATETKYGL
PP01p12         VN--GIP---DASMEVKGIAMIASEQEVLDGTNNSKIVTPATLATRLL-YPNATETKYGL
RB69            VK--GVP---DASEAEKGVIQLATEQEVLDGFNSTKAVTPATLNARLQ-YPNASETQYGV
Eff04_p12       RTDTGLP---IATTSVRGIAQIATEADINAGTDNTKIVTPKLLAYRMQ-NPKASQTVWGY
RB43p12         RTDVGLP---NAAPGMRGIAAIATEAMIDAGTDNETIVTPALLAYRLQ-NPHASQTVWGY
RB49p12         VN--GLP---DATEDTAGIAAIATQEEVNDGTVDNKIVTPKTLAVKMS-RPDATKEVKGI
Miro1p12        RTDTGLP---VASPTVAGVIRTATQAEVDAGTIGNAAVTPATLKSTVT-RPEATTAVLGL
Miro2p12        RTDTGLP---VASPTVAGVIRTATQAEVDAGTIGNAAVTPATLKSTVT-RPEATTAVLGL
44RR2           IIDNGLP---LATTQIAGIIRIATTAEMQAGTSANTAITPALLKLAME-TPQASETIVGN
PHG31p12        IIDNGLP---LATTQIAGIIRIATTAEMQAGTSANTAITPALLKLAME-TPQASETIVGN
AehIp12         TK--PLP---VASETVSGIAELATVDEVLLGNDKVRLVTPYTLQQKWA-RPNASDTVYGL
KVP40p12        VQ--PLPDYPVASTTVAGITKLSDEAAVVDPLNTDSAVTPSSLDYWMQNHATATELQYGF
                    :*    *:     *:    .    :     :**  *      . *:    *
```

FIG.11 B

```
K3p12      --ADDTTAMTPLKTQQLAIKLIAQIAPSETTATESDQGVVQLATVAQVRQGTLREG-YAI
T2p12      --ADDTTAMTPLKTQQLAVKLIAQIAPSKNAATESEQGVIQLATVAQARQGTLREG-YAI
T4p12      --ADDTTAMTPLKTQQLAIKLIAQIAPSETTATESDQGVVQLATVAQVRQGTLREG-YAI
RB32-33    --VDDTTAMTPLKTQKLAIKLISQIAPSEDTASESVRGVVQLSTVAQTRQGTLREG-YAI
AR1p12     --VDDTTAMTPLKTQKLAIKLISQIAPSEDTASESVRGVVQLSTVAQTRQGTLREG-YAI
PP01p12    --VDDTTAMTPLKTQKLAIKLISQIAPSEDTASESVRGVVQLSTVAQTRQGTLREG-YAI
RB69       --SDDTTAMTPLKTQQLAIKLISQIAPNNDPASESITGVVRLATVAQTRQGTLREG-YAI
Eff04_p12  --TDNTVTMTPLKVKQAIASLVP----VQSSATESSQGLVQLATVAQVQAGTIREG-YAI
RB43p12    --TDDTSMTPLKVKQAISALVP----VQSNATESAFGLVQLATVSEVRAGTIRDG-FAI
RB49p12    --SDDTMAVTPKKMHTAIAQIVPGLIPDQNTATESAQGLVQLATNAQVLQGQIREG-FAI
Miro1p12   --TDETTAVTPKRVVEMIGKFSVS-PPSYTSATESNLGLVRVATQAQVAAGAVHDG-YAV
Miro2p12   --TDETTAVTPKRVVEMIGKFSVS-PPSYTSATESNLGLVRVATQAQVAAGAVHDG-YAV
44RR2      --TDDATTMTPLKTKLAIQALSQ----AWGTATESARGVVQMATVAQALQGTLRDG-FAI
PHG31p12   --TDDATTMTPLKTKLAIQALSQ----AWGTATESARGVVQMATVAQALQGTLRDG-FAI
AehIp12    --VDDTTAMTPAKVKAAIDTFAVT---SVSGATETVTGTVKNSPALITNAALHTG--YAV
KVP40p12   GTLSTTVAMTPQRVKEMLDVWANT---TASDASETTKGLIRLANGTEVNSTLATEDNLAI
                .:  ::**  :             *:*:   * ::  :    .          *:

K3p12      SPYTFMNSSATEEYKGVIKLGTQSEVNSNN-ASVAVTGATLNGRGSTTSMRGVVRLTTTA
T2p12      SPYTFMNSTATEEYKGVIKLGTQSEVNSNN-ASVAVTGATLNGRGSTTSMRGVVKLTTTA
T4p12      SPYTFMNSSSTEEYKGVIKLGTQSEVNSNN-ASVAVTGATLNGRGSTTSMRGVVKLTTTA
RB32-33    SPYTFMNSVATQEYKGVIRLGTQSEINSNL-GDVAVTGETLNGRGATSSMRGVVKLTTQA
AR1p12     SPYTFMNSVATQEYKGVIRLGTQSEINSNL-GDVAVTGGTLNGRGATGSMRGVVKLTTQA
PP01p12    SPYTFMNSVATQEYKGVIRLGTQSEINSNL-GDVAVTGETLNGRGATGSMRGVVKLTTQA
RB69       SPYTFMNSVATQEYKGVIRLGTQAEINSNL-GDVAVTGETLNGRGATGSMRGVVKLTTQA
Eff04_p12  SPYTFIRLTATESNLGVIRIASQTEANAGTDDTKAITAKKLINTRATGSQFGVVKLATTV
RB43p12    SPYTFIRLNATESDLGIVRLASQAEVNAGTDDTKAVTPLKLANLKGSGGSFGLVKLSTEV
RB49p12    SPYAFANARANENQAGTVKIASQSQMNAGSDDTVVVSAKKFASTKATTSQYGIVKLRDTV
Miro1p12   TPKTFMASKASDSVFGIVKFAKDSDVASATSNNLAVTPKSLQALKSTKDKYGLTRLSGSP
Miro2p12   TPKTFMASKASDSVFGIVKFAKDSDVASATSNNLAVTPKSLQALKSTKDKYGLTRLSGSP
44RR2      SPYTLSKMAGTESAAGMFKIASNSQILALADNTVVVTPAKLDILKATASQLGLVKLSGVS
PHG31p12   SPYTLSKMAGTESAAGMFKIASNSQILALADNTVVVTPAKLDILKATASQLGLVKLSGVS
AehIp12    TPKGFIETRAAQARVGTVRMATQAEANARTLGDVAISPATLPIASD--TQYGITALLHNA
KVP40p12   SPYRFNFRTATTTRKAGFYLPDATVANARASNEHAVTVGTLNLFSANSSRVGVAKIANNL
           :*    :    .   . . :  :    :      .::   .:         *:. :

K3p12      GSQSGGDASSALAWNADVIHQRGGQTINGTLRINNTLTIASGGANITGTVNMTGGYIQGK
T2p12      GSQSGGDASSALAWNADVIHQRGGQTINGTLRINNTLTIASGGANITGTVNMTGGYIQGK
T4p12      GSQSGGDASSALAWNADVIQQRGGQIIYGTLRIEDTFTIANGGANITGTVRMTGGYIQGN
RB32-33    GIAPEGDGSGALAWNADVINTRGGQTINGSLNLD---HLTANGIWSRGGMWKNG----DQ
AR1p12     GIAPEGDSSGALAWNADVINTRGGQTINGSLNLD---HLTANGIWSRGGMWKNG----DQ
PP01p12    GIAPEGDSSGALAWNADVINTRGGQTINGSLNLD---HLTANGIWSRGGMWKNG----DQ
RB69       GVAPEGDSSGALAWNADVINTRGGQTINGSLNLD---HLTANGIWSRGGMWKNG----DQ
Eff04_p12  GY----VANTALSSNAYVLPSDR-------------SAVINGSLYEYSAIHNN-----K
RB43p12    NAG---LANTALSAGANVVPSNRD------------SAITGGALYQGSVAAAN-----K
RB49p12    GS----EANAALSANAKVLPSTG-------------GTVSGNVYKGSNSDGN-----Q
Miro1p12   TT----DASLAAAATDAVFKTRK-------------INGKTLDNDITITNNDINCYTR
Miro2p12   TT----DASLAAAATDAVFKTRR-------------INGKTLDNDITITNNDINCYTR
44RR2      TA----AANTALAASAPVLYTSGG------------IITGDVTFTGNMQGIQWSRNTD
PHG31p12   TA----AANTALAASAPVLYTSGG------------IITGDVTFTGNMQGIQWSRNTD
AehIp12    QSG---VTNKALSAHGATLFINR-----------NGDSMTGDLTVHNIFTANGQNGRGD
KVP40p12   TTN---DPLQALSAAMGYKLNNEK-------IGDAGGTVTGTLKINNVQSVGGTQLMTN
                                                  *  :
```

FIG.11 C

```
K3p12        RVVTQNEIDRTIPVGAIMMWAADSLPSDAWRFCHGGTVSASDCPLYASRIGTRYGGSSSN
T2p12        RVVTQNEIDRTIPVGAIMMWAADSLPSDAWRFCHGGTVSASDCPLYASRIGTRYGGTSSN
T4p12        RIVTQNEIDRTIPVGAIMMWAADSLPSDAWRFCHGGTVSASDCPLYASRIGTRYGGNPSN
RB32-33      PVATERYASERVPVGTIMMFAGDSAP-PGWIMCHGGTVSGDQYPDYRNTVGARFGGDWNN
AR1p12       PVATERYASERVPVGTIMMFAGDSAP-PGWIMCHGGTVSGDQYPDYRNTRFGGDWNN
PP01p12      PVATERYASERVPVGTIMMFAGDSAP-PGWIMCHGGTVSGDQYPDYRNTVGTRFGGDWNN
RB69         PVATERYASERVPVGTIQMFAGDSAP-PGWVLCHGGTISGDQFPDYRNVVGTRFGGDWNN
Eff04_p12    YQTWTDLDWH-FPVGAIVMTGFQTDH-GSLYICDGRSLNKNNYPLLFERIGYTFGGGGDW
RB43p12      YQTHSDIEAS-LPIGCMMMAAFNSDY-GNLCIANGRGMYTYEYPELFALIGYTYGGSGNI
RB49p12      FVTKNELANHAMPIGGIILSGFNADR-GDFLICNGRSLNKNQYPQLFSAIGYTFGGSGDN
Miro1p12     QESDGRYMPAGTRVGNVTWVEGQSWISRGATFTCNAPWEASSRLALNVNVKFERNNDGYD
Miro2p12     QESDGRYMPAGTRVGNVTWVEGQSWISRGATFTCNAPWEASSRLALNVNVKFKRNNDGYD
44RR2        MAHIVFKNDSNADSNSFMQFCVGDDNNEYFRWVN--RFSGSDN----IMATLRPGGHMWL
PHG31p12     MAHIVFKNDSNADSNSFMQFCVGDDNNEYFRWVN--RFSGSDN----IMATLRPGGHMWL
AehIp12      SLTRKDYVDGLFNQ-KANISHTHGTPQESWTLIWQGPLDRGNF----VTNQPWWNFDALV
KVP40p12     GLIESQAMLNMYPVGSVYMSLVSTSPATLFGGTWARLAQGRVL----VSEGSYGGRTFAV K3p12        PGLPDMRGLFVRGSGRGSHLTNPNVNGNDQFGKPRLGVGCTGGYVGEVQKQQMSYHKHAG
T2p12        PGLPDMRGLFVRGSGRGSHLTNPNVNGNDQFGKPRLGVGCTGGYVGEVQKQQMSYHKHAG
T4p12        PGLPDMRGLFVRGSGRGSHLTNPNVNGNDQFGKPRLGVGCTGGYVGEVQIQQMSYHKHAG
RB32-33      PGIPDMRGLFVRGAGTGGHILNQ--RGQDGYGKDRLGVGCDGMHVGGVQAQQMSYHKHAG
AR1p12       PGIPDMRGLFVRGAGTGGHILNQ--RGQDGYGKDRLGVGCDGMHVGGVQAQQMSYHKHAG
PP01p12      PGIPDMRGLFVRGAGTGXHILNQ--RGQDGYGKDRLGVGCDGMHVGGVQAQQTSYHKHAG
RB69         PGIPDMRGLFVRGAGTGSHILNN--RGQDGYGKDRLGVGCDGMHVGGVQAQQMSYHKHAG
Eff04_p12    FNIPDCRGVAVRGHDRGRGLNPN--RGYGTYEGDMLG-------WHEHPLQLIYQ--NGG
RB43p12      FNLPDMRGVVARGFDAGRGLDPG--RGFGTYQHHEVQ-------SHEHPLQMIYQ--SGG
RB49p12      FNLPDMRGLVARGCDHGRNLDPG--RRFGSYQEDAMQR-----ITGKFPVADRWRGWYGG
Miro1p12     NRIFRFV-VIVNGSQWGGELTLN--------------------IENTKGGRNGHSW
Miro2p12     NRIFRFV-VIVNGSQWGGELTLN--------------------IENTKGGRNGHSW
44RR2        AGNIDVNDFYIRSDRRLKHGFKPIENALDKIDLLNPG--------TYHKQYSLTDDRIV
PHG31p12     AGNIDVNDFYIRSDRRLKHGFKPIENALDKIDLLNPG--------TYHKQYSLTDDRIV
AehIp12      IESSRDGGSWFNTMEISRWQIEQ-------------------------MQAKYPN---
KVP40p12     RQTGGEYEVQLTEATIPAHKHAG-------------------------WGEHYDGNGI K3p12        GFGEW---DDSGAFGNTRRSNFVGTRKGLDWDNRSYFTNDGYEIDPASQRNSRYTLNRPE
T2p12        GFGEY---DDSGAFGNTRRSNFVGTRKGLDWDNRSYFTNDGYEIDPASQRNSRYTLNRPE
T4p12        GFGEH---DDLGAFGNTRRSNFVGTRKGLDWDNRSYFTNDGYEIDPESQRNSKYTLNRPE
RB32-33      GWGEY--QRHEAPFGASVYQGYLGTRKYSDWDNASYFTNDGFELG--GPRDALGTLNREG
AR1p12       GWGEY--NRSEGPFGASVYQGYLGTRKYSDWDNASYFTNDGFELG--GPRDALGTLNREG
PP01p12      AWGENGNNRGYAPFGASNGSGYLGNGRSADWDNHLFFTNDGFEMG--GPRDSFGTLNREG
RB69         GWGEF--QRHEAPFGASVYQGYLGTRKYSDWDNASYFTNDGFELG--GHRDATGTLNREG
Eff04_p12    NIPKW---------QAVYELKSAEKNDQSARVFDASITKATGVG-------------
RB43p12      NLPSW---------QCVYELRTAEKNDQQLYWPDPSLSKAMAVG-------------
RB49p12      AFTAQ---------RGQWSTNYKNGGGDDWGTTVNFDSGRSVRT-------------
Miro1p12     RFEAY----------ASSNFFFNNIPPNATVQIRPTEDS-----------
Miro2p12     RFEAY----------ASSNFFFNNIPPNATVQIRPTEDS-----------
44RR2        GLEAG----------IFAQDFQKAMPEGVRSLEDGTLTVSPMG-----------AIA
PHG31p12     GLEAG----------IFAQDFQKAMPEGVRSLEDGTLTVSPMG-----------AIA
AehIp12      -FNLVS----------AQEYYWFGKFRADG---MYFDT-------------
KVP40p12     GFGVAK----------QYGRNNPGSRRTDSDNYLYYTSPVGGNQ-----------
```

FIG.11 D

```
K3p12       LIGNETRPWNISLNYIIKVKE
T2p12       LIGNETRPWNISLNYIIKVKE
T4p12       LIGNETRPWNISLNYIIKVKE
RB32-33     LIGYETRPWNISLNYIIKIHY
AR1p12      LIGYETRPWNISLNYIIKIHY
PP01p12     LIGYETRPWNISLNYIIKIHY
RB69        LIGYETRPWNISLNYIIKVHY
Eff04_p12   --GEETRMKNIALNYVIRVL-
RB43p12     --GNETRMKNLAINYVIRVR-
RB49p12     --ANETRVKSLALNYIIRVR-
Miro1p12    ----RIIFYDCMLTFCTNRP-
Miro2p12    ----RIIFYDCMLTFCTNRP-
44RR2       FLIQCNKELKARLEKLEGIK-
PHG31p12    FLIQCNKELKARLEKLEGIK-
AehIp12     ---HTENCYLWRIYGVNKTWS
KVP40p12    --AHNNVQPYYTVYMWERTA-
                               :
```

METHOD FOR DETECTING AND REMOVING ENDOTOXIN

This application is a divisional application of U.S. Ser. No. 11/814,358, filed Jul. 19, 2007, now U.S. Pat. 8,003,313, which is a national phase application under 35 U.S.C. §371 of International Application No. PCT/DE 2006/000098 filed Jan. 23, 2006, which claims priority to German Patent Application No.: DE 10 2005 002 969.8 filed Jan. 21, 2005. The entire text of each of the above-referenced disclosures is specifically incorporated herein by reference without disclaimer.

The present invention relates to bacteriophage tail proteins and the derivatives and fragments thereof that are capable of binding endotoxins in the absence of bivalent positive ions, especially $Ca^{2+}$ or $Mg^{2+}$. Further, the present invention relates to methods for depleting endotoxins from solutions and samples using the bacteriophage tail proteins according to the present invention and to a detection method for endotoxins.

Bacteriophages recognize structures (membrane proteins, sugar molecules etc.) on the surface of theirs host bacteria by corresponding proteins, which bacteriophages have on theirs surface. Some bacteriophages have only one type of recognition protein, e.g. *salmonella* phage P22, others at least two or more. The recognition proteins may have enzymatic activity, as phage P22 (Seckler, J. Struct. Biol. 1998; 122(1-2):216-222), or may not have enzymatic activity. Enzymatic activity means, that these proteins, e.g. the P22 tail spike protein, are able to hydrolyze the receptor molecule, that they recognize, i.e. at p22 the *salmonella* O-antigen. The most known bacteriophage having two recognition proteins is for *E. coli* the specific phage T4. This phage has long and short tail fibers. The long tail fibers conduces the specific recognition of its host *E. coli* by the membrane protein OmpC or by lipopolysaccharide for *E. coli* B. While the long tail fibers of the phages T4, T2 and K3 bind specifically to OmpC and lipopolysaccaride of *E. coli* B (T4), respectively, OmpF (T2; Hantke K., Mol Gen Genet. 1978; 164 (2):131-135) and OmpA (K3; Hancock R E, Reeves P., J. Bacteriol. 1975; 121(3):983-993; Riede I, Eschbach M L, Henning U., Mol Gen Genet. 1984; 195(1-2):144-152), the short tail fibers are located at the bottom side of the phage and are not involved in the host specificity, but replaceable between T4, T2 and K3 phages (Riede, Mol Gen Genet. 1987; 206(1):110-115). Only after the binding of at least three long tail fibers, the short tail fibers are folded out of the basis plate and are responsible for irreversible binding of the T4 phage to the *E. coli* hosts (Leiman et al., Cell Mol Life Sci. 2003; 60(11):2356-2370). These short tail fiber proteins bind, as shown for page T4 (WO2004/001418), in the core region of the lipopolysaccharide and thus are qualified for recognizing and binding endotoxin.

Endotoxins (ET) describe a family of lipopolysaccharides, which form the outer cell membrane of gram-negative bacteria together with proteins and phospholipids. Endotoxins only occur in this bacteria group and play an important role at the organization, stability and barrier function of the outer membrane. Numerous bacteriophages use endotoxin and general lipopolysaccharides, respectively, for specific recognition of theirs host bacteria.

Endotoxins are biomolecules which may be found in practically all aqueous solutions without corresponding precautionary measures. Endotoxins effect on human and animals highly pyrogenically, so they cause fever response and are able to result in a sepsis, a heavy dysfunction of the immune system involving a high mortality rate. Therefore contamination with endotoxin, e.g. at the production of proteins for medical or pharmaceutical use, have to be detected exactly and be removed consequently. Endotoxin presents a problem by genetically produced pharmaceuticals, gentherapeutic agents or substances, which are injected into humans or animals (e.g. veterinary treatment or in animal tests). However, not only for medical, but also for research applications, such as transfection experiments of mammalian cells, an inhibition or decrease, respectively, of the transfection efficiency by endotoxin may be found.

All endotoxin variations consist of a heteropolysaccharide, that is covalent bound to lipid A (Holst, O., 1999, In: Endotoxin in health and disease (Brade, H. et al; eds.), Marcel Dekker Inc. New York)). Lipid A anchors endotoxin in the outer bacteria membrane. The heteropolysaccharide, consisting of a core oligosaccharide and the O-antigen, points to the ambient solution and determines the serological identity of the bacterium. The O-antigen consists of repetitive oligosaccharide units, whose composition is specific for each strain (see Holst et al., supra). Characteristic blocks of the core oligosaccharide are 2-keto-3-deoxyoctonic acid (KDO) and L-glycero-D-manno-heptose (Hep).

The most conservative part of different genera of endotoxin is the Lipid A. The inner heart region is related conserved as lipid A, while the outer core region already has a higher variation. The inner heart region, KDO and lipid A carry several phosphate groups as substitutes themselves and are consequently responsible for the negative charge of endotoxin. Furthermore, the phosphate groups of Lipid A and the core region may be substituted with arabinose, ethanolamine and phosphate variably. Single saccharide building blocks of the O-antigen are acetylated, sialylated or glycolysated. The O-antigen varies moreover concerning the amount of repetitive units, wherefore the endotoxin population of each bacterium has a certain heterogeneity (Palva E. T. and Makela P. H., Eur J. Biochem. 1980; 107(1): 137-43; Goldman R. C. and Leive L., Eur J. Biochem. 1980; 107(1):145-53).

To be able to use proteins within clinical studies, the European and American pharmacopoeia demand, that the proteins under-run certain limit values of endotoxin load (e.g. immune serum globulin$\leq$0.91 EU/ml, this corresponds to $\leq$5 EU/kg body weight & hour (dose rate=EU/kg*h); EU=endotoxin unit; FDA (Food and Drug Administration): Guideline on Validation of LAL as End Product). In case a drug and therein-containing proteins, respectively, have a too high endotoxin load, it is possible that this induces the death of the patient. The misdirected immune defense damages the patient by an over-reaction. This may induce tissue inflammation, decrease in blood pressure, tachycardia, thrombosis culminating in septic shock and multiple organ failure. Already a long running exposition of endotoxin in picogram quantities may induce chronic side effects e.g. low immunity, septic symptoms etc. Within the substance production, it is tried to deplete and remove, respectively, endotoxin as far as possible, in particular in processes of "Good Manufacturing Practice" (GMP) conditions. However, the removal of endotoxin on proteins, polysaccharides and DNA is problematically. In particular, great problems exist on proteins, because of whose intrinsic properties as charge state or hydrophobicity, which almost inhibit endotoxin removal and may lead to great losses of products, respectively, during the removal process.

Furthermore, the endotoxin detection as well as the removal is affected by the environment, since factors e.g. ion composition, pH-value, temperature or the presence of other substances may influence the interaction of a ligand with endotoxin rigorously. Thereby it must be considered, that the interaction of ligands may be carried out with different structure parts of the endotoxins as the hydrophobic Lipid A or the hydrophilic polysaccharide part. According to this, normally these interactions depend on ionic or hydrophobic forces, which are affected differently by the composition of the solution. The polysaccharide structure of endotoxins is stabilized by bivalent positive ions as calcium or magnesium (Galanos C. and Luderitz O., Eur. J. Biochem. 1975; 54:603-610). These ions are also able to interfere with ligands ("bridging-effect").

In general, there are a number of methods for depleting and removing endotoxin, respectively, from biological solutions. However particularly for proteins, there are no general applicable standard methods so far. The used methods are adapted to the special properties of the protein and its corresponding production process in each case. There are different opportunities for depleting endotoxins, wherein each of these methods has specific advantages and disadvantages.

The ultra filtration (Petsch, D. & Anspach, F. B., 2000, J. Biotechnol. 76, 97-119 and references therein) is used for depleting endotoxin from water and solutions with low-molecular substances as salts, sugar and antibiotics. However, it is not qualified for high-molecular proteins or DNA.

The two-phase extraction (e.g. WO 01/66718, Merck) should separate water-soluble proteins and DNA from endotoxin, but it involved detergent residues in the purified product. However, the method is time-consuming because of repeating the purification process for several times.

Likewise, an anion exchanger process (DEAE) (e.g. U.S. Pat. No. 5,990,301, Qiagen; WO 94/14837, Enzon; EP0592989, Braun Melsungen) is used for depleting endotoxins from DNA and acidic proteins, but it requires a low ionic strength (<50 mM NaCl) and leads to a protein co-adsorption of acidic proteins. For alkaline proteins cation-exchanger are used, which partly are combined with detergents (e.g. US 2002/0147315 A1).

Cationic peptides are used for removing endotoxin in EP 0232754 B1 (Commonwealth Biotechnologies).

In addition, hydrophilic matrices are used as a combination of dextran and N',N'-methylenebisacrylamide (U.S. Pat. No. 5,917,022).

Hydrophobic chromatography methods are used in WO94/14837 (Enzon).

The affinity adsorption (e.g. polymyxin B, histamine, histidine, poly-L-lysine, polyethylenimine) e.g. GB 2,192,633 (Hammersmith Hospital), US2002/0130082 A1 (Tokodoro), U.S. Pat. No. 5,510,242 or WO95/025117 (GMBF) is a further method for depleting endotoxins from DNA and proteins (e.g. BSA, myoglobin, gamma globulin, cytochrome C), but it is toxic in the case of polymyxin B and may lead to a co-adsorption of proteins at low ionic strength.

Following methods describe a removal of endotoxin by means of metal affinity chromatography (U.S. Pat. Nos. 6,365,147; 6,942,802; WO02/083710, American Cyanide).

In addition, LPS-binding proteins or peptides or derivates thereof are used for specific binding of endotoxin (U.S. Pat. No. 6,376,462, Xoma Corp.; U.S. Pat. No. 6,384,188, Dana Faber Cancer Institute; WO95/005393, Morphosys; WO95/008560, Centocor; WO95/025117, Scripps).

Further on, the immune-affinity chromatography is used, wherein the specificity for certain endotoxins can only be achieved by expensive antibodies against core oligosaccharide (U.S. Pat. No. 5,179,018, Centocor; WO 00/08463, Bioserv; EP0074240, Gaffin).

Further, the S3 delta peptide (WO 01/27289) of the factor C (a component of the LAL-test) (WO 99/15676 both: National University of Singapore) is used for proteins (e.g. BSA, chymotrypsinogene), however this method has a low efficiency at high ionic strength and high production costs come along (production of insect cell cultures).

Furthermore the endotoxin neutralizing protein (ENP) from *Limulus polyphemus*, that also binds specifically to endotoxin (e.g. U.S. Pat. No. 5,747,455; U.S. Pat. No. 5,627,266) or the LPS binding protein of the horseshoe crab (U.S. Pat. No. 5,760,177) is used for depleting endotoxins. The recovery of this protein from the horseshoe crab or recombinant from *saccharomyces* is also time-consuming and cost-intensive.

A further method for removing endotoxins from a sample is described in the WO2004/001418. Thereby endotoxins are bound to a carrier immobilized with bacteriophage tail proteins and are so separated from the sample. For an efficient separation, bivalent ions are necessary by what the method cannot be carried out with industrial relevant buffers e.g. phosphate or citrate buffers or in the presence of chelators as EDTA or EGTA.

Essentially three methods exist for protein solutions adapted to the properties of the target proteins in application in pharmaceutical industry:

anion exchange chromatography reserved-phase chromatography; This has the disadvantage, that it is not suitable for all proteins similarly and for hydrophobic proteins particularly problematically. Furthermore, this method is very time-intensive and proteins are normally denaturated under the conditions of the reserved-phase chromatography, so that they have to be renaturated afterwards time-consuming and often with a high material loss RemTox (Fa. Milipore): This method has the disadvantage that beside a very long incubation time the unspecific binding fraction is high and the recovery of proteins is often not sufficiently.

A rough depletion of endotoxin from proteins to a value of up to 10 EU/ml is possible in numerous cases with the existing methods. However, still the remaining concentrations of endotoxin affect toxically. Therefore, a further depletion (i.e. precision purification) is demanded and dependent, respectively, on the protein doses in the medical application. The European pharmacopoeia, the USP (United States Pharmacopeial Convention) and the FDA (Food and Drug Administration) specify the limit values for medical application bindingly (e.g. 5 EU/kg body weight and hour for intravenous applications). However, the precision purification is often not warranted sufficiently with the present methods. The standard methods have relevant disadvantages and are often not applicable for certain proteins or only with a relevant loss of the target protein.

Further, in view of industrial applications it have to be considered, that only buffer substances as phosphate, citrate, borate, carbonate or acetate as cheap as possible are used for reasons of economy. Therefore, the interaction of ligands with endotoxins should not be interfered by these buffers. For binding reactions needing calcium, in particular buffers or additives are problematically, which coordinate calcium as EDTA, EGTA or citrate. In addition, buffers whose salts build insoluble or hardly soluble precipitations with calcium are problematically. For example, calcium phosphate precipitates so there is only a low concentration of free calcium in phosphate buffers.

Beside of depleting and removing endotoxin, respectively, the endotoxin detection in samples, solutions and pharmaceutical preparation plays an important role. Currently six detection methods are described for endotoxin in biologic solutions, wherein only the first two methods are accredited from the FDA. The EAA (endotoxin activity assay) is accredited from the TPD (Therapeutic Product Directorate of Canada) and from the FDA under certain conditions (high risk for sepsis at intensive patients) also. 1. "Rabbit Pyrogen Testing": A method in which an endotoxin solution is injected to a living rabbit to cause an immune reaction. This immune response caused by endotoxin is verified by fever. 2. Clearly better to standardize is the "Limulus Amoebocyte Lysate (LAL)"—test, which is currently the most applied test (Cambrex-BioWhittacker, Inc., Charles River, Inc., Associates of Cape Cod, Inc., all USA). For this method, an enzyme cascade is induced in the blood of the horseshoe crab (*Limulus polyphemus*) after the contact of endotoxin. The existence of endotoxin can be measured by four different methods (gel-clot, turbidimetric, colorimetric and chromogenic assay). 3. The InVitro Pyrogene test based on the detection of interleukine-1β in human blood, which is involved in the induction of fever. The test consists of an incubation step of human blood with the examining solution and the following detection of interleukins by antibodies. 4. A similar method is the detection of the induction of prostaglandine (PGE2) in rabbit blood after the contact with endotoxin (Ochiai et al., Microbiol. Immunol., 2003, 47, 585-590). 5. A further possibility is the application of a special cell culture systems (Sterogene Inc., USA) with which the activation of monocytes is pursued by the formation of certain cytokins 6. The EAA (endotoxin activity assay) by the company Spectral Diagnostics, Inc., Canada is also a blood test. Endotoxin reacts with antibodies, wherein the signal is enforced and detected as chemiluminescence after the complement activation in the patient owned neutrophiles by means of a zymosans.

However, the both first named methods are very expensive and not at least critical for nature conservation reasons because of the high demand of test animals and blood of the very rare horseshoe crab, respectively. In fact, the LAL-test is able to be miniaturized and automated but it has massive disadvantages at the application. It is labor-intensive, requires special trained staff, relative long incubation times, relative big sample volumes and expensive reagents. A onetime opened LAL-solution has to be processed and used up directly, because the components aggregate within a few hours because of low stability. Bivalent ions have to be present in the application of the test, the pH-value is relatively limited (pH 6-7.5) and present glucans often interfere the test. Endotoxin is often masked, i.e. it is e.g. not recognized, if it is bound to proteins. The InVitro Pyrogen test requires as fresh human blood as possible and is relative time-intensive, because the production of the interleukins requires 10 to 24 hours. The main advantage of this method is that also other pyrogens are detected beside endotoxins. This test is primarily intended for replacement of the "Rabbit Pyrogen test". For all test methods, trained stuff is required and the methods are sensitive for interference, because e.g. it is possible that the immune system of rabbits reacts differently at the same dose of endotoxin. The cell culture method of the company Sterogene is also, as all cell culture methods, very complex and has problems with the standardization. If the different methods for detecting endotoxin are compared, the results often differ from each other, i.e. different endotoxins are not recognized by different test components in the same way. Altogether, it can be fixed, that no easy manageable economic method exists for detecting endotoxin and that the currently used methods have numerous disadvantages.

Therefore, the object of this invention is to provide instruments and methods for removing and detecting endotoxins out and in solutions independent of the content of bivalent positive ions.

The problem of the invention is solved by the subject matter of the claims.

The following figures illustrate the invention.

FIG. 1 shows the result of the endotoxin removal by T4p12-sepharose (A), N-Strep-Miro2p12-sepharose (B) and N-Strep-Aeh1p12-sepharose (C) from "calcium containing" (with calcium) and "calcium free" (without calcium) buffers. The black bars show respectively the applied endotoxin amount and the dashed bars the endotoxin amount after the run of the solution by the corresponding sepharose. The endotoxin amounts were measured by the LAL-test (kinetic-chromogenic LAL-test, Cambrex) and are specified in endotoxin units (EU). At first, the bacteriophage tail proteins were immobilized on NHS-activated sepharose (Amersham Biosciences) and afterwards chromatography columns were cast with these coupled sepharose material. Columns were cast with volumes of 1 ml (T4p12, N-Strep-miro2p12) and 200 µl (N-Strep-Aeh1p12). As column bodies 1 ml polypropylene columns (Qiagen) and Handee Mini Spin Columns (200 µl, Pierce) were used. At first, the columns were equibrilated with running buffer (6-times column volume); the sample was applied and afterwards washed with 3-times column volume. The endotoxin amounts in the application (black bars) and in the flow-through (dashed bars) are represented respectively side by side. The tests were carried out in "calcium containing" and "calcium free" buffer. The "calcium containing" buffer consisted of 20 mM Hepes, 150 mM NaCl, 0.1 mM $CaCl_2$, pH 7.5 and the "calcium free" buffer consisted of 20 mM Hepes, 150 mM NaCl, 2 mM EDTA, pH 7.5. With T4p12 sepharose it was only possible to remove endotoxin with the "calcium containing" buffer from the solution, while calcium had no influence of the endotoxin removal with N-Strep-Miro2p12 and N-Strep-Aeh1p12 sepharose.

FIG. 2 A-C shows the result of the endotoxin removal from a BSA solution by chromatography columns with immobilized Miro2p12 in comparison to columns of polymyxin and T4p12. The running buffer (20 mM Hepes, 150 mM NaCl, 2 mM EDTA, pH 7.5) contained 2 mM EDTA and therefore only a low concentration of free calcium (<1 µM; Donald Bers, Chris Patton, Richard Nuccitelli, Methods in Cell Biology, Vol. 40; A practical guide to the study of Ca in living cells; chapter 1: A practical guide to the preparation of Ca Buffers, Academic Press, 1/94). The chromatography columns contained each 2 ml column material. Before the application of the sample (F0), 1 ml flow-through of running buffer was collected (F1). Afterwards, each 1 ml of a BSA-solution (1.2 mg/ml), studded with approximately 2000 EU/ml, was applied onto each column and two further fractions were collected with 4 ml and 3 ml (F2 and F3). In FIG. 2(A) the amounts of endotoxin and in FIG. 2(B) the amounts of BSA in the application and in the fractions F1-F3 are represented of the polymyxin B-column (spotted bars), the T4p12 column (dashed bars) and the Miro2p12 column (filled bars). In FIG. 2(C) the percental endotoxin removal (filled bars) and the protein recovery (dashed bars) is shown calculated for the second fraction. By T4p12 it was not possible to remove endotoxin under these buffer conditions, while it was possible to remove 96% of endotoxin by the polymyxin B column and 99.6% by the Miro2p12 column. The protein recovery was 67% for polymyxin B and 92% for Miro2p12. The percental endotoxin removal shows how much endotoxin, available at the beginning of the experiment, was removed by the treatment with Miro2p12 or other proteins. The protein recovery informs how much of the applied protein is still in the sample after the endotoxin removal and is unspecifically removed, respectively, by the endotoxin removal.

Figure 3:
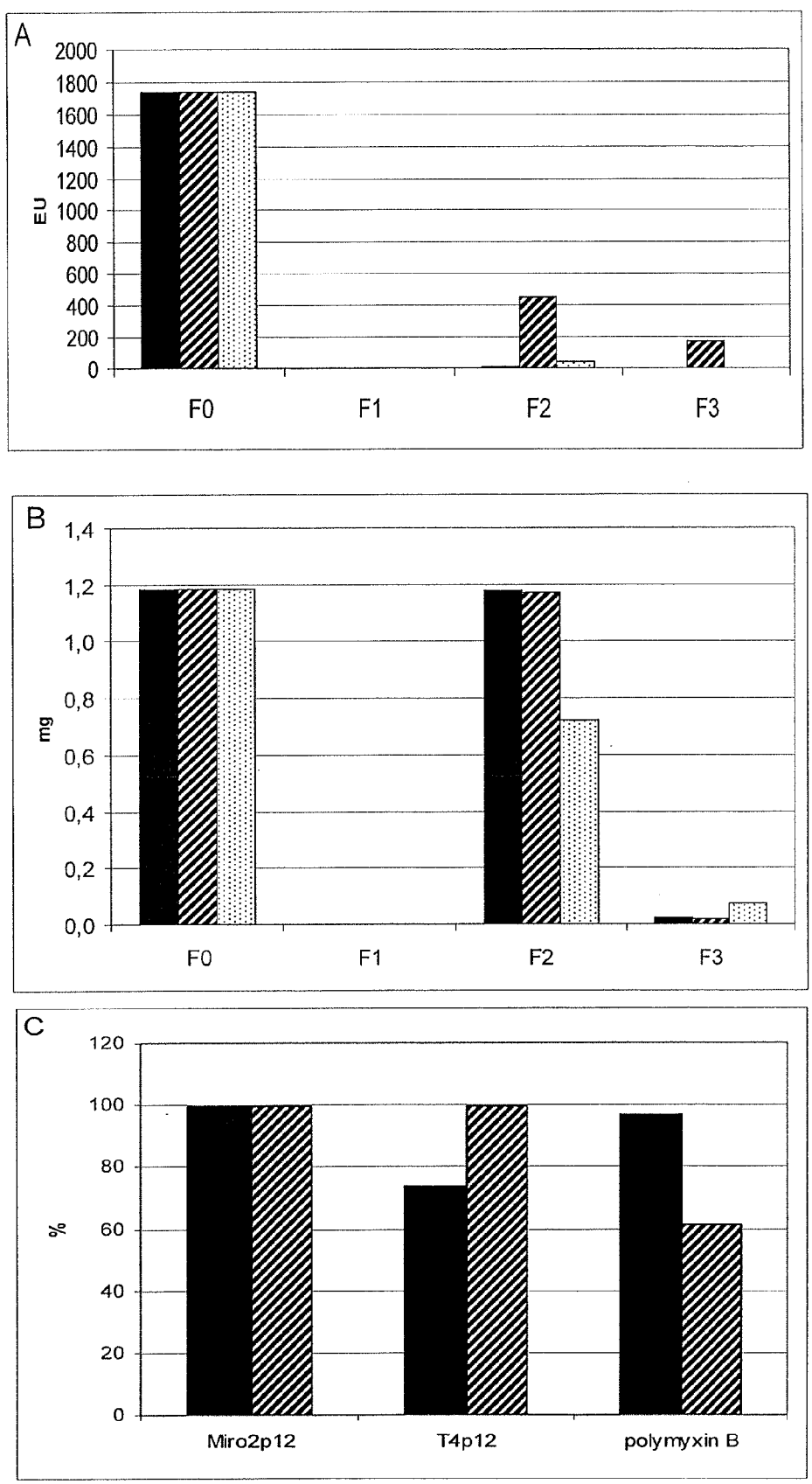

FIG. 3 A-C shows the result of the endotoxin removal from a BSA solution by chromatography columns immobilized with Miro2p12 in comparison to columns of polymyxin B and T4p12. As running buffer the physiologic important PBS buffer (10 mM $Na_2HPO_4$, 1.8 mM $KH_2PO_4$, 137 mM NaCl, 2.7 mM KCl, pH 7.4) was used in this experiment. The chromatography columns contained each 2 ml column material. Before the application of the sample (Fraction F0), 1 ml flow-through of the running buffer was collected (F1). Afterwards each 1 ml of a BSA solution (1.2 mg/ml), studded with approximately 1800 EU/ml, was applied onto each column and two further fractions were collected with 4 ml and 3 ml (F2 and F3). In FIG. 3(A) the endotoxin amounts and in FIG. 3(B) the BSA amounts in the application and in the fractions F1-F3 are represented of the polymyxin B-column (spotted bars), the T4p12 column (dashed bars) and the Miro2p12 column (filled bars). In FIG. 3(C) the percental endotoxin removal (filled bars) and the protein recovery (dashed bars) is shown calculated for the second fraction. By polymyxin B it was possible to remove 97% of endotoxin, by T4p12 74% and by Miro2p12 99.7%. The protein recovery was 61% for polymyxin B, 99.4% for T4p12 and 99.8% for Miro2p12.

FIG. 4 A-C shows the result of the endotoxin removal from a BSA solution by chromatography columns immobilized with Miro2p12 in comparison to columns with polymyxin B and T4p12. A citrate buffer (20 mM citrate, 150 mM NaCl, pH 7.0) was used, which is able to bind calcium ions. The chromatography columns contained each 1.5 ml column material. Before the application of the sample (Fraction F0), 1 ml flow-through of the running buffer was collected (F1). Afterwards each 1 ml of a BSA solution (0.96 mg/ml), studded with approximately 750 EU/ml, was applied onto each column and two further fractions were collected with 4 ml and 3 ml (F2 and F3). In FIG. 4(A) the endotoxin amounts and in FIG. 4(B) the BSA amounts in the application and in the fractions F1-F3 are represented of the polymyxin B-column (spotted bars), the T4p12 column (dashed bars) and the Miro2p12 column (filled bars). In FIG. 4(C) the percental endotoxin removal (filled bars) and the protein recovery (dashed bars) is shown calculated for the second fraction. By polymyxin B it was possible to remove 96.2% of endotoxin, by T4p12 0% and by Miro2p12 99.5%. The protein recovery was 78.3% for polymyxin B, 97.8% for T4p12 and 95.4% for Miro2p12.

Figure 5:
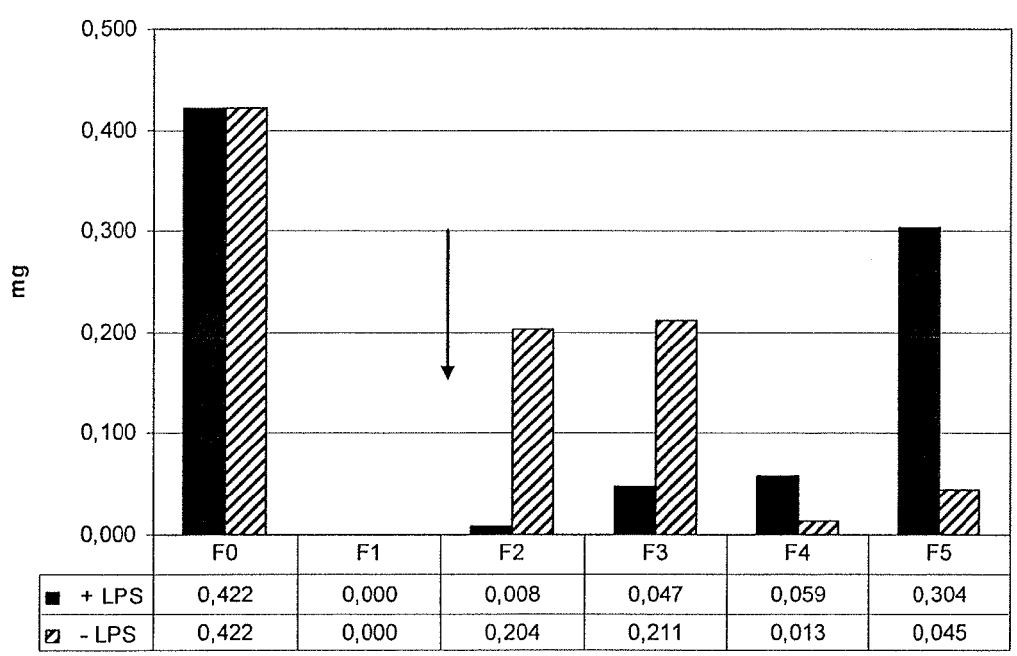

FIG. 5 shows the result of the endotoxin detection by the binding of T4p12 to immobilized endotoxin (Miro2p12-endotoxin-T4p12 sandwich). The bacteriophage tail protein Miro2p12 was covalent immobilized (3.4 mg protein/ml column material) to the column material (0.5 ml). A sample, containing endotoxin of E. coli O55:B5 ($10^6$ EU/ml), was applied onto the column and bound by Miro2p12 (+LPS, black bars). A control column was equilibrated with the sample without endotoxin (−LPS, dashed bars). The amount of the bacteriophage tail protein p12 was plotted against the fractions of the chromatography run. Each bar shows the averages detected in two parallel chromatography runs. The first bar pair (F0) shows the applied amount of T4p12 and the second the fraction 1 (F1), a control fraction before the application of T4p12 onto the column. The arrow marks the application of p12 onto the column. The fractions F2-F5 were collected after the application. The amount of p12 (stated in mg) was detected by absorption measurement at 280 nm. The fraction volume was 1 ml for fractions F1-F4 and 2 ml for fraction F5. The dissolution of bound T4p12 protein in fraction F5 was affected by addition of 2 mM EDTA to the running buffer (20 mM Hepes, 150 mM NaCl, 0.1 mM $CaCl_2$, pH 7.5). The bacteriophage tail protein T4p12 was retained at the columns prior loaded with endotoxin, while it elutes without delay through the columns containing no endotoxin.

Figure 6:
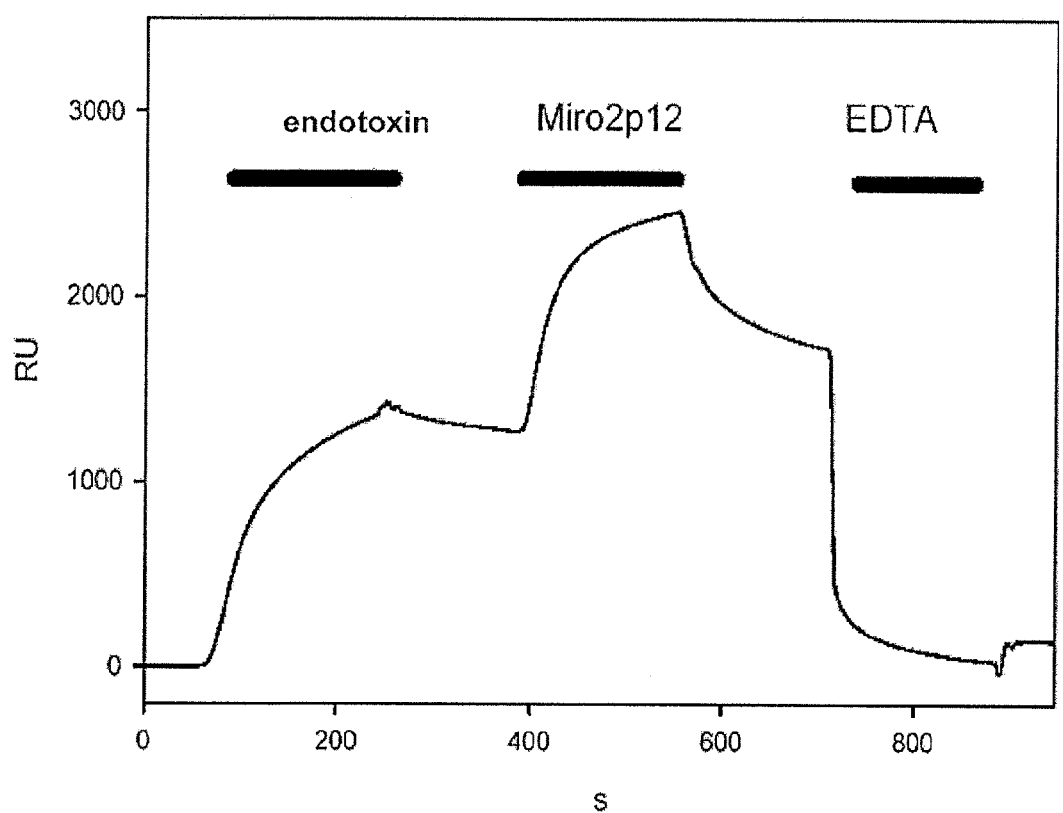

FIG. 6 shows the result of the binding of Miro2p12 by endotoxin arranged to T4p12. A CM-5 chip of company Biacore was used with covalent immobilized T4p12 (EDC/NHS-coupling). At first, endotoxin (of E. coli O55:B5; 1 mg/ml) was injected, which binds to T4p12 as shown by the increase of the resonance signal. Afterwards Miro2p12 (0.02 mg/ml) was injected, which also binds as shown by the increase of the resonance signal. For ending the experiment, the endotoxin-T4p12 binding was again released by addition of EDTA. The injection phases are indicated by the bars. As running buffer 20 mM Hepes, 150 mM NaCl, 0.1 mM $CaCl_2$ was used. The second unloaded cell of the chip was used as a reference cell. The curve shows the difference between measure and reference cell. RU means resonance units; s means seconds.

Figure 7:
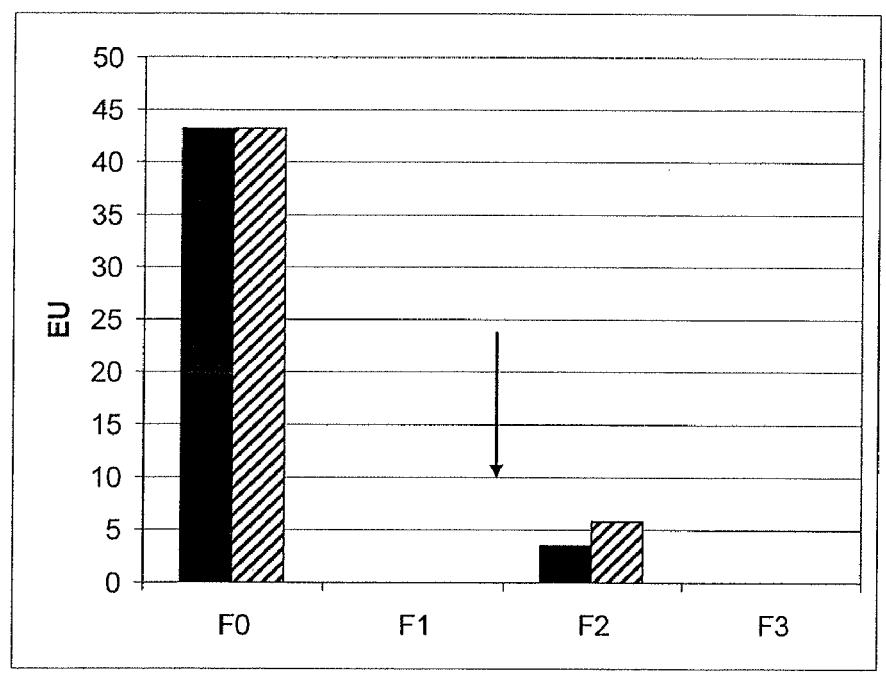

FIG. 7 shows the result of the endotoxin removal from human serum by N-Strep-Miro2p12 immobilized to sepharose. Each 1 ml of human serum, studded with endotoxin of E. coli O55:B5 (F0), was applied onto two N-Strep-Miro2p12-sepharose columns (column volume: 1 ml, column1=black bars, column2=dashed bars) and was collected in fractions of 4 and 3 ml, respectively, (F2, F3) after the columns. The arrow marks the application of sample. Before the application, the column was washed with 1 ml running buffer to be sure, that the column is not contaminated by endotoxin. The running buffer was composed of the following: 20 mM Hepes, 150 mM NaCl, 2 mM EDTA, pH 7.5. It was possible to remove 90% of the applied endotoxins from the serum, i.e. to be retained on the column.

Figure 8:
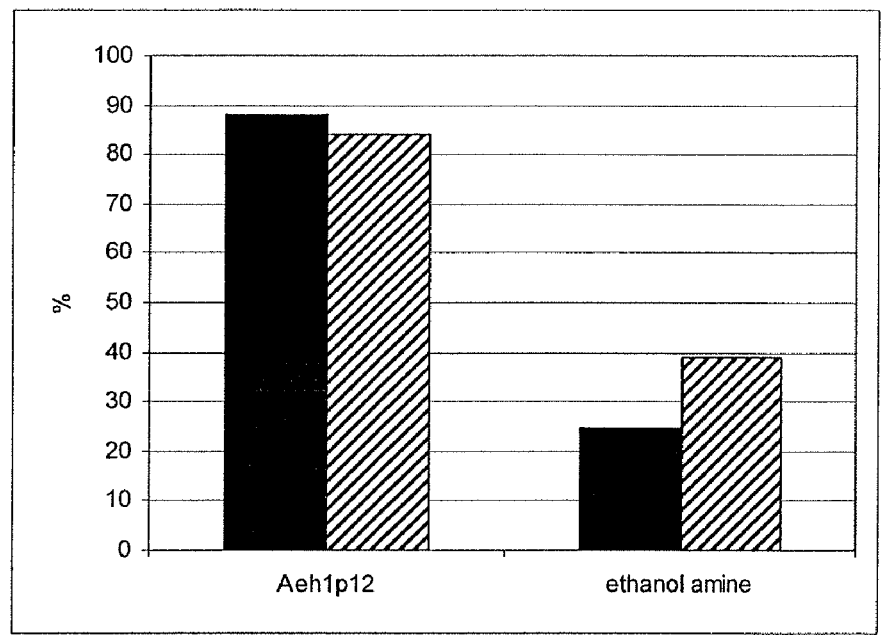

FIG. 8 shows the result of the endotoxin removal by Aeh1p12 immobilized to sepharose (2.5 mg Aeh1p12 per 1 ml sepharose) in comparison to sepharose, which is loaded with ethanolamine instead of Aeh1p12 to saturate the reactive groups of the activated sepharose. The experiment was carried out with and without calcium in the running buffer to determine the influence of calcium to the endotoxin removal. The running buffers were composed of as following: black bars (+Ca): 20 mM Hepes, 150 mM NaCl, 0.1 mM $CaCl_2$, pH 7.5. Dashed bars (−Ca): 20 mM Hepes, 150 mM NaCl, 2 mM EDTA, pH 7.5. Each 0.2 ml columns were cast and washed with 2 ml 0.5% sodium deoxycholate, 15 ml water and 2 ml running buffer before the experiment. Afterwards 0.2 ml lipopolysaccharide of E. coli O55:B5 (approximately 1000 EU/ml), solved in their respective running buffer, were applied. Said sample was incubated for 30 min at room temperature, was allowed to run through the column and was washed with 0.6 ml and 1 ml running puffer. The endotoxin content of the fractions was determined via LAL-test and the percental endotoxin removal was calculated by the amounts of endotoxin before and after the column. It was possible to remove significant more endotoxin from the solution by Aeh1p12 (88% and 84%) as by the control column (25% and 39%) containing no protein. Free calcium is not necessary for binding endotoxin to Aeh1p12, because the endotoxin removal was similarly with calcium (88%) and without calcium (84%).

Figure 9:
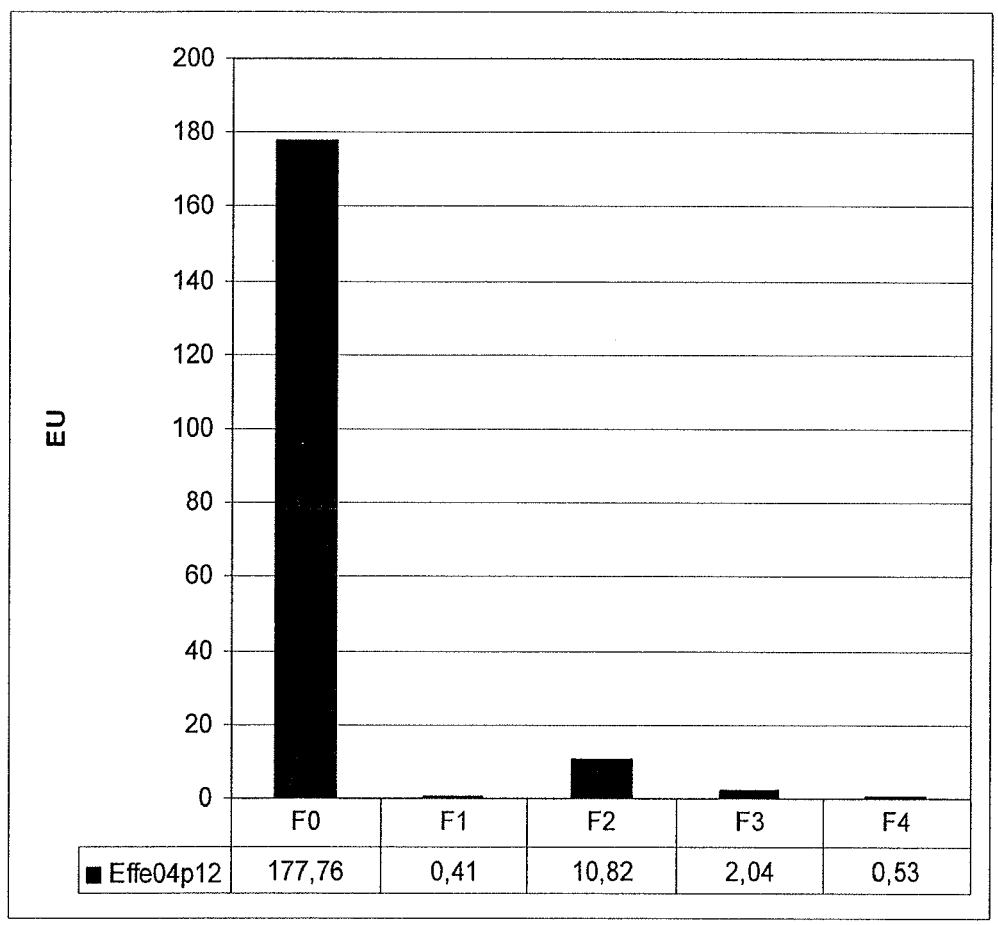

FIG. 9 shows the result of the endotoxin removal by Effe04p12. For this, the protein was coupled covalent to sepharose and afterwards incubated with an endotoxin solution, which was again separated from sepharose by centrifugation. The endotoxin removal was carried out in calcium free buffer (20 mM Hepes, 150 mM NaCl, 2 mM EDTA, pH 7.5). At first 100 μL Effe04p12-sepharose was washed with 1 ml endotoxin free buffer (F1) and afterwards 100 μL endotoxin solution (lipopolysaccharide of E. coli O55:B5) was applied onto said Effe04p12 sepharose. The sepharose was incubated for 30 min with the endotoxin solution and mixed for several times in doing so. Afterwards the solution was separated from sepharose by a Mini-Spin column and washed with 200 µL buffer (F2). Finally, the solution was washed another two times with each 200 µL (F3 and F4). The endotoxin content in the application (F0) and the fractions was detected via LAL-test and out of it, the percental endotoxin removal was calculated to 92.5%.

Figure 10:
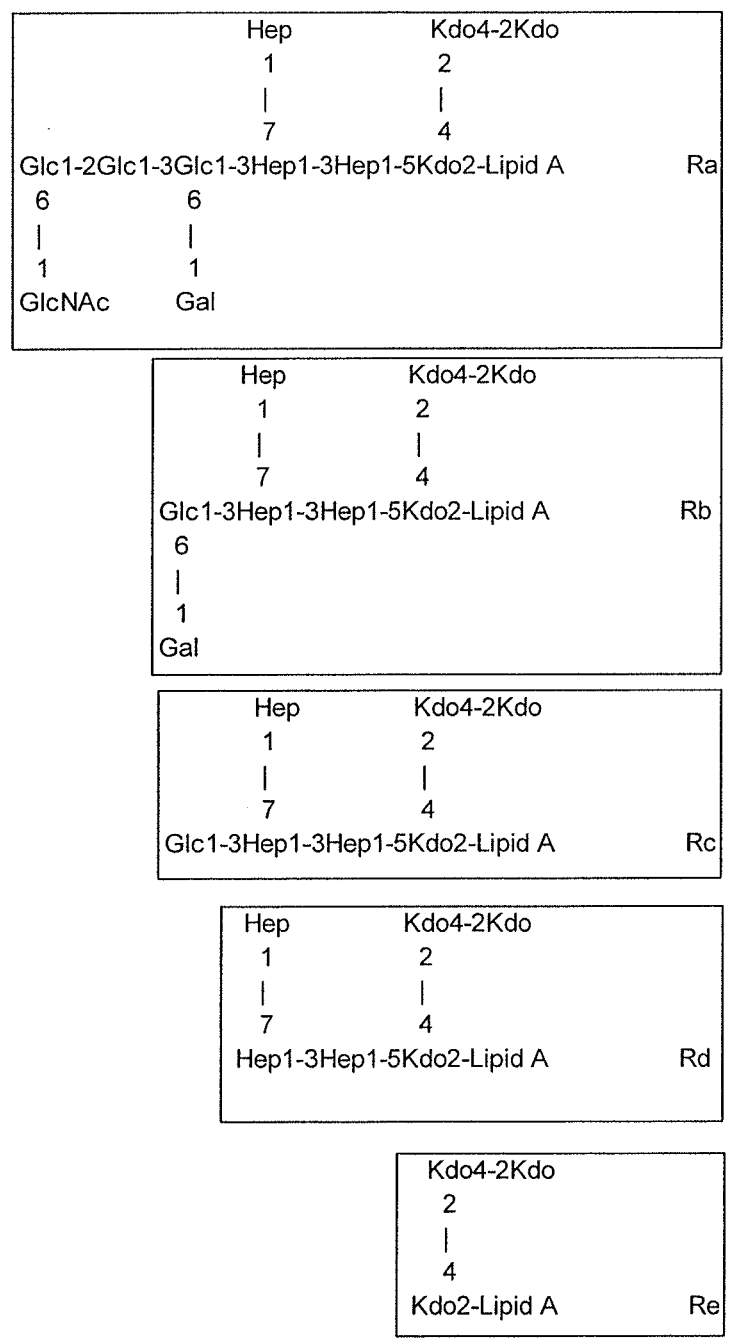

FIG. 10 shows the core-sugar structures of *E. coli* mutants, which were used for binding investigations with N-Strep-Miro2p12. Hep=heptose, Kdo=2-keto-3-deoxy-octonate, Glc=glucose, Gal=galactose, GlcNAc=N-acetylglucosamine.

FIG. 11 shows the sequence comparison on the level of amino acids between bacteriophage tail proteins (SEO ID NO:21, 22, 23, 24, 25, 26, 27, 12, 28, 29, 8, 10, 30, 31, 14, and 32, respectively). The sequence comparison was carried out with Clustal V (1.81) under following settings, wherein the sequences of T4p12, T2p12 and K3p12 were first aligned with the "Multiple Alignment Mode": Alignment parameter:
Pairwise Parameters:
Pairwise Alingmentsd Slow-Accurate
Gap Opening [0-100]: 10
Gap Extension [0-100]: 0.1
Protein Weight Matrix: Gonnet 250
Multiple Parameters
Gap Opening [0-100]: 10
Gap Extension [0-100] 0.2
Delay Divergent Sequences (%): 30
Protein Weight Matrix: Gonnet Series
Protein Gap Parameters
Residue-specific Penalties: ON
Hydrophilic Penalties: ON
Hydrophilic Residues: GPSNDQEKR
Gap Separation Distance [0-100]: 4
End Gap Separation: OFF
Quality—Column Score Parameters:
Score Plot Scale: 5
Residue Exception Cutoff: 5
Protein Weight Matrix: Gonnet PAM 250

The sequences of the phages can be located in the protein sequence database of the NCBI for the alignment and they are new isolated proteins by the inventors, respectively, and sequences thereof. 44R2.8t, Acc.No: AAQ81466; RB49, Acc.No: AAQ15392; T2, Acc.No: CAA39905; T4, Acc.No: AAD42417; PP01, Acc.No: BAD20635; RB69, Acc.No: AAP76072; Ach1, Acc.No: AAQ17871; KVP40, Acc.No: AAQ64417; AR1, Acc.No: AAN03609. The corresponding proteins of the phages PHG31 and RB43 can be found under phage.bioc.tulane.edu; the protein of the phage K3 is described in Burda M.R., Hindenach I., Miller S., Biol. Chem. (2000) 381, 225-258.

Figure 12:
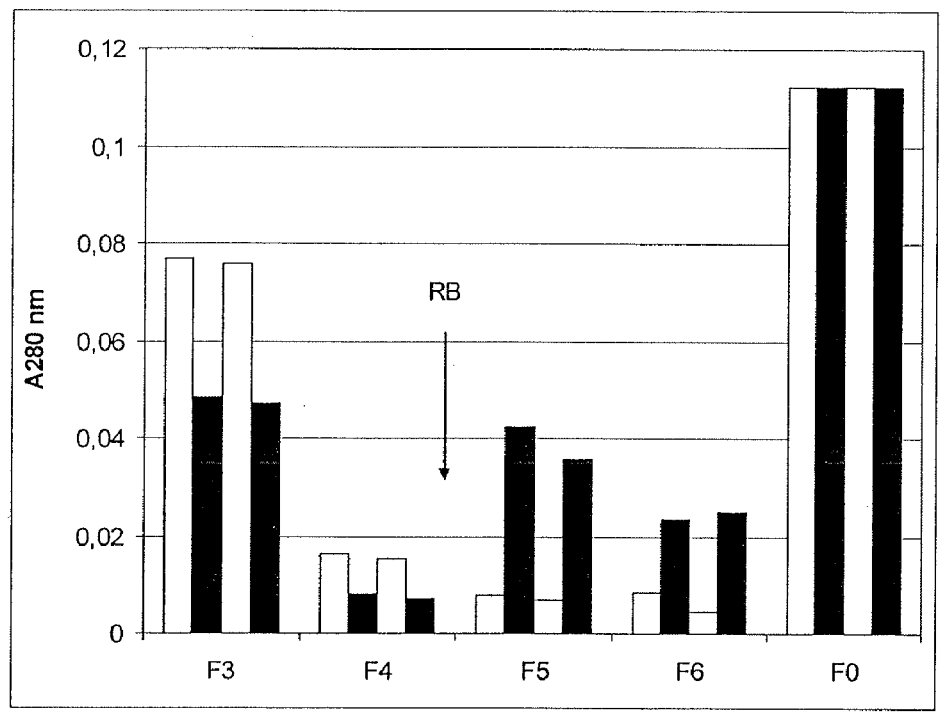

FIG. 12 shows the result of the endotoxin detection by the formation of a Miro2p12-endotoxin-Miro2p12-sandwich in a column chromatography method. Four columns were used (volume 1 ml), in which Miro2p12 was covalent coupled to sepharose (5 mg protein/ml column material), as described in example 5. Two of these were loaded with LPS of *E. coli* O55:B5 ($10^6$ EU in 1 ml PLS buffer, 10 mM sodium phosphate, 70 mM NaCl, pH 7.4) (+ET, black bars) and two were used as controls (-ET, white bars). As running buffer 10 mM sodium phosphate, 80 mM NaCl, pH 7.4 was used. Miro2p12 was applied onto all columns (each 600 µL of a solution with 0.1 mg/ml protein). The amount of the applied and eluted Miro2p12, respectively, was detected by absorption at 280 nm. The amount of bacteriophage tail protein Miro2p12 was plotted against the fractions of the chromatography run. Fraction 3 (F3) shows the flow-through of Miro2p12 after the application (F0), so all bacteriophage tail protein, which was not retained by the column, fraction 4 (F4) is a wash fraction. After the washing, the regeneration buffer RB (10 mM sodium phosphate, 500 mM NaCl, pH 7.4) was added (see arrow direction), which released Miro2p12 bound to endotoxin from the column. Following, fractions 5 and 6 were collected. Fraction F3 has a volume of 0.6 ml, all other fractions have a volume of 1 ml. As control the application onto the column (F0) is represented with the total amount of Miro2p12. It can be seen, that Miro2p12 is retained in the columns immobilized with endotoxins beforehand, while only a small amount of Miro2p12 is unspecifically bound to the control columns without endotoxin.

Figure 13:
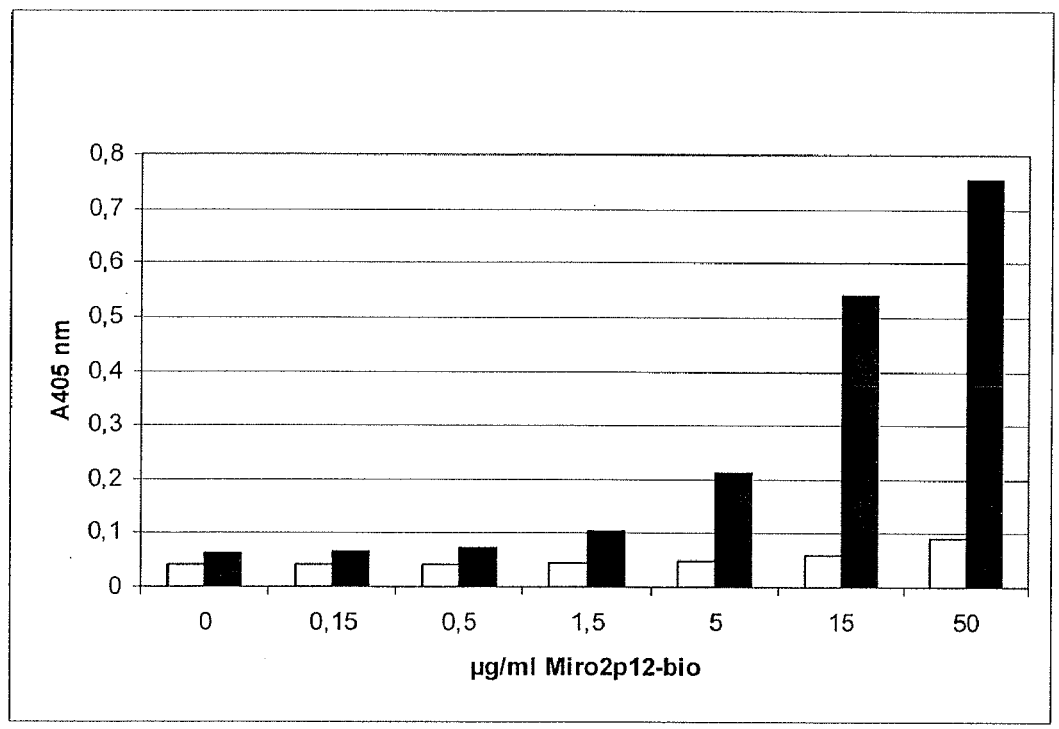

FIG. 13 shows the result of the direct detection of immobilized endotoxin by biotin labeled Miro2p12. LPS of *E. coli* O55:B5 (3 µg/ml) was immobilized to PolySorp-plates (Nunc) by adsorption (18 h at room temperature in PBS buffer, 10 mM $Na_2HPO_4$, 1.8 mM $KH_2PO_4$, 137 mM NaCl, 2.7 mM KCl, pH 7.4). Afterwards the microtiter plates were blocked with casein (0.05% in PBS, 1.5 h at RT) and washed with PBS buffer for one time. Control plates were not incubated with endotoxin but only blocked with Casein. Each 200 µl Miro2p12 labeled with biotin (Miro2p12-bio) in 50 mM Tris, pH 8, 0.05% Casein, 0.05% Tween20 was added in raising concentration (white bars: plates without ET, black bars: plates with ET, protein concentration as described). The detection of endotoxin bound to Miro2p12 labeled with biotin was carried out by an absorption measurement at 405 nm after the binding of a conjugate of Streptavidin with alkaline phosphatase (Amersham Biosciences) during the addition of pNPP (para-nitrophenylphosphate) in a concentration of 0.8 mg/ml as a chromogenic substrate. Miro2p12 labeled with biotin binds in a concentration dependent form to the microtiter plates, which were coated with endotoxin previously.

Figure 14:
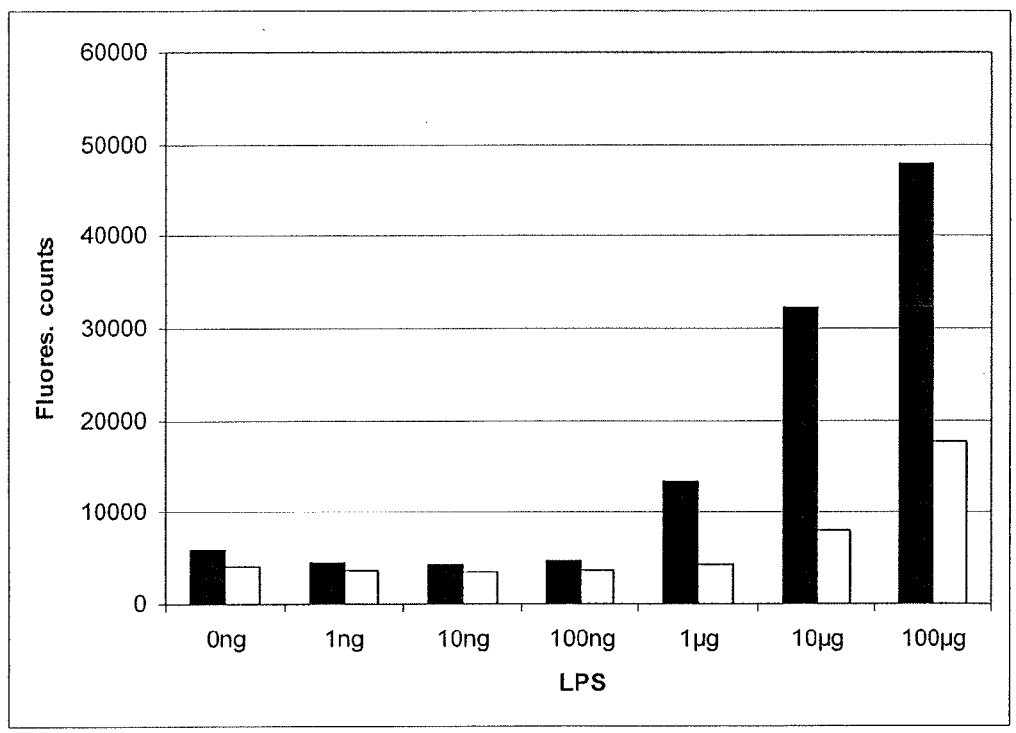

FIG. 14 shows the result of binding of endotoxin labeled with FITC at a surface, which were previously coated with Miro2p12. The detection of endotoxin bound to bacteriophage tail protein is carried out in a FITC specific ELISA. Miro2p12 (each 200 µl with 5 µg/ml protein) was adsorbed to a MaxiSorp plate (Nunc) (16 h at room temperature in PBS, 10 mM $Na_2HPO_4$, 1.8 mM $KH_2PO_4$, 137 mM NaCl, 2.7 mM KCl, pH 7.4). Afterwards the microtiter plates were blocked with casein (0.05% casein in PBS, 1.5 h at room temperature, each 200 µL per well) and washed with PBS buffer for one time. Control plates were not incubated with Miro2p12, but only blocked with Casein. Each 100 µL of FITC labeled LPS of *E. coli* O55:B5 (Sigma) in PBS were added in a raising concentration (white bars: plates without Miro2p12, black bars: plates with Miro2p12). The detection of the fluorescence labeled LPS bound to Miro2p12 was carried out by the binding of FITC specific antibodies (0.5 µg/ml, Zymed) in a first step and a secondary antibody, which was conjugated to an alkaline phosphatase (1 µg/ml, Pierce). The quantification was carried out by a fluorescence measurement of the reaction products of a fluorescent alkaline phosphatase substrate (methylumbelliferylphosphate; Sigma) with 0.1 mg/ml methylumbelliferylphosphate in 50 mM Tris, pH 8 (excitation at 375 nm; emission at 465 nm). Endotoxin labeled with fluorescence binds in a concentration dependent form to the microtiter plates, which where previously coated with Miro2p12.

The term "endotoxin depletion" or "endotoxin removal" as used herein means entire or partial endotoxin removal from the sample material.

The term "sample material" or "sample" as used herein comprises all kinds of solutions, in which endotoxin should be detected or from which endotoxins should be removed. Exemplary for samples is the following listing: water, aqueous solutions and mixtures of water and organic solvents, blood, blood products, plasma, serum, urine, media, protein solutions, water-ethanol mixtures, food. Also solutions, in which no aqueous solid substances for investigation or for isolation are solved, are further comprised such as protein, DNA, RNA, sugar, salts, drugs, vaccines, food, organic or inorganic chemicals (e.g. NaCl, $MgCl_2$, purine, pyrimidine, etc.).

The term "endotoxin" as used herein describes bacterial lipopolysaccharide (LPS), which is a component of the outer membrane of gram-negative bacteria.

The term "calcium independent bacteriophage tail protein" as used herein describes such proteins, which can be found in bacteriophages and which are able to bind endotoxin independently of the presence of bivalent positive ions such as $Ca^{2+}$ or $Mg^{2+}$. Usually such proteins are located in the tail of the bacteriophage, but they can also be located on the head of the bacteriophage or at bacteriophages, having no tail, at the normal casing of the bacteriophage. The term bacteriophage tail protein comprises as well short as long bacteriophage tail proteins. So bacteriophages with a basis plate (e.g. myoviridae like T4-similar phages) are able to have different bacteriophage tail proteins, so called long and short bacteriophage tail proteins, which also have different specificity for structures of bacteria membranes. Therefore the term "bacteriophage tail protein" comprises not only the endotoxin binding bacteriophage tail proteins but also the endotoxin binding bacteriophage head proteins and bacteriophage casing proteins. As a result calcium dependent bacteriophage tail proteins are such, which are only able to bind endotoxins in the present of bivalent positive ions as $Ca^{2+}$ or $Mg^{2+}$.

The term "unspecific immobilization" or "undirected immobilization" as used herein means that the coupling of a protein to a matrix occurs by protein residues (e.g. primary amines), which are spread over the total protein surface. The selection of the used group of the single protein molecules for coupling is randomly.

The term "directed immobilization" as used herein means, that the coupling occurs by amino acid residues or other residues (e.g. glycosylation of the protein), their position in the protein (e.g. N- or C-terminal) is known. The selection of the group for coupling occurs by the selection of suitable reaction partners/linker, which prefer to react with these residues (e.g. coupling of sulfhydryl residues to iodoacetate residues; iodoacetate reacts thousand times faster with sulfhydryl residues as with amino residues).

The term "surface" or "carrier" as used herein comprises all materials to which a coupling or adhesion of a protein molecule is possible, e.g. glass surfaces, chromatography materials, e.g. agarose or sepharose, plastic surfaces, e.g. polystyrene or polypropylene, filter materials, e.g. cellulose.

The present invention relates to bacteriophage tail proteins and derivates and fragments thereof, which are able to bind endotoxin independently of the concentration of bivalent positive ions, in particular in the absence of bivalent positive ions, in particular $Ca^{2+}$ and/or $Mg^{2+}$.

In the difference to so called calcium-dependent bacteriophage tail proteins, as such, which are only able to bind endotoxin in the present of bivalent positive ions, in particular $Ca^{2+}$ and/or $Mg^{2+}$, said calcium-independent bacteriophage tail proteins allow the endotoxin detection in and the endotoxin removal from samples, which contain no bivalent positive ions, in particular $Ca^{2+}$ and/or $Mg^{2+}$.

The bacteriophage tail proteins according to the present invention are also called in the following as "calcium-independent bacteriophage tail proteins". Preferred are short tail proteins. Further bacteriophage tail proteins of the family of myoviridae are preferred, in particular of the group of pseudo-T-even, schizo-T-even or T-even phages. Further bacteriophage tail proteins are preferred, which bind to 2-keto-3-deoxyoctonic acid (Kdo) of endotoxins. Further bacteriophage tail proteins are preferred, which are available as trimers and are resistant against sodium dodecyl sulfate (SDS).

The present invention relates in particular to bacteriophage tail proteins according to SEQ ID NO:2 (Miro1p12), SEQ ID NO:4 (Miro2p12) and SEQ ID NO:6 (Effe04p12) as well as the DNA sequences according to SEQ ID NO: 1 (Miro1p12), SEQ ID NO:3 (Miro2p12) and SEQ ID NO:5 (Effe04p12) encoding the bacteriophage tail proteins according to the invention. The present invention further relates to modified bacteriophage tail proteins and the DNA sequences encoding modified bacteriophage tail proteins according to the present invention. Modified bacteriophage tail proteins have e.g. a His-tag or a Strep-tag to ease the isolation of the proteins after a recombinant production in bacteria. Exemplary bacteriophage tail proteins according to the present invention with a Strep-tag are the SEQ ID NO:8 (N-Strep Miro1p12), SEQ ID NO:10 (N-Strep Miro2p12), SEQ ID NO:12 (N-Strep Effe04p12) and SEQ ID NO:14 (N-Strep Aeh1p12) as well as the encoding DNA sequences SEQ ID NO:7 (N-Strep Miro1p12), SEQ ID NO:9 (N-Strep Miro2p12), SEQ ID NO:11 (N-Strep Effe04p12) and SEQ ID NO:13 (N-Strep Aeh1p12). The present invention further relates to fragments of bacteriophage tail proteins and the DNA sequences encoding the fragments of the bacteriophage tail proteins according to the present invention. Because the N-terminus of this phage proteins is often responsible for binding to phages and the C-terminus for binding to bacterial receptor, as shown for phage T4 (Makhov A M, et al., Virology. 1993 May; 194(1): 117-127), in particular C-terminal fragment are preferred. Derivates or fragments are able to be gained e.g. by limited proteolysis (van Raaij M J, et al., Biol. Chem. 2001 July; 382(7):1049-1055) or randomly genetically produced. Fragments are preferred, which comprises the binding region to the bacterial receptor.

The bacteriophage tail proteins according to the present invention are able to be used for following described methods for removing and for detecting endotoxin. The bacteriophage tail proteins according to the present invention bind endotoxin and are substantially independently of the concentration of bivalent positive ions e.g. $Ca^{2+}$ and/or $Mg^{2+}$. So the endotoxins may be present in solutions or samples, which contain or which not contain bivalent positive ions. Further substantially independent means, that the solution or sample has no free or bound bivalent positive ions. On the one hand the solution or sample may be totally free of bivalent positive ions. On the other hand it is possible, that the bivalent positive ions are present in the solution or sample bound to substances, which bind bivalent positive ions e.g. EDTA, HEDTA, EGTA, citrate and similar.

There exist two groups of bacteriophage tail proteins which may be differed in whose binding because of the dependence of bivalent positive ions such as Calcium. P12 bacteriophage tail proteins e.g. of the myoviridae phages as T4, T2, K3, Ox2, RB32-33, AR1, PP01 or RB69 require calcium for binding endotoxin, while the bacteriophage tail protein according to the present invention of the phages Miro1, Miro2 and Effe04 as well as the structural similar proteins to said bacteriophage tail proteins e.g. RB43p12, RB49p12, 44RR2p12, PHG31p12, Aeh1p12 and KVP40p12 are also able to bind endotoxin without calcium or other bivalent positive ions.

The binding mechanism of calcium-independent bacteriophage tail protein Miro2p12 to endotoxin differs from that of the calcium-dependent bacteriophage tail protein T4p12. T4p12, a calcium dependent bacteriophage tail protein, requires the heptose-Kdo region in the inner core region of endotoxins for binding endotoxin. In contrast, Miro2p12, a calcium independent bacteriophage tail protein, does not requires the heptoses of the inner core region for binding, in fact, Miro2p12 is able to bind also mutants in the core region, which only have the 2-keto-3-deoxyoctonic acid (Kdo), see table 1. The described experiments in FIG. 5 and FIG. 6 document these as well, in which Miro2p12 and T4p12 bind endotoxin at the same time and therefore at different binding sides.

The present invention further relates to a method for removing endotoxins from a sample, comprising the steps:
  a. incubating or contacting bacteriophage tail proteins to a sample unspecifically or directed immobilized to a solid carrier, wherein the bacteriophage tail proteins are able to bind endotoxin independently of bivalent positive ion concentrations, and subsequently
  b. separating the endotoxin-bacteriophage tail proteins complex from the sample.

For said depleting method according the present invention, the bacteriophage tail proteins according to the present invention are coupled to solid carrier. The solid carrier may be filling material for chromatography columns (e.g. sepharose materials), cellulose, filtration media, glass particles, magnetic particles, centrifugations materials or sedimentation materials (e.g. agarose particles).

Important hereby is a functional coupling, i.e. bacteriophage tail proteins have despite of the binding to the carrier material accessible structure for endotoxin. The coupling of the bacteriophage tail proteins may be unspecific or however preferably directed, by e.g. a selective biotinylation or coupled by a spacer or a linker.

Besides it is possible that the bacteriophage tail proteins according to the present invention are linked with low molecular substances e.g. biotin to bind to polypeptides e.g. Streptavidin, which are immobilized to a carrier on their parts, by this low molecular substances. Further, instead of biotin it is possible to use said Strep-tag (Skerra, A. & Schmidt, T. G. M., Biomolecular Engineering, 16 (1999), 79-86), which is a short amino acid sequence and binds to Streptavidin. Further it is possible to use the His-tag, which is able to bind to a carrier material by bivalent ions (zinc or nickel) to chelator material as nickel nitrilotriacetate (Ni-NTA, Qiagen, GmbH, Hilden; tolerate no EDTA) or nickel sepharose (General Electric Healthcare/Bio-Sciences/Amersham Biosciences Europe GmbH, Freiburg; tolerate low EDTA concentrations) or a specific antibody for it (Qiagen GmbH, Hilden). The Strep-tag as well as the His-tag is preferably bound by DNA recombination technology to the bacteriophage protein. This coupling may occur directed, e.g. to N-terminus or C-terminus or undirected. The directed coupling occurs by a suitable reactive, usually for phage proteins a not often surface exposed amino acid as cystein, which is inserted at a suitable point. Because bacteriophage tail proteins are synthesized in the cytoplasma, it is not reckon with disulfide bonds. Preferable it is possible to couple direct by other amino acids or by a spacer or cross linker such as cystein (mono functional or bi functional).

During the cystein coupling all bi functional cross linker are possible with NH reactive or SH reactive groups, with or without spacer, e.g. 1'-maleimidoundecanoic acid sulfo-NHS or Succinimidyl-4-[N-maleimidomethyl]-cyclohexane-1-carboxy-[6-amido]caproate. Unless there are no spacers, 8-12 C-atom spacers with a terminal NH-group are able to be inserted. Preferable the cystein coupling occurs by a specific biotinylation of the cystein by e.g. EZ-link PEO-Maleimide activated biotin (Pierce).

Further it is possible that the coupling occurs by known coupling reactions to protein residues, e.g. carboxyl, amino, hydroxyl or sulfhydryl residues.

The concentration of free not bound bivalent positive ions is preferable less than approximately 0.1 µM.

The separation of endotoxins can be carried out in a chromatographic method or in the so called batch method. During the batch method the sample charged with endotoxin is mixed and incubated with carrier material, to which the bacteriophage tail proteins according to this invention are coupled covalently.

The separation is carried out after the incubation of the sample with the corresponding with bacteriophage tail protein coupled carrier material for approximately 5-60 min or approximately 30-180 min or over night if required. The duration of the incubation has to be adjusted to the respective sample and may vary between 1 min and 24 h. Therefore the sample e.g. is eluted or filtrated from the chromatography column or the corresponding particles are centrifuged or sedimented and magnetically separated by application of a magnetic field, respectively. In particular the separation described in this batch method, i.e. with preincubating the sample and with the corresponding bacteriophage tail protein coupled carrier material, makes sense at very low endotoxin concentrations.

The depletion of endotoxins by chromatography column may also be carried out in pure flow-thorough methods. Therefore the carrier material charged with the bacteriophage tail protein according to the present invention is cast to a chromatography column. For this the sample may be applied onto the column, which comprises the bacteriophage tail proteins coupled to the carrier material. The sample charged with endotoxins is applied onto this column and flows through it, wherein the endotoxin binds to the bacteriophage tail proteins and remains on the column. Ideally the sample itself shows no interactions with the chromatography material and is located in the flow-through. The flow rate is dependent of the volume and the geometry of the column. Further the flow rate is dependent of the volume and the endotoxin content of the sample to achieve also at low endotoxin concentration an efficient depletion by a contact time between column and endotoxin as long as possible. Thereby the contact time is the time, which the sample needs from the application onto the column until the outflow. The endotoxin bound onto the column may be removed from the column by washing with suitable buffers, so that it is possible to use the column several times.

The used bacteriophage tail proteins for said method of removing endotoxins according to this invention may be all preceding described bacteriophage tail proteins according to the present invention and derivates and fragments thereof, in particular according to SEQ ID NO:2, 4, 6, 8, 10, 12, 14.

A further aspect of the present invention regards methods for detecting endotoxin. The endotoxin detection is carried out either by a direct detection of the bacteriophage tail protein bound to endotoxin or indirect by the detection of excessive, not bound bacteriophage tail protein in the supernatant or the flow-through.

The direct endotoxin detection comprised the following steps:
  a. contacting the endotoxin containing sample to a surface, and subsequently optionally
  b. removing the sample from the surface, subsequently c. incubating of bacteriophage tail proteins with the endotoxins immobilized to the surface, wherein the bacteriophage tail proteins are able to bind endotoxin independently of the bivalent positive ion concentration, and subsequently optionally
d. removing the unbound bacteriophage tail proteins, and subsequently
e. detecting of the bacteriophage tail proteins bound to endotoxin In the first step the binding of endotoxin occurs to the surface. The surface may be coated with an endotoxin binding ligand by means of adsorption or covalent coupling. As surfaces different synthetics are preferred e.g. polystyrene, polypropylene, polyethylene, polycarbonate, PMMA, cellulose e.g. cellulose acetate, nitrocellulose, glass, silicon or agarose. The covalent immobilization of endotoxin binding ligands, e.g. polymyxin B, histamine, histidine, poly-L-lysine, DEAE, polyethylenimin, deoxycholic acid, poly γ-amino methyl-L-glutamine, polyvinyl alcohol, poly-N,N-dimethylaminopropylacrlyamide, dextran, chitosan or calcium independent bacteriophage tail proteins is carried out by known coupling reactions. Alternatively it is possible to bind these ligands by means of biotin-Streptavidin coupling to the surface.

The calcium independent bacteriophage tail proteins can be used either for binding endotoxins to the surface or for detecting bound endotoxins. Because endotoxins are normally not monomer but form aggregates in the solution (Mueller M, et al., J Biol. Chem. 2004 Jun. 18; 279(25): 26307-26313) it is also possible to achieve the binding of endotoxins by means of a calcium independent phage tail protein and to use the same calcium independent phage tail protein for detecting endotoxins.

Likewise it is possible to use a combination of Ca dependent and Ca independent bacteriophage tail proteins, wherein one of these acts for immobilization of endotoxin to the surface and the second for the detection of bound endotoxin.

Therefore a further method for detecting endotoxin comprises the following steps:
a. contacting the endotoxin containing sample to a surface immobilized with first bacteriophage tail proteins, said bacteriophage tail proteins are able to bind endotoxin independently of the bivalent positive ion concentration, and subsequently optionally
b. removing the sample from the surface, subsequently
c. incubating of second bacteriophage tail proteins to the endotoxins bound to the first bacteriophage tail proteins, wherein the second bacteriophage tail proteins bind endotoxins only in the presence of bivalent positive ions, and subsequently optionally
d. removing the unbound second bacteriophage tail proteins and following detection of the second bacteriophage tail proteins bound to endotoxin.

The method can also be carried out as the first bacteriophage tail protein is a Ca dependent and the second bacteriophage tail protein is a Ca independent bacteriophage tail protein.

The bacteriophage tail proteins, which should be applied for said detection according to the present invention, have only to have a marker, by whom the detection of the protein is subsequently carried out.

The endotoxine detection in or from a sample is carried out by the binding of bacteriophage tail proteins to endotoxin. These binding can be detected e.g. by direct measurement via spectroscopic methods, e.g. by means of fluorescence emission, fluorescence polarization, absorption or circular dichroism. Furthermore it is possible to make the binding visible by electric signals, e.g. by a capacity measurement. For fluorimetric detection the bacteriophage tail proteins are substituted with fluorescence markers, e.g. fluorescein, Alexa448 or similar. Alternatively, the detection is carried out by a similar method to ELISA, wherein firstly specific antibodies bind to the bacteriophage tail proteins. The detection of these antibodies is carried out by means of enzymes, which are fused either directly with the antibody or with a so-called second antibody, which bind to the first antibody. As enzymes alkaline phosphatase or the horseradish peroxidase are considered particularly, but also others. Said enzymatic marker proteins can also be coupled directly to the bacteriophage tail protein. This can be carried out either by the production of fusion proteins or by chemical coupling of both proteins. Alternatively, it is possible to mark the bacteriophage tail proteins with biotin, which may be detected by enzymes coupled to Streptavidin, as alkaline phosphatase or horseradish peroxidase.

A further method for the direct detection of endotoxin comprises the following steps:
a. contacting the endotoxin containing sample to a surface immobilized with first bacteriophage tail proteins, said bacteriophage tail proteins are able to bind endotoxin independently of the bivalent positive ion concentration, and subsequently optionally
b. removing the sample from the surface, subsequently
c. detecting the endotoxins bound in step a)

The detection of endotoxin, which is bound to a Ca independent bacteriophage tail protein, may be carried out by means of an endotoxin specific ELISA or by chemical or enzymatic detection reactions of endotoxins or separated endotoxin components.

The indirect detection comprises the following steps:
a. contacting the endotoxin containing sample to a surface, and subsequently optionally
b. removing the sample from the surface, subsequently
c. incubating of bacteriophage tail proteins with the endotoxins immobilized to the surface, wherein the bacteriophage tail proteins are able to bind endotoxin independently of the bivalent positive ion concentration, and subsequently optionally
d. removing the unbound bacteriophage tail proteins, and subsequently
e. detecting of the unbound bacteriophage tail proteins obtained in step d.

If endotoxins are bound to calcium independent bacteriophage tail proteins immobilized to said surface, the method comprises the following steps:
a. contacting the endotoxin containing sample to a surface immobilized with first bacteriophage tail proteins, said bacteriophage tail proteins are able to bind endotoxin independently of the bivalent positive ion concentration, and subsequently optionally
b. removing the sample from the surface, subsequently
c. incubating of second bacteriophage tail proteins to the endotoxins bound to the first bacteriophage tail proteins, wherein the second bacteriophage tail proteins bind endotoxins only in the presence of bivalent positive ions, and subsequently optionally
d. removing the unbound second bacteriophage tail protein, and subsequently
e. detecting of the unbound second bacteriophage tail protein obtained in step d.

The binding of the endotoxins occurs either by calcium independent bacteriophage tail proteins, which are immobilized to said surface as described above, or by other endotoxin binding surfaces. The detection of bound endotoxins is carried out by calcium independent or calcium dependent bacteriophage tail proteins, which are added after the binding of the endotoxins to the surface, which have an additional marker, by which they are detected. These are given in known concentrations to the surface with said endotoxins, are incubated and afterwards the unbound labeled bacteriophage tail proteins are removed or washed out again. By the decrease of the labeled bacteriophage tail proteins in the supernatant or flow-trough the endotoxin amount, which has bound to the surface, is detected.

Furthermore, it is possible to detect endotoxin by a competitive test, in which the labeled endotoxins or labeled endotoxin constituents compete against the endotoxin contained in the sample for binding sides of the calcium independent phage proteins. The endotoxin detection is carried out in this test also indirect by the detection of the calcium independent bacteriophage tail proteins bound to labeled endotoxin or by the labeled endotoxins, which did not bound to the calcium independent bacteriophage tail protein because of the competitive inhibition.

The competitive detection comprises the following steps:
a. mixing the sample with endotoxins, which are coupled to a marker, subsequently
b. applying the mixture of step a) to a surface with immobilized bacteriophage tail proteins, wherein the bacteriophage tail proteins are able to bind endotoxin independently of the concentration of bivalent positive ions, subsequently
c. removing the mixture from the surface, subsequently
d. washing the surface, and subsequently
e. detecting the labeled endotoxins on the surface and/or the free labeled endotoxin of the pooled samples after step c) and d).

The required endotoxins for this detection are gained by known methods for purification of endotoxins (Galanos C., et al., (1969), Eur. J. Biochem. 9, 245-249; Westphal O., Jann K. (1965) In R. L. Whisthler (ed.) Methods in carbohydrate chemistry, vol. 5, 83-91) and are supplied with markers. For labelling the same marker are used as for the bacteriophage tail protein according to the present invention as fluorescence marker, biotin, digoxigenin, antibodies, enzymatic markers or other markers and with this the corresponding detection methods. Only the coupling, which occurs for endotoxins by the sugar residues, is differently and occurs according to known methods for labeling sugars (Toelstra A. et al. (1997) J. Leukoc. Biol. 61, 170-178; Triantafilou K. et al. (2000), Cytometry 41, 316-320). The quantification is carried out by a concentration series with a standard endotoxin.

The calcium independent bacteriophage tail protein used in the detections according the present invention may be the bacteriophage tail proteins according to the present invention described above, which also can be used for removing endotoxin.

The following examples are provided merely by way of explanation and in no sense restrict the scope of invention. If not else declared, molecular biologic standard methods were used, e.g. described by Sambrook et al., 1989, Molecular cloning: A Laboratory Manual 2. edition, Cold Spring Harbor Laboratory Press, Cold Spring Harbor, N.Y.

EXAMPLE 1

Effect of Calcium on the Endotoxin Binding of T4p12, N-Strep-Miro2p12 and N-Strep-Aeh1p12

The short tail fibre proteins T4p12, N-Strep-Miro2p12 and N-Strep-Aeh1p12 were immobilized to NHS activated sepharose 4 Fast Flow (Amersham Biosciences) according to the instruction of the manufacturer and afterwards the binding of endotoxin to said sepharoses was examined. For that purpose columns were cast, a solution with endotoxin was applied onto said columns and the flow-through was collected. The endotoxin content in the application and in the flow-through was determined via LAL-test (kinetic chromogenic LAL-test, Cambrex). The columns had volumes of 1 ml for T4p12 and N-Strep-Miro2p12 and 0.2 ml for N-Strep Aeh1p12. Each 1 ml of a BSA solution (1 mg/ml) was applied onto T4p12 and N-Strep-Miro2p12 columns and 0.2 ml of a buffer solution to N-Strep-Aeh1p12 column. The applied solutions were all studded with endotoxin of E. coli O55:B5 (approximately 1000 EU/ml). To see the effect of calcium to the endotoxin removal and therefore the endotoxin binding, the experiment was carried out with calcium containing buffer and calcium free buffer. The calcium containing buffer consisted of 20 mM Hepes, 150 mM NaCl, 0.1 mM $CaCl_2$, pH 7.5 and the calcium free buffer of 20 mM Hepes, 150 mM NaCl, 2 mM EDTA, pH 7.5. The concentration of free calcium ions was 0.1 mM in the calcium containing buffer and under 1 µM in the calcium free buffer with the chelator EDTA (Bers D. et al., in Methods in Cell Biology 40, A practical guide to the study of $Ca^{2+}$ in living cells, chapter 1: A practical guide to the preparation of $Ca^{2+}$ Buffers, Academic Press, 1/94).

As shown in FIG. 1, it was only possible to remove endotoxin from the solution in the calcium containing buffer by T4p12 (99.9% endotoxin removal), while endotoxin was removed from the solution next to nothing in the calcium free buffer (3.2% endotoxin removal). The endotoxin removal was independent of the calcium concentration in the buffer by N-Strep-Miro2p12 sepharose. It was possible to remove over 99% of endotoxin as well with the calcium containing buffer (99.5% endotoxin removal) as with the calcium free buffer (99.9% endotoxin removal). It was also not possible to find an effect of the calcium concentration for N-Strep-Aehp12 sepharose. 88.5% of endotoxin was removed from the solution in the calcium containing buffer and 84.3% in the calcium free buffer.

EXAMPLE 2

1. Construction of Miro1, Miro2 and Effe04 with N-terminal Strep-tag: Via PCR the nucleotide sequence for the Strep-tag was added to the 5' end of the Miro2 gene (U.S. Pat. No. 5,506,121). Therefore a primer for the 5' end of the Miro2 gene was constructed (5'-GAA GGA ACT AGT CAT ATG GCT AGC TGG AGC CAC CCG CAG TTC GAA AAA GGC GCC GCC CAG AAT AAC TAT AAT CAC-3'; SEQ ID NO:15), which comprises the nucleotide sequence of the Strep-tag at its 5' end (cursive in the sequence) and a restriction recognition side (NdeI, underlined in the sequence) in that way, that the gene can be inserted into the right reading frame of the expression plasmid. A primer for the 3' end of the Miro2p12 gene (5'-CG GGA TCC TCC TTA CGG TCT ATT TGT ACA-3'; SEQ ID NO:16) was constructed, which adds a BamHI restriction recognition side behind the Miro2p12 gene (underlined in the sequence). The PCR was carried out with 35 cycles (15 s 94° C., 15 s 51° C., 1 min 74° C.). The PCR preparation was restricted with NdeI and BamHI and the fragment of interest was inserted into the NdeI and BamHI site of the expressions plasmid pET21a after size fractionation by an agarose gel and elution from the gel. The sequence of the Miro2p12 gene was verified by DNA sequencing. Afterwards the plasmid pNS-Miro2 was transformed into the expression strain BL21 (DE3).

The cloning of Miro1p12 was carried out analog to the described cloning of Miro2p12 above.

The same primer and restriction enzymes were used.

The construction and cloning of N-Strep-Effe04p12 was carried out analog to the procedure for N-Strep-Miro2p12 as described above. A primer was used for the 5' end of the N-Strep-Effe04p12 gene with the sequence 5'-GAA GGA ACT AGT GCT AGC GCT AGC TGG AGC CAC CCG CAG TTC GAA AAA GGC GCC AGT AAC AAT ACA ATC AAC CAC G-3' (SEQ ID NO:17), which contains a restriction side for NdeI (underlined in the sequence) and a nucleotide sequence for Strep-tag (cursive). For the 3' end a primer was used with the sequence 5'-CG GGA TCC CCT CTG TTA TAA TAC GCG-3' (SEQ ID NO:18), which comprises a restriction recognition side for BamHI (underlined in the sequence). The PCR preparation was restricted with NdeI and BamHI, inserted into the expression plasmid pET21a and transformed into the expression strain BL21(DE3).

EXAMPLE 3

Purification of N-Strep-Miro2 protein: The *E. coli* strain BL21(DE3) was raised with the plasmid pNS-Miro2 in a 2 l agitation culture (LB-medium with ampicillin, 100 µg/ml) until a OD600 of 0.5-0.7 at 37° C. and the expression of the N-Strep-Miro2 protein was induced by the addition of 1 mM IPTG (isopropyl-B-thiogalactopyranoside). After incubation at 37° C. for 4 h the cells were harvested. Harvest cells of 10 l culture were sustained into 50 ml 10 mM sodium phosphate, pH 8.0, 2 mM $MgCl_2$, 150 mM NaCl, disrupted by a French-Press treatment (20.000 psi) for three times and afterwards centrifuged for 30 min at 15.000 rpm (SS34). After washing for two times in the same buffer, the N-Strep-Miro2 protein was extracted from the pellet by stirring for 30 min in 10 mM TrisHCl pH 8.0, 150 mM NaCl, 1 M urea, the preparation was centrifuged for 30 min at 15.000 rpm (SS34) and the released N-Strep-Miro2 was embedded in the supernatant at 4° C. The extraction was repeated twice. The pooled supernatants were applied onto a streptactin affinity column (15 ml) equilibrated with buffer "W" (100 mM TrisHCl pH 8, 1 mM EDTA, 150 mM NaCl), (IBA GmbH, Göttingen, Germany). After washing with 5 column volumes of buffer "W" it was eluted with 3 column volume buffer "W" with 2.5 mM desthiobiotin in buffer "W". After dialyse against buffer "W" for several times and concentration, the concentration and purity of N-Strep-Miro2 was examined by SDS-PAGE and UV spectroscopy. Approximately 100 mg N-Strep-Miro2 were so purified from 10 liter culture.

EXAMPLE 4

Detection of the binding of different long endotoxin variations to N-Strep-Miro2p12 via surface plasmon resonance spectroscopy. This experiment conduces for the purpose to get information of the structure in the core region of endotoxin recognized by Miro2p12. N-Strep-Mirop12 was covalent coupled to the surface of a cell on a CM-5 Chip by company Biacore. Therefore at first the surface was activated with EDC/NHS, afterwards N-Strep-Miro2p12 was bound by primary amino residues and finally unused coupling groups were saturated with ethanol amine (see Biacore handbook). Endotoxin was isolated from *E. coli* strains, which have unequal long core sugars (see FIG. 9, Lit.: Boman H. G., Jonsson S., Monner D., Normark S., Bloom G. D., Cell-Surface alterations in *Escherichia coli* K-12 with chromosomal mutations changing ampicillin resistance. Ann. N.Y. Acad. Sci. 1971; 182: 342-357; Prehm P. Stirm S., Jann B., Jann K., Bomann H. G., Cell-wall lipopolysaccharides of ampicillin-resistant mutants of *Escherichia coli* K-12. Eur. J. Biochem. 1976; 66(2): 369-377; Eriksson-Grennberg K. R., Nordstrom K., Englund P., Resistance of *Escherichia coli* to penicillins. IX. Genetics and physiology of class II ampicillin-resistant mutants that are galactose negative or sensitive to bacteriophage C21, or both. J. Bacteriol. 1971; 108(3): 1210-1223; Boman H. G., Monner D. A., Characterization of lipopolysaccharides from *Escherichia coli* K-12 mutants. J. Bacteriol. 1975; 121(2): 355-464). Therefore the bacteria were raised in LB-medium at 37° C. over night, harvested by centrifugation, washed with PBS and afterwards the pellet was sustained into 100 mM Tris, 50 mM EDTA, pH 8 and incubated for 30 min at room temperature. In this buffer a part of the endotoxin is solved and can be separated from the cells. Afterwards the solved endotoxin was precipitated with four times volume of acetone and dried. For detecting endotoxin was sustained into running buffer (running buffer: 20 mM Hepes, 150 mM NaCl, 0.005% Tween 20, pH 7.5) and rinsed over the surface loaded with N-Strep-Miro2p12. A second unloaded cell on the Biacore Chip was used as a control. The endotoxin solution was applied onto both cells during the measurement and the resulting signal was calculated from the signal differences between cell1 and cell2. The increase of the signal in the resulting curve was interpreted as the binding of endotoxin to the N-Strep-Miro2p12. As shown in table 1, it was also possible to detect a binding with endotoxin from the *E. coli* strain D21f2. This stain comprises only the Kdo-Core sugars und therefore the shortest endotoxin form, which is absolute necessary for the survival of the cells. It was not possible to detect a binding of said bacteria with T4p12. Thereby the addition R means, that these bacteria belong to the so-called rough type whose endotoxin have no O-antigen and the small letters a to e mark the decreasing length of core sugars in the endotoxin. The corresponding core sugars are drafted in FIG. 9.

TABLE 1

| bacteria strain | binding to T4p12 | binding to N-Strep-Miro2p12 |
| --- | --- | --- |
| *E. coli* D21, Ra | + | + |
| *E. coli* D21e7, Rb | + | n.d. |
| *E. coli* D21e8, Rc | + | n.d. |
| *E. coli* D21f1, Rd | + | + |
| *E. coli* D21f2, Re | − | + | n.d. = not determined

EXAMPLE 5

Endotoxin Removal by the Bacteriophage Tail Protein Miro2

5 ml NHS activated sepharose 4 Fast Flow (Amersham Biosciences) was centrifuged, the isopropanole supernatant was removed and mixed with 870 ml citrate buffer (25 mM citrate, 2 mM EDTA, pH 7.0). Afterwards 217 ml bacteriophage tail protein Miro2 (0.46 mg/ml in 50 mM formiate, pH 3.5) were added und shacked for 2 hour at 37° C. for coupling the bacteriophage tail protein to the sepharose. The supernatant was removed, the sepharose was washed with 10 mM sodium phosphate, pH 10 for three times and 1 ml aliquots of supernatant and wash fractions were dialyzed against 10 mM sodium phosphate, pH 10. The concentration of bacteriophage tail protein in these aliquots was determined via absorption measurement at 280 nm and the amount of bacteriophage tail protein bound to the sepharose was calculated. 12.2 mg bacteriophage tail protein were bound per 1 ml sepharose.

Columns were cast with a volume of 1.5 ml. Moreover columns were cast with the same volume of T4p12 material and polymyxin B sepharose. Each one of these columns was equilibrated with running buffer (20 mM Hepes, 150 mM NaCl, 2 mM EDTA, pH 7.5) and afterwards the endotoxin removal from a BSA solution (1.2 mg/ml) charged with lipopolysaccharide of E. coli O55:B5 (approximately 1000 EU/ml) was determined. Therefore before the application of the sample, at first 1 ml running buffer was collected from each column (Miro2p12, T4p12, Polymyxin B) and afterwards each 1 ml BSA was applied and washed with running buffer. The flow-through was fractionated and the fractions were determined of protein (BSA) and endotoxin. The results are shown in FIG. 2. No endotoxin was able to be removed from the solution by T4p12, which requires free calcium for binding endotoxin. It was possible to reduce the endotoxin content about 96% by polymyxin B but only 67% of the applied BSA was recovered. It was possible to remove more than 99% of endotoxin by Miro2p12 and the recovery rate for BSA was 92% and was therefore significantly higher than for polymyxin B.

Similar experiments were carried out with PBS (10 mM $Na_2HPO_4$, 1.8 mM $KH_2PO_4$, 137 mM NaCl, 2.7 mM KCl, pH 7.4) and citrate (20 mM citrate, 150 mM NaCl, pH 7.0) as running buffers. Also in these buffers the endotoxin removal was strongly decreased by T4p12, because calcium was either precipitated (phosphate buffer) or complexed (citrate). The results are shown in the FIGS. 3 and 4 and show expectedly a low (PBS) and no endotoxin removal (citrate), respectively, by T4p12. It was possible to remove each time more than 96% of endotoxin by polymyxin B, but the BSA recovery was only between 60-80%. It was possible to remove more than 99% of endotoxin by Miro2p12 and the BSA recovery was higher than 90%. Moreover the suitability of N-Strep-Miro2p12 was determined for the endotoxin removal from serum. Therefore human serum was studded with lipopolysaccharide of E. coli O55:B5 and applied onto N-Strep-Miro2p12 sepharose columns (see FIG. 7). It was possible to remove approximately 90% of the applied endotoxin from human serum.

EXAMPLE 6

Detection of LPS by the Binding of T4p12 to Immobilized LPS

Bacteriophage tail protein Miro2p12 was immobilized to NHS-Sepharose (Amersham Pharmacia) (3.4 mg protein per 1 ml sepharose) and out of this 4 column were cast with a volume of 0.5 ml each. The columns were washed with each 3 ml sodium phosphate buffer (20 mM sodium phosphate, pH 12.0) and with each 3 ml regeneration buffer (20 mM Hepes, 150 mM NaCl, 2 mM EDTA, pH 7.5). Afterwards each 1 ml LPS of E. coli O55:B5 was applied onto two of these columns (0.1 mg/ml in Hepes buffer, $10^6$ EU/ml). The two other columns were rinsed with each 1 ml regeneration buffer. Following all columns were washed with each 3 ml equilibration buffer (20 mM Hepes, 150 mM NaCl, 0.1 mM $CaCl_2$, pH 7.5) and afterwards 1 ml of this buffer was applied again and collected as fraction 1. Following 0.5 ml of a solution with the bacteriophage tail proteins T4p12 (0.844 mg/ml in 20 mM Hepes, 150 mM NaCl, 0.1 mM $CaCl_2$) was applied onto the columns and washed with 2.5 ml equilibration buffer and 2 ml regeneration buffer. The flow-through was collected three times in fractions of 1 ml and once of 2 ml and the concentrations of the bacteriophage tail protein T4p12 was determined via absorption measurement at 280 nm in these fractions (FIG. 5). Most of the bacteriophage tail protein T4p12 was bound onto the columns, which was treated with LPS in advance and was able to be dissolved from these columns by the addition of regeneration buffer. In contrast to the columns not treated with LPS it flows through the columns without delay.

EXAMPLE 7

1. Construction of Aeh1 with N-terminal Strep-tag (N-Strep-Aeh1p12): The nucleotide sequence for the Strep-tag (U.S. Pat. No. 5,506,121) was inserted into the 5' end of Aeh1p12-Gens (NCBI Acc.Nr.AAQ17871) by PCR. Therefore a primer was designed for the 5' end of Aeh1 gene (5'-GAA GGA ACT AGT CAT ATG GCT AGC TGG AGC CAC CCG CAG TTC GAA AAA GGC GCC AGA ACA AAT AAT ATC ACA CAG 3'; SEQ ID NO:19), which comprises the nucleotide sequence of the Strep-tag at its 5' end (cursive in the sequence) and a restriction recognition site (NdeI, underlined in the sequence) in that way, that the gene can be used in the right reading frame in the expression plasmid. For the 3' end of Miro2p12 gene a primer was designed (5'-GAA GGA ACT AGT CAT ATG AGA ACA AAT AAT ATC ACA CAG 3'; SEQ ID NO:20), which inserts a BamHI restriction recognition site (underlined in the sequence) behind the Aeh1p12 gene. The PCR was carried out with 35 cycles (15 s 94° C., 15 s 51° C., 1 min 74° C.). The PCR preparation was restricted with NdeI and BamHI and the fragment of interest was inserted into the NdeI and BamHI site of the expressions plasmid pET21a after size fractionation by an agarose gel and elution from the gel. The sequence of Aeh1p12 gene was verified by DNA sequencing. Afterwards the plasmid pNS-Aeh1 was transformed into the expression strain HMS174 (DE 3).

2. Purification of N-Strep-Aeh1 protein: The E. coli strain HMS174 (DE 3) was raised with the plasmid pNS-Aeh1p12 in a 2 l agitation culture (LB-medium with ampicillin 100 µg/ml, kanamycin 25 µg/ml, rifampicin 10 µg/ml) until an OD600 of 0.5-0.7 at 37° C. and the expression of N-Strep-Aeh1p12 protein was induced by the addition of 1 mM IPTG (isopropyl-B-thiogalactopyranoside). After incubation at 37° C. for 4 h the cell were harvested. Harvested cells of 10 l culture were sustained into 50 ml 10 mM sodium phosphate, pH 8.0, 2 mM $MgCl_2$, 150 mM NaCl, disrupted in a microfluidizer (Microfluidics, M110L) and afterwards centrifuged for 30 min at 15.000 rpm (SS34). After washing for two times in the same buffer the N-Strep-Aeh1p12 protein was extracted from the pellet by stirring for 30 min in 50 mM sodium phosphate pH 12 and the preparation was centrifuged for 30 min at 15.000 rpm (SS34). The extraction was repeated once and the pooled supernatants with the released N-Strep-Aeh1p12 were dialysed against 100 mM Tris, 150 mM NaCl, pH 8.0. Afterwards the protein was further purified by a streptactin affinity column (5 ml, IBA GmbH, Göttingen, Germany). Therefore the streptactin affinity column was equilibrated with buffer "W" (100 mM TrisHCl pH 8, 1 mM EDTA, 150 mM NaCl) and Aeh1p12 was applied. After washing with 5 column volumes of buffer "W" it was eluted with 3 column volume buffer "W" with 2.5 mM desthiobiotin in buffer "W". After dialyse against 100 mM borate, 150 mM NaCl, pH 8 for several times, the concentration and purity of N-Strep-Aeh1p12 was examined. So approximately 20 mg N-Strep-Aeh1p12 were purified from 4 liter culture.

3. Coupling of Aeh1p12 to NHS activated sepharose. 22 ml N-Strep-Aeh1p12 (0.9 mg/ml in 100 mM borate, 150 mM NaCl, pH 8) were transferred with 200 µl NHS activated sepharose and incubated on a roller for 3 h at room temperature. Afterwards the sepharose was centrifuged (15 min, 3000 g) and washed with each 20 ml 100 mM Tris, 150 mM NaCl, pH 8 for three times. Following 0.5 ml aliquots of the wash fractions were dialysed against 100 mM Tris, 150 mM NaCl, pH 8 to remove the released NHS and the concentration of N-Strep-Aeh1p12 was determined in these aliquots by absorption measurement at 280 nm. The population density was calculated from the output protein amount and the protein amount in the wash fractions. It was possible to couple 2.5 mg N-Strep-Aeh1p12 per 1 ml sepharose.

4. Endotoxin removal by Aeh1p12 sepharose. A column with Aeh1p12 sepharose and a control column were cast, both with each a volume of 200 µA. The control column consisted of NHS sepharose, which was saturated with ethanol amine. Following both columns were washed with 2 ml 0.5% sodium deoxycholate, 15 ml pyrogene free water and 2 ml running buffer. Each 200 µA lipopolysaccharide of E. coli O55:B5, solved in the corresponding running buffer, was applied as sample. After the application of sample it was mixed with sepharose and incubated for 30 min at room temperature before the solution runs through the column. At first the columns were washed with 0.6 ml and following also with 1 ml running buffer twice. The flow-through was fractionated and the endotoxin concentration was determined in the application and the fractions via LAL test (kinetic chromogenic LAL-Test, Cambrex). This experiment was carried out with 2 different running buffers to examine the influence of calcium for the endotoxin removal. The running buffers were composed as following: buffer 1: 20 mM Hepes, 150 mM NaCl, 0.1 mM $CaCl_2$, pH 7.5. buffer 2: 20 mM Hepes, 150 mM NaCl, 2 mM EDTA, pH 7.5. As shown in FIG. 8, significantly more endotoxin is removed by the Aeh1p12 sepharose column (88% and 84%) as by the unloaded control column (25% and 39%). Calcium is irrelevant for the binding of endotoxin to Aeh1p12, because the endotoxin removal was in the presence of calcium similar (88%) to a buffer with a calcium chelator (84%).

EXAMPLE 8

1. Purification of N-Strep-Effe04p12. The E. coli strain HMS174 (DE 3) with the plasmid pNS-Effe04p12 was raised in 2 l shaking cultures (LB medium with ampicillin 100 µg/ml, rifampicin 10 µg/ml) until a OD600 of 0.5-0.7 at 37° C. and the expression of N-Strep-Effe04p12 protein was induced by the addition of 1 mM IPTG (isopropyl-B-thiogalactopyranoside). After incubation at 37° C. for 4 h the cells were harvested. Harvested cells from 6 l culture were sustained into 50 ml 100 mM Tris, 25 mM EDTA, 100 mM NaCl, pH 8.0, disrupted in a micro fluidizer (Microfluidics, M110L) and afterwards centrifuged for 30 min at 15.000 rpm (SS34). Following the N-Strep-Effe04p12 protein was extracted from the pellet by stirring for 2 h at 37° C. in 100 mM Tris, 1.5 M GdnHCl, pH 8.0, and the preparation was centrifuged for 30 min at 13.000 rpm (SS34). The extraction was repeated once. The pooled supernatants with the solved N-Strep-Effe04p12 were dialysed against 100 mM Tris, pH 8.0. Following the protein was further purified by a streptactin affinity column (5 ml, IBA GmbH, Gottingen, Germany). Therefore the streptactin affinity column was equilibrated with buffer "W" (100 mM TrisHCl pH 8, 1 mM EDTA, 150 mM NaCl) and N-Strep-Effe04p12 was applied. After washing with 5 column volumes with buffer "W", it was eluted with 3 column volume buffer "W" with 2.5 mM desthiobiotin in buffer "W". After dialyse against 100 mM borate, 150 mM NaCl, pH 8 for several times the concentration and purity of N-Strep-Effe04p12 was examined by SDS-PAGE and UV spectroscopy. So approximately 2 mg N-Strep-Effe04p12 were purified from 6 liter culture.

2. Coupling of N-Strep-Effe04p12 to NHS activated sepharose. 4 ml N-Strep-Effe04p12 (0.2 mg/ml in 100 mM borate, 150 mM NaCl, pH 8) were transferred with 100 µl NHS activated sepharose and incubated on a roller for 3 h at room temperature. Afterwards the sepharose was centrifuged (15 min, 3000 g) and washed with each 20 ml 100 mM Tris, 150 mM NaCl, pH 8 for three times. Following 0.5 ml aliquots of the wash fractions were dialysed against 100 mM Tris, 150 mM NaCl, pH 8 to remove the released NHS and the concentration of N-Strep-Aeh1p12 was determined in said aliquots by absorption measurement at 280 nm. The population density was calculated from the output protein amount and the protein amount in the wash fractions. It was possible to couple 3.6 mg N-Strep-Effe04p12 per 1 ml sepharose.

3. Endotoxin removal by N-Strep-Effe04p12 sepharose. 100 µl N-Strep-Effe04p12-sepharose was applied onto a mini-spin column (Handee Mini-Spin, Pierce) and at first washed with 1 ml endotoxin free running buffer (20 mM Hepes, 150 mM NaCl, 2 mM EDTA) for three times. Therefore the solution was separated from the sepharose by short centrifugation (400 g, 5 s). Afterwards 100 µl endotoxin solution (lipopolysaccharide of E. coli O55:B5 in running buffer) was incubated for 30 min with the sepharose before the solution was centrifuged and the sepharose was washed with 200 µl running buffer another two times. The endotoxin amounts were determined as well in the application (F0) as in the fractions after the sepharose by LAL test (kinetic chromogenic LAL test, Cambrex). As shown in FIG. 9, most of applied endotoxin is removed from the solution (endotoxin removal: 92%). Calcium is irrelevant for the binding of endotoxin to N-Strep-Effe04p12 because EDTA was contained in the running buffer.

EXAMPLE 9

Endotoxin Detection by the Binding of Miro2p12 to Immobilized LPS

Bacteriophage tail protein Miro2p12 was immobilized to NHS-Sepharose (Amersham Pharmacia) (5 mg protein per 1 ml sepharose) and out of this 4 column were cast with a volume of 1 ml each. Two of these were charged with LPS of E. coli O55:B5 ($10^6$ EU in 1 ml PLS buffer, 10 mM sodium phosphate, 70 mM NaCl, pH 7.4) (+ET, black bars FIG. 12), 2 were used as controls (-ET, white bars FIG. 12). 10 mM sodium phosphate, 80 mM NaCl, pH 7.4 was used as running buffer. Miro2p12 was applied onto all columns (each 600 µA of a solution with 0.1 mg/ml protein). The amount of applied and eluted Miro2p12, respectively, was determined by absorption at 280 nm. The amount of bacteriophage tail protein Miro2p12 was plotted against the fractions of the chromatography run, as illustrated in FIG. 12. Fraction 3 (F3) shows the flow-trough of Miro2p12 after the application (F0), so all bacteriophage tail protein, which is not retained by the column, fraction 4 (F4) is a wash fraction. After the washing regeneration buffer RB (10 mM sodium phosphate, 500 mM NaCl, pH 7.4) was added (see arrow direction), which dissolves Miro2p12 bound to endotoxin from the column again. Subsequent the fractions 5 and 6 were collected. Fraction F3 has a volume of 0.6 ml all other fractions have a volume of 1 ml. The application onto the column (F0) with the total amount of Miro2p12 is plotted as control. It can bee seen, that the columns, to which endotoxin was immobilized before, Miro2p12 was retained, while only a small amount of Miro2p12 was bound unspecifically to the control columns without endotoxin.

EXAMPLE 10

Endotoxin Detection Adsorbed to a PolySorp Microtiter Plate by the Binding of Miro2p12 Labeled with Biotin Production of Miro2p12 labeled with biotin. 2 ml of a Miro2p12 solution with a concentration of 2 mg/ml in a buffer with 50 mM sodium borate, 1.75 M GdmCl, pH 8.0 were transferred with 250 µl of a 10 mM Sulfo-NHS-LC-LC-biotin solution in water (Pierce) and incubated for 30 min at room temperature. Following the reaction solution is dialysed against buffer with 50 mM sodium borate, 1.75 M GdmCl, pH 8.0. The so obtained Miro2p12-bio was used for the following endotoxin detection, which is illustrated in FIG. 13. LPS of *E. coli* O55:B5 (3 µg/ml) was immobilised to PolySorp plates (Nunc) by adsorption (18 h at room temperature in PBS-Puffer, 10 mM $Na_2HPO_4$, 1.8 mM $KH_2PO_4$, 137 mM NaCl, 2.7 mM KCl, pH 7.4). Afterwards the microtiter plates were blocked with casein (0.05% in PBS, 1.5 h at RT) and washed with PBS buffer once. Control plates were not incubated with endotoxin but only blocked with casein. Each 200 µl Miro2p12 labeled with biotin (Miro2p12-bio) in 50 mM Tris, pH 8, 0.05% Casein, 0.05% Tween20 was added in raising concentration (white bars: plates without ET, black bars: plates with ET, protein concentration as specified). After 5 h incubation at room temperature it was washed with each 200 µl PBST (10 mM $Na_2HPO_4$, 1.8 mM $KH_2PO_4$, 137 mM NaCl, 2.7 mM KCl, 0.05% Tween, pH 7.4) for three times. The detection of Miro2p12 labeled with biotin and bound to endotoxin was carried out by a biotin specific ELISA. A conjugate of strepavidin with alkaline phosphatase (Amersham Biosciences) is diluted 1:5000 in PBST and each 200 µA of these are incubated with bound Miro2p12-bio for 1.5 h at room temperature. Afterwards they are washed with each 200 µA Tris-T (50 mM Tris, 0.05% Tween, pH 8.0) for three times. The colorimetric detection is carried out by absorption measurement at 405 nm after the addition of pNPP (para-nitrophenyl phosphate) in a concentration of 0.8 mg/ml as chromogenic substrate. Miro2p12 labeled with biotin binds in a concentration dependent form to the microtiter plates, which were coated with endotoxin beforehand.

EXAMPLE 11

Detection of FITC Labeled Endotoxin Bound to Immobilize Miro2p12

Miro2p12 (each 200 µl with 5 µg/ml protein) was adsorbed to a MaxiSorp plate (Nunc) (16 h at RT in PBS, 10 mM $Na_2HPO_4$, 1.8 mM $KH_2PO_4$, 137 mM NaCl, 2.7 mM KCl, pH 7.4). Afterwards the microtiter plates were blocked with casein (0.05% Casein in PBS, 1.5 h at RT, each 200 µl per well) and washed with PBS buffer once. Control plates were not incubated with Miro2p12, but only blocked with casein. Each 100 µl FITC labeled LPS of *E. coli* O55:B5 (Sigma) in PBS was added in raising concentration (white bars: plates without Miro2p12, black bars: plates with Miro2p12). It was washed with each 200 µl PBST (10 mM $Na_2HPO_4$, 1.8 mM $KH_2PO_4$, 137 mM NaCl, 2.7 mM KCl, 0.05% Tween, pH 7.4) for three times. The experiment is shown in FIG. 14. The detection of endotoxin bound to bacteriophage tail protein was carried out in a FITC specific ELISA. Anti-FITC antibodies (0.5 µg/ml, Zymed) are diluted 1:500 in PBST and afterwards each 200 µl were incubated with the FITC labeled endotoxin for 1 h at room temperature. Following it is washed with each 200 µl PBST for three times. As secondary antibody an anti-rabbit-IgG alkaline phosphatase conjugate is used (1 µg/ml, Pierce). It is applied in a dilution of 1:5000 and incubated for 1.5 h at room temperature. Afterwards it is washed with each 200 µl PBST for three times. The quantification is carried out by fluorescence measurement of the reaction products of a fluorescent alkaline phophatase substrate (methylumbelliferyl phosphate; Sigma) with 0.1 mg/ml methylumbelliferyl phosphate in 50 mM Tris, pH 8.0. Fluorescence labeled endotoxin binds in a concentration dependent form to the microtiter plates, which were coated with Miro2p12 beforehand.

The invention claimed is

1. A method for removing an endotoxin from a sample, comprising the steps:
   a) contacting a bacteriophage tail protein with a sample, wherein the bacteriophage tail protein binds said endotoxin independent of bivalent positive ion concentrations; and subsequently
   b) separating the endotoxin-bacteriophage tail protein complex from the sample,
   wherein the bacteriophage tail protein is selected from the group consisting of SEQ ID NOs: 2, 4, 6, 8, 10, 12 and 14.

2. The method according to claim 1, wherein steps a) and b) comprise column chromatography.

3. The method of claim 1, wherein bacteriophage tail proteins are directedly immobilized to a solid carrier.

4. The method according to claim 3, wherein the solid carrier is cellulose, filtration media, glass particles, magnetic particles, centrifugation or sedimentation substances or packing material for chromatography columns.

5. The method of claim 3, wherein the bacteriophage tail protein is immobilized to the solid carrier by coupling groups.

6. The method according to claim 3, wherein the bacteriophage tail protein is covalently immobilized to the solid carrier by chemical bonds.

7. The method according to claim 1, wherein the bacteriophage tail protein comprises a Strep-tag or a His-tag.

8. The method according to claim 1, wherein the bacteriophage tail protein is a short bacteriophage tail protein.

9. The method according to claim 1, wherein the bacteriophage tail protein comes from the Myoviridae family.

10. The method according to claim 1, wherein the bacteriophage tail protein is selected from the group consisting of pseudo-T-even, schizo-T-even and T-even phage.

11. The method according to claim 1, wherein the bacteriophage tail protein binds 2-keto-3-deoxyoctonic acid in the core region of the endotoxin.

12. The method according to claim 1, wherein the concentration of free unbound bivalent positive ions is less than 0.1 µM.

13. The method according to claim 1, wherein the bivalent positive ions are $Ca^{2+}$ and/or $Mg^{2+}$.

14. An isolated polypeptide comprising SEQ ID NO: 2, 4, 6, 8, 10, 12 or 14.

15. A method for the detection of endotoxin comprising the steps:
   a) contacting an endotoxin-containing sample with a surface; subsequently
   b) incubating a bacteriophage tail protein with an endotoxin immobilized to the surface, wherein the bacteriophage tail protein binds endotoxin independent of bivalent positive ion concentration; subsequently
   c) removing the unbound bacteriophage tail protein; and subsequently
   d) detecting the unbound bacteriophage tail protein of step c),
   wherein the bacteriophage tail protein is selected from the group consisting of SEQ ID NOs: 2, 4, 6, 8, 10, 12 and 14.

16. The method according to claim 15, further comprising the additional step after step a) and before step b) of removing the sample from the surface.

17. The method according to claim 15, wherein the surface is coated with an endotoxin-binding ligand by adsorption or covalent coupling.

18. The method according to claim 17, wherein the endotoxin binding ligand is a bacteriophage tail protein that binds endotoxin independent of the bivalent positive ion concentration.

19. A method for the detection of endotoxin comprising the steps:
   a) contacting an endotoxin-containing sample to a surface immobilized with a first bacteriophage tail protein that binds endotoxin independent of bivalent positive ion concentration; subsequently
   b) removing the sample from the surface; subsequently
   c) incubating of a second bacteriophage tail with the endotoxin bound to the first bacteriophage tail protein, wherein the second bacteriophage tail protein binds endotoxin only in the presence of bivalent positive ions; subsequently removing unbound second bacteriophage tail protein; and subsequently
   d) detecting the second bacteriophage tail protein bound to endotoxin,
   wherein the bacteriophage tail protein is selected from the group consisting of SEQ ID NOs: 2, 4, 6, 8, 10, 12 and 14.

20. A method for the detection of endotoxin comprising the steps:
   a) contacting an endotoxin-containing sample to a surface immobilized with a bacteriophage tail protein that binds endotoxin independent of bivalent positive ion concentration; subsequently
   b) removing the sample from the surface; and subsequently
   c) detecting the endotoxin bound in step a),
   wherein the bacteriophage tail protein is selected from the group consisting of SEQ ID NOs: 2, 4, 6, 8, 10, 12 and 14.

21. The method according to claim 15, wherein detecting is carried out by spectroscopic methods, ELISA, chemical or enzymatic detection reaction of endotoxin or separated endotoxin components or by capacity measurement.

22. A method for the detection of endotoxin comprising the steps:
   a) mixing a sample with an endotoxin coupled to a marker; subsequently
   b) applying the mixture of step a) to a surface with an immobilized bacteriophage tail protein, wherein the bacteriophage tail protein binds endotoxin independent of bivalent positive ion concentration; subsequently
   c) removing the mixture from the surface; subsequently
   d) washing the surface; and subsequently
   e) detecting labeled endotoxin on the surface and/or free labeled endotoxin of the pooled samples after steps c) and d),
   wherein the bacteriophage tail protein is selected from the group consisting of SEQ ID NOs: 2, 4, 6, 8, 10, 12 and 14.

* * * * *

SEQUENCE LISTING

```
<160> NUMBER OF SEQ ID NOS: 32

<210> SEQ ID NO 1
<211> LENGTH: 54
<212> TYPE: DNA
<213> ORGANISM: Bacteriophage Miro1

<400> SEQUENCE: 1
acgcgcaaag cttgtcgacg gatcctatca ttctttacc ttaattatgt agtt            54

<210> SEQ ID NO 2
<211> LENGTH: 457
<212> TYPE: PRT
<213> ORGANISM: Bacteriophage Miro1

<400> SEQUENCE: 2

Met Leu Glu Pro Pro Ala Val Glu Lys Gly Ala Ala Gln Asn Asn Tyr
1               5                   10                  15

Asn His Tyr Ser Asp Leu Ala Lys Tyr Thr Ile Phe Asp Pro Thr Asn
            20                  25                  30
```

-continued

```
Thr Gln Trp Pro Val Ala Ile Lys Asp Val Gln Ser Ala Leu Glu Leu
     35                  40                  45
Ile Gly Ser Trp Ala Arg Thr Asp Thr Gly Leu Pro Val Ala Ser Pro
 50                  55                  60
Thr Val Ala Gly Val Ile Arg Thr Ala Thr Gln Ala Glu Val Asp Ala
 65                  70                  75                  80
Gly Thr Ile Gly Asn Ala Ala Val Thr Pro Ala Thr Leu Lys Ser Thr
                 85                  90                  95
Val Thr Arg Pro Glu Ala Thr Ala Val Leu Gly Leu Thr Arg Tyr
                100                 105                 110
Ala Thr Asn Thr Glu Ala Ala Leu Thr Ala Gly Asn Arg Thr Ile
            115                 120                 125
Thr Ala Ala Leu Gly His Val Phe Lys Thr Val Lys Ala Gln Glu
130                 135                 140
Asn Val Asp Gly Thr Val Arg Leu Thr Thr Ala Ala Gln Ala Gln Ala
145                 150                 155                 160
Gly Thr Asp Glu Thr Ala Val Thr Pro Lys Arg Val Val Glu Met Ile
                165                 170                 175
Gly Lys Phe Ser Val Ser Pro Pro Ser Tyr Thr Ser Ala Thr Glu Ser
            180                 185                 190
Asn Leu Gly Leu Val Arg Val Ala Thr Gln Ala Gln Val Ala Ala Gly
            195                 200                 205
Ala Val His Asp Gly Tyr Ala Val Thr Pro Lys Thr Phe Met Ala Ser
210                 215                 220
Lys Ala Ser Asp Ser Val Phe Gly Ile Val Lys Phe Ala Lys Asp Ser
225                 230                 235                 240
Asp Val Ala Ser Ala Thr Ser Asn Asn Leu Ala Val Thr Pro Lys Ser
                245                 250                 255
Leu Gln Ala Leu Lys Ser Thr Lys Asp Lys Tyr Gly Leu Thr Arg Leu
            260                 265                 270
Ser Gly Ser Pro Thr Thr Asp Ala Ser Leu Ala Ala Ala Ala Thr Asp
            275                 280                 285
Ala Val Phe Lys Thr Arg Lys Ile Asn Gly Lys Thr Leu Asp Asn Asp
            290                 295                 300
Ile Thr Ile Thr Asn Asn Asp Ile Asn Cys Tyr Thr Arg Gln Glu Ser
305                 310                 315                 320
Asp Gly Arg Tyr Met Pro Ala Gly Thr Arg Val Gly Asn Val Thr Trp
                325                 330                 335
Val Glu Gly Gln Ser Trp Ile Ser Arg Gly Ala Thr Phe Thr Cys Asn
            340                 345                 350
Ala Pro Trp Glu Ala Ser Ser Arg Leu Ala Leu Asn Val Asn Val Lys
            355                 360                 365
Phe Glu Arg Asn Asn Asp Gly Tyr Asp Asn Arg Ile Phe Arg Phe Val
            370                 375                 380
Val Ile Val Asn Gly Ser Gln Trp Gly Gly Glu Leu Thr Leu Asn Ile
385                 390                 395                 400
Glu Asn Thr Lys Gly Gly Arg Asn Gly His Ser Trp Arg Phe Glu Ala
                405                 410                 415
Tyr Ala Ser Ser Asn Phe Phe Phe Asn Asn Ile Pro Pro Asn Ala Thr
            420                 425                 430
Val Gln Ile Arg Pro Thr Glu Asp Ser Arg Ile Ile Phe Tyr Asp Cys
            435                 440                 445
Met Leu Thr Phe Cys Thr Asn Arg Pro
450                 455
```

<210> SEQ ID NO 3
<211> LENGTH: 1347
<212> TYPE: DNA
<213> ORGANISM: Bacteriophage Miro2

<400> SEQUENCE: 3

```
atggcccaga ataactataa tcactacagt gatttggcca aatatacgat atttgaccca     60
acaaatacac aatggcctgt tgctataaaa gacgtccaat cagcgttaga gctgattggt    120
agctgggcaa gaactgatac cggattacct gtagcatctc ctacagtagc cggtgtaatt    180
cgcacagcaa cacaggctga agttgatgct ggaactattg gtaatgctgc ggtaactcct    240
gctacattaa atccacagt tacccgtcct gaagcaacta cagcagttct tggcttaaca    300
cggtatgcta ctaatactga agccgcagca ttaaccgcag gaaatagaac tattaccgcg    360
gcggctctcg tcatgtgtt taaaactgtg aaagcccaag aaaacgtaga tggaactgtt    420
aggttaacta ctgcggctca agcacaagca ggaactgacg aaactaccgc agtaactcct    480
aagcgtgttg tagaaatgat tggaaagttc agtgtcagtc ctcctagtta tacctctgcg    540
acagaaagca acttgggatt agttcgtgtc gcaacccaag cccaggtagc agcaggtgct    600
gttcacgatg gatacgcagt aactccaaaa accttcatgg catcaaaagc gtctgacagc    660
gtatttggta tagtaaaatt tgctaaagac tcagatgtgg cttcagctac ttctaacaat    720
ttggctgtta ctccaaaaag tcttcaagcg ctaaaatcca ccaaggataa atatggatta    780
accagattat caggttctcc aactactgat gcttcattgg cagcggctgc aacagatgca    840
gtctttaaaa cccgtagaat aaacggaaaa actcttgata tgacataac aattactaat    900
aatgatatta ttgttatac aagacaagaa tctgacgggc gttacatgcc agctggaacc    960
agagtaggta atgttacttg ggttgaagga caatcttgga ttagtcgagg tgcaacgttt   1020
acatgtaatg caccatggga agcttctagt agattagctc taaacgttaa tgtaaaattt   1080
gagcgtaaca acgacggata tgacaatcgt attttcagat tgttgtaat agttaacggt   1140
tcccaatggg gaggtgaact tactcttaac atcgaaaata ctaaaggcgg acgaaatggt   1200
cattcatgga gatttgaagc ttacgcatct agcaactttt tcttcaataa cattcctcca   1260
aatgccactg ttcaaataag accaacagaa gacagtcgta ttatatttta tgactgcatg   1320
cttacattct gtacaaatag accgtaa                                       1347
```

<210> SEQ ID NO 4
<211> LENGTH: 448
<212> TYPE: PRT
<213> ORGANISM: Bacteriophage Miro2

<400> SEQUENCE: 4

```
Met Ala Gln Asn Asn Tyr Asn His Tyr Ser Asp Leu Ala Lys Tyr Thr
1               5                   10                  15

Ile Phe Asp Pro Thr Asn Thr Gln Trp Pro Val Ala Ile Lys Asp Val
            20                  25                  30

Gln Ser Ala Leu Glu Leu Ile Gly Ser Trp Ala Arg Thr Asp Thr Gly
        35                  40                  45

Leu Pro Val Ala Ser Pro Thr Val Ala Gly Val Ile Arg Thr Ala Thr
    50                  55                  60

Gln Ala Glu Val Asp Ala Gly Thr Ile Gly Asn Ala Ala Val Thr Pro
65                  70                  75                  80

Ala Thr Leu Lys Ser Thr Val Thr Arg Pro Glu Ala Thr Thr Ala Val
                85                  90                  95
```

Leu Gly Leu Thr Arg Tyr Ala Thr Asn Thr Glu Ala Ala Ala Leu Thr
            100                 105                 110

Ala Gly Asn Arg Thr Ile Thr Ala Ala Ala Leu Gly His Val Phe Lys
        115                 120                 125

Thr Val Lys Ala Gln Glu Asn Val Asp Gly Thr Val Arg Leu Thr Thr
130                 135                 140

Ala Ala Gln Ala Gln Ala Gly Thr Asp Glu Thr Thr Ala Val Thr Pro
145                 150                 155                 160

Lys Arg Val Val Glu Met Ile Gly Lys Phe Ser Val Ser Pro Pro Ser
                165                 170                 175

Tyr Thr Ser Ala Thr Glu Ser Asn Leu Gly Leu Val Arg Val Ala Thr
            180                 185                 190

Gln Ala Gln Val Ala Ala Gly Ala Val His Asp Gly Tyr Ala Val Thr
        195                 200                 205

Pro Lys Thr Phe Met Ala Ser Lys Ala Ser Asp Ser Val Phe Gly Ile
    210                 215                 220

Val Lys Phe Ala Lys Asp Ser Asp Val Ala Ser Ala Thr Ser Asn Asn
225                 230                 235                 240

Leu Ala Val Thr Pro Lys Ser Leu Gln Ala Leu Lys Ser Thr Lys Asp
                245                 250                 255

Lys Tyr Gly Leu Thr Arg Leu Ser Gly Ser Pro Thr Thr Asp Ala Ser
            260                 265                 270

Leu Ala Ala Ala Ala Thr Asp Ala Val Phe Lys Thr Arg Arg Ile Asn
        275                 280                 285

Gly Lys Thr Leu Asp Asn Asp Ile Thr Ile Thr Asn Asn Asp Ile Asn
    290                 295                 300

Cys Tyr Thr Arg Gln Glu Ser Asp Gly Arg Tyr Met Pro Ala Gly Thr
305                 310                 315                 320

Arg Val Gly Asn Val Thr Trp Val Glu Gly Gln Ser Trp Ile Ser Arg
                325                 330                 335

Gly Ala Thr Phe Thr Cys Asn Ala Pro Trp Glu Ala Ser Ser Arg Leu
            340                 345                 350

Ala Leu Asn Val Asn Val Lys Phe Glu Arg Asn Asn Asp Gly Tyr Asp
        355                 360                 365

Asn Arg Ile Phe Arg Phe Val Val Ile Val Asn Gly Ser Gln Trp Gly
    370                 375                 380

Gly Glu Leu Thr Leu Asn Ile Glu Asn Thr Lys Gly Gly Arg Asn Gly
385                 390                 395                 400

His Ser Trp Arg Phe Glu Ala Tyr Ala Ser Ser Asn Phe Phe Phe Asn
                405                 410                 415

Asn Ile Pro Pro Asn Ala Thr Val Gln Ile Arg Pro Thr Glu Asp Ser
            420                 425                 430

Arg Ile Ile Phe Tyr Asp Cys Met Leu Thr Phe Cys Thr Asn Arg Pro
        435                 440                 445

<210> SEQ ID NO 5
<211> LENGTH: 1386
<212> TYPE: DNA
<213> ORGANISM: Bacteriophage Effe04

<400> SEQUENCE: 5
atgagtaaca atacaatcaa ccacgtaagt gataaatcca tttacgtgac atttgaccca      60
acaggtactg attggcctga taccataacc aacgtacaag atgcgttgga aaaaataggt     120
agttgggcgc gtactgatac tgggcttcct atcgcaacaa cttctgttcg tggtattgct     180

```
cagatcgcaa ccgaagctga tattaacgct ggcacggata acactaagat tgttactccg        240
aaactgttag cataccgtat gcagaaccct aaagcatcac aaaccgtatg gggttatacg        300
aagtattcga ctgatgcgga atctacaacc gtaactaacg atgcatcgtc tattactccg        360
cgatcgctga actatgtgtt caataaccgc aaaggtacag aatcggtttg gggttcttct        420
aaaatcgcta ccactgcaca ggcggttgct ggtacagata acactgtaac tatgactccg        480
cttaaagtca agcaagcgat cgcgtctctg gttcctgttc agtcaagtgc gaccgaaagc        540
tcgcaaggtc tggtacaact ggcaacagtt gcacaggttc aggctggtac gatccgtgaa        600
gggtatgcaa tttcaccttta tacgtttatt cgtttaactg caactgaaag caacctgggc        660
gttattcgta tcgcatcaca ggcagaagca aacgcaggta ctgatgacac caaagcgatt        720
actgcgaaaa aattaatcaa tacccgtgca actggttccc agttcggtgt tgtcaaatta        780
gcaacaactg ttggttatgt ggcaaacacc gcactttctt ctaatgctta tgtattgcct        840
agcgatcgta gtgcggtaat taatggttct ctttatgaga atagcgcaat acataacaac        900
aaatatcaga cgtggacaga tcttgattgg catttcccag taggtgctat tgtcatgact        960
ggtttccaga ctgaccacgg tagttttgtat atttgtgatg acgttcact gaataaaaat       1020 aattacccgt tactgtttga gcgtataggt tatacatttg gtggtggcgg tgattggttt       1080
aacattccag actgtcgagg cgttgcagta cgtggtcatg accgtgggcg tggactaaac       1140
cctaatcgtg ggtatggtac atatgaagga gatatgttgg gatggcacga cacccatta        1200 caacttatct accagaacgg cggtaacatt ccgaaatggc aagcagttta cgaactgaaa       1260
agcgccgaga agaatgacca aagcgctcgc gtatttgatg cttctataac taaagctact       1320
ggtgtgggcg gtgaagaaac ccgcatgaaa aatatcgcat taaactacgt aattcgcgta       1380
ttataa                                                                 1386
```

<210> SEQ ID NO 6
<211> LENGTH: 475
<212> TYPE: PRT
<213> ORGANISM: Bacteriophage Effe04

<400> SEQUENCE: 6

```
Met Ala Ser Ala Ser Trp Ser His Pro Gln Phe Glu Lys Gly Ala Ser
1               5                   10                  15

Asn Asn Thr Ile Asn His Val Ser Asp Lys Ser Ile Tyr Val Thr Phe
            20                  25                  30

Asp Pro Thr Gly Thr Asp Trp Pro Asp Thr Ile Thr Asn Val Gln Asp
        35                  40                  45

Ala Leu Glu Lys Ile Gly Ser Trp Ala Arg Thr Asp Thr Gly Leu Pro
    50                  55                  60

Ile Ala Thr Thr Ser Val Arg Gly Ile Ala Gln Ile Ala Thr Glu Ala
65                  70                  75                  80

Asp Ile Asn Ala Gly Thr Asp Asn Thr Lys Ile Val Thr Pro Lys Leu
                85                  90                  95

Leu Ala Tyr Arg Met Gln Asn Pro Lys Ala Ser Gln Thr Val Trp Gly
            100                 105                 110

Tyr Thr Lys Tyr Ser Thr Asp Ala Glu Ser Thr Thr Val Thr Asn Asp
        115                 120                 125

Ala Ser Ser Ile Thr Pro Arg Ser Leu Asn Tyr Val Phe Asn Asn Arg
    130                 135                 140

Lys Gly Thr Glu Ser Val Trp Gly Ser Ser Lys Ile Ala Thr Thr Ala
145                 150                 155                 160
```

```
Gln Ala Val Ala Gly Thr Asp Asn Thr Val Thr Met Thr Pro Leu Lys
                165                 170                 175
Val Lys Gln Ala Ile Ala Ser Leu Val Pro Val Gln Ser Ser Ala Thr
            180                 185                 190
Glu Ser Ser Gln Gly Leu Val Gln Leu Ala Thr Val Ala Gln Val Gln
        195                 200                 205
Ala Gly Thr Ile Arg Glu Gly Tyr Ala Ile Ser Pro Tyr Thr Phe Ile
    210                 215                 220
Arg Leu Thr Ala Thr Glu Ser Asn Leu Gly Val Ile Arg Ile Ala Ser
225                 230                 235                 240
Gln Thr Glu Ala Asn Ala Gly Thr Asp Asp Thr Lys Ala Ile Thr Ala
                245                 250                 255
Lys Lys Leu Ile Asn Thr Arg Ala Thr Gly Ser Gln Phe Gly Val Val
            260                 265                 270
Lys Leu Ala Thr Thr Val Gly Tyr Val Ala Asn Thr Ala Leu Ser Ser
        275                 280                 285
Asn Ala Tyr Val Leu Pro Ser Asp Arg Ser Ala Val Ile Asn Gly Ser
    290                 295                 300
Leu Tyr Glu Tyr Ser Ala Ile His Asn Asn Lys Tyr Gln Thr Trp Thr
305                 310                 315                 320
Asp Leu Asp Trp His Phe Pro Val Gly Ala Ile Val Met Thr Gly Phe
                325                 330                 335
Gln Thr Asp His Gly Ser Leu Tyr Ile Cys Asp Gly Arg Ser Leu Asn
            340                 345                 350
Lys Asn Asn Tyr Pro Leu Leu Phe Glu Arg Ile Gly Tyr Thr Phe Gly
        355                 360                 365
Gly Gly Gly Asp Trp Phe Asn Ile Pro Asp Cys Arg Gly Val Ala Val
    370                 375                 380
Arg Gly His Asp Arg Gly Arg Gly Leu Asn Pro Asn Arg Gly Tyr Gly
385                 390                 395                 400
Thr Tyr Glu Gly Asp Met Leu Gly Trp His Glu His Pro Leu Gln Leu
                405                 410                 415
Ile Tyr Gln Asn Gly Gly Asn Ile Pro Lys Trp Gln Ala Val Tyr Glu
            420                 425                 430
Leu Lys Ser Ala Glu Lys Asn Asp Gln Ser Ala Arg Val Phe Asp Ala
        435                 440                 445
Ser Ile Thr Lys Ala Thr Gly Val Gly Gly Glu Glu Thr Arg Met Lys
    450                 455                 460
Asn Ile Ala Leu Asn Tyr Val Ile Arg Val Leu
465                 470                 475

<210> SEQ ID NO 7
<211> LENGTH: 1383
<212> TYPE: DNA
<213> ORGANISM: Artificial Sequence
<220> FEATURE:
<223> OTHER INFORMATION: N-Strep Miro1p12

<400> SEQUENCE: 7
atggctagct ggagccaccc gcagttcgaa aaaggcgccg cccagaataa ctataatcac      60
tacagtgatt tggccaaata tacgatattt gacccaacaa atacacaatg gcctgttgct     120
ataaaagacg tccaatcagc gttagagctg attggcagct gggcaagaac tgataccgga     180
ttacccgtag catctcctac agtagccggt gtaattcgca cagcaacaca ggctgaagtt     240
gatgctggaa ctattggtaa tgctgcggta actcctgcta cattaaaatc cacagttacc     300
```

```
cgtcctgaag caactacagc agttcttggc ttaacacggt atgctactaa tactgaagct    360
gcagcattaa ccgcaggaaa tagaactatt accgcggcgg ctctcggtca tgtgtttaaa    420
actgtgaaag cccaagaaaa cgtagatgga actgttaggt taactactgc ggctcaagca    480
caagcaggaa ctgacgaaac taccgcagta actcctaagc gtgttgtaga aatgattgga    540
aagttcagcg ttagtcctcc tagttatacc tctgcaacag aaagcaactt gggattagtt    600
cgtgtcgcaa cccaagccca ggtagcagca ggtgccgttc acgacggata cgcagtaact    660
ccaaaaacct tcatggcatc aaaagcgtct gacagtgtat ttggtatagt aaatttgct    720
aaagactcag atgtggcttc agctacttct aacaatttgg ctgttactcc aaaaagtctt    780
caagcgctaa atccaccaa ggataaatat ggattaacca gattatcagg ttctccaact    840
actgatgctt cactggcagc tgcggcaaca gatgctgttt taaaacccg taaaataaac    900
ggaaaaactc ttgacaatga cataacgatt actaacaatg atattaattg ttatacaagg    960
caagaatctg acgggcgtta catgccagct ggaactagag taggtaatgt tacttgggtt   1020
gaaggacaat cttggattag tcgaggtgca acgtttacat gtaatgcacc atgggaagct   1080
tctagtagat tagctctaaa tgttaatgta aaatttgagc gtaacaacga cggatatgac   1140
aatcgtattt tcagatttgt tgtaatagtt aacggttccc aatggggcgg tgaacttact   1200
cttaacatcg aaaatactaa aggcggacga aatggtcatt catggagatt tgaagcttac   1260
gcatctagca acttttctt caataacatt cctccaaatg ccactgttca ataagacca   1320
acagaagaca gtcgtattat attttatgac tgcatgctta cattctgtac aaatagaccg   1380
taa                                                                  1383

<210> SEQ ID NO 8
<211> LENGTH: 460
<212> TYPE: PRT
<213> ORGANISM: Artificial Sequence
<220> FEATURE:
<223> OTHER INFORMATION: N-Strep Mirolp12

<400> SEQUENCE: 8

Met Ala Ser Trp Ser His Pro Gln Phe Glu Lys Gly Ala Ala Gln Asn
1               5                   10                  15

Asn Tyr Asn His Tyr Ser Asp Leu Ala Lys Tyr Thr Ile Phe Asp Pro
            20                  25                  30

Thr Asn Thr Gln Trp Pro Val Ala Ile Lys Asp Val Gln Ser Ala Leu
        35                  40                  45

Glu Leu Ile Gly Ser Trp Ala Arg Thr Asp Thr Gly Leu Pro Val Ala
    50                  55                  60

Ser Pro Thr Val Ala Gly Val Ile Arg Thr Ala Thr Gln Ala Glu Val
65                  70                  75                  80

Asp Ala Gly Thr Ile Gly Asn Ala Ala Val Thr Pro Ala Thr Leu Lys
                85                  90                  95

Ser Thr Val Thr Arg Pro Glu Ala Thr Thr Ala Val Leu Gly Leu Thr
            100                 105                 110

Arg Tyr Ala Thr Asn Thr Glu Ala Ala Ala Leu Thr Ala Gly Asn Arg
        115                 120                 125

Thr Ile Thr Ala Ala Ala Leu Gly His Val Phe Lys Thr Val Lys Ala
    130                 135                 140

Gln Glu Asn Val Asp Gly Thr Val Arg Leu Thr Thr Ala Ala Gln Ala
145                 150                 155                 160

Gln Ala Gly Thr Asp Glu Thr Thr Ala Val Thr Pro Lys Arg Val Val
```

```
                       165                 170                 175
Glu Met Ile Gly Lys Phe Ser Val Ser Pro Ser Tyr Thr Ser Ala
                180                 185                 190

Thr Glu Ser Asn Leu Gly Leu Val Arg Val Ala Thr Gln Ala Gln Val
            195                 200                 205

Ala Ala Gly Ala Val His Asp Gly Tyr Ala Val Thr Pro Lys Thr Phe
        210                 215                 220

Met Ala Ser Lys Ala Ser Asp Ser Val Phe Gly Ile Val Lys Phe Ala
225                 230                 235                 240

Lys Asp Ser Asp Val Ala Ser Ala Thr Ser Asn Asn Leu Ala Val Thr
                245                 250                 255

Pro Lys Ser Leu Gln Ala Leu Lys Ser Thr Lys Asp Lys Tyr Gly Leu
            260                 265                 270

Thr Arg Leu Ser Gly Ser Pro Thr Thr Asp Ala Ser Leu Ala Ala Ala
        275                 280                 285

Ala Thr Asp Ala Val Phe Lys Thr Arg Lys Ile Asn Gly Lys Thr Leu
        290                 295                 300

Asp Asn Asp Ile Thr Ile Thr Asn Asn Asp Ile Asn Cys Tyr Thr Arg
305                 310                 315                 320

Gln Glu Ser Asp Gly Arg Tyr Met Pro Ala Gly Thr Arg Val Gly Asn
                325                 330                 335

Val Thr Trp Val Glu Gly Gln Ser Trp Ile Ser Arg Gly Ala Thr Phe
            340                 345                 350

Thr Cys Asn Ala Pro Trp Glu Ala Ser Ser Arg Leu Ala Leu Asn Val
        355                 360                 365

Asn Val Lys Phe Glu Arg Asn Asn Asp Gly Tyr Asp Asn Arg Ile Phe
        370                 375                 380

Arg Phe Val Val Ile Val Asn Gly Ser Gln Trp Gly Gly Glu Leu Thr
385                 390                 395                 400

Leu Asn Ile Glu Asn Thr Lys Gly Gly Arg Asn Gly His Ser Trp Arg
                405                 410                 415

Phe Glu Ala Tyr Ala Ser Ser Asn Phe Phe Phe Asn Asn Ile Pro Pro
            420                 425                 430

Asn Ala Thr Val Gln Ile Arg Pro Thr Glu Asp Ser Arg Ile Ile Phe
        435                 440                 445

Tyr Asp Cys Met Leu Thr Phe Cys Thr Asn Arg Pro
    450                 455                 460

<210> SEQ ID NO 9
<211> LENGTH: 1383
<212> TYPE: DNA
<213> ORGANISM: Artificial Sequence
<220> FEATURE:
<223> OTHER INFORMATION: N-Strep Miro2p12

<400> SEQUENCE: 9
atggctagct ggagccaccc gcagttcgaa aaaggcgccg cccagaataa ctataatcac    60
tacagtgatt tggccaaata tacgatattt gacccaacaa atacacaatg gcctgttgct   120
ataaaagacg tccaatcagc gttagagctg attggtagct gggcaagaac tgataccgga   180
ttacctgtag catctcctac agtagccggt gtaattcgca cagcaacaca ggctgaagtt   240
gatgctggaa ctattggtaa tgctgcggta actcctgcta cattaaaatc cacagttacc   300
cgtcctgaag caactacagc agttcttggc ttaacgggt atgctactaa tactgaagcc   360
gcagcattaa ccgcaggaaa tagaactatt accgcggcgg ctctcggtca tgtgtttaaa   420
```

-continued

```
actgtgaaag cccaagaaaa cgtagatgga actgttaggt taactactgc ggctcaagca    480
caagcaggaa ctgacgaaac taccgcagta actcctaagc gtgttgtaga atgattgga     540
aagttcagtg tcagtcctcc tagttatacc tctgcgacag aaagcaactt gggattagtt    600
cgtgtcgcaa cccaagccca ggtagcagca ggtgctgttc acgatggata cgcagtaact    660
ccaaaaacct tcatggcatc aaaagcgtct gacagcgtat ttggtatagt aaaatttgct    720
aaagactcag atgtgccttc agctacttct aacaatttgg ctgttactcc aaaaagtctt    780
caagcgctaa atccaccaa ggataaatat ggattaacca gattatcagg ttctccaact     840
actgatgctt cattgcagc ggctgcaaca gatgcagtct ttaaaacccg tagaataaac     900
ggaaaaactc ttgataatga cataacaatt actaataatg atattaattg ttatacaaga    960
caagaatctg acgggcgtta catgccagct ggaaccagag taggtaatgt tacttgggtt   1020
gaaggacaat cttggattag tcgaggtgca acgtttacat gtaatgcacc atgggaagct   1080
tctagtagat tagctctaaa cgttaatgta aaatttgagc gtaacaacga cggatatgac   1140
aatcgtattt tcagatttgt tgtaatagtt aacggttccc aatggggagg tgaacttact   1200
cttaacatcg aaaatactaa aggcggacga atggtcatt catggagatt tgaagcttac    1260
gcatctagca acttttttctt caataacatt cctccaaatg ccactgttca aataagacca   1320
acagaagaca gtcgtattat attttatgac tgcatgctta cattctgtac aaatagaccg   1380
taa                                                                 1383
```

<210> SEQ ID NO 10
<211> LENGTH: 460
<212> TYPE: PRT
<213> ORGANISM: Artificial Sequence
<220> FEATURE:
<223> OTHER INFORMATION: N-Strep Miro2p12

<400> SEQUENCE: 10

```
Met Ala Ser Trp Ser His Pro Gln Phe Glu Lys Gly Ala Ala Gln Asn
1               5                   10                  15

Asn Tyr Asn His Tyr Ser Asp Leu Ala Lys Tyr Thr Ile Phe Asp Pro
            20                  25                  30

Thr Asn Thr Gln Trp Pro Val Ala Ile Lys Asp Val Gln Ser Ala Leu
        35                  40                  45

Glu Leu Ile Gly Ser Trp Ala Arg Thr Asp Thr Gly Leu Pro Val Ala
    50                  55                  60

Ser Pro Thr Val Ala Gly Val Ile Arg Thr Thr Gln Ala Glu Val
65                  70                  75                  80

Asp Ala Gly Thr Ile Gly Asn Ala Ala Val Thr Pro Ala Thr Leu Lys
                85                  90                  95

Ser Thr Val Thr Arg Pro Glu Ala Thr Thr Ala Val Leu Gly Leu Thr
            100                 105                 110

Arg Tyr Ala Thr Asn Thr Glu Ala Ala Ala Leu Thr Ala Gly Asn Arg
        115                 120                 125

Thr Ile Thr Ala Ala Ala Leu Gly His Val Phe Lys Thr Val Lys Ala
    130                 135                 140

Gln Glu Asn Val Asp Gly Thr Val Arg Leu Thr Thr Ala Ala Gln Ala
145                 150                 155                 160

Gln Ala Gly Thr Asp Glu Thr Thr Ala Val Thr Pro Lys Arg Val Val
                165                 170                 175

Glu Met Ile Gly Lys Phe Ser Val Ser Pro Pro Ser Tyr Thr Ser Ala
            180                 185                 190
```

Thr Glu Ser Asn Leu Gly Leu Val Arg Val Ala Thr Gln Ala Gln Val
    195                 200                 205

Ala Ala Gly Ala Val His Asp Gly Tyr Ala Val Thr Pro Lys Thr Phe
    210                 215                 220

Met Ala Ser Lys Ala Ser Asp Ser Val Phe Gly Ile Val Lys Phe Ala
225                 230                 235                 240

Lys Asp Ser Asp Val Ala Ser Ala Thr Ser Asn Asn Leu Ala Val Thr
                245                 250                 255

Pro Lys Ser Leu Gln Ala Leu Lys Ser Thr Lys Asp Lys Tyr Gly Leu
            260                 265                 270

Thr Arg Leu Ser Gly Ser Pro Thr Thr Asp Ala Ser Leu Ala Ala Ala
        275                 280                 285

Ala Thr Asp Ala Val Phe Lys Thr Arg Arg Ile Asn Gly Lys Thr Leu
    290                 295                 300

Asp Asn Asp Ile Thr Ile Thr Asn Asn Asp Ile Asn Cys Tyr Thr Arg
305                 310                 315                 320

Gln Glu Ser Asp Gly Arg Tyr Met Pro Ala Gly Thr Arg Val Gly Asn
                325                 330                 335

Val Thr Trp Val Glu Gly Gln Ser Trp Ile Ser Arg Gly Ala Thr Phe
            340                 345                 350

Thr Cys Asn Ala Pro Trp Glu Ala Ser Ser Arg Leu Ala Leu Asn Val
        355                 360                 365

Asn Val Lys Phe Glu Arg Asn Asn Asp Gly Tyr Asp Asn Arg Ile Phe
    370                 375                 380

Arg Phe Val Val Ile Val Asn Gly Ser Gln Trp Gly Gly Glu Leu Thr
385                 390                 395                 400

Leu Asn Ile Glu Asn Thr Lys Gly Gly Arg Asn Gly His Ser Trp Arg
                405                 410                 415

Phe Glu Ala Tyr Ala Ser Ser Asn Phe Phe Phe Asn Asn Ile Pro Pro
            420                 425                 430

Asn Ala Thr Val Gln Ile Arg Pro Thr Glu Asp Ser Arg Ile Ile Phe
        435                 440                 445

Tyr Asp Cys Met Leu Thr Phe Cys Thr Asn Arg Pro
    450                 455                 460

<210> SEQ ID NO 11
<211> LENGTH: 1428
<212> TYPE: DNA
<213> ORGANISM: Artificial Sequence
<220> FEATURE:
<223> OTHER INFORMATION: N-Strep Effe04p12

<400> SEQUENCE: 11
atggctagcg ctagttggag ccacccgcag ttcgaaaaag gcgccagtaa caatacaatc      60
aaccacgtaa gtgataaatc catttacgtg acatttgacc caacaggtac tgattggcct     120
gataccataa ccaacgtaca agatgcgttg aaaaaaatag gtagttgggc gcgtactgat     180
actgggcttc ctatcgcaac aacttctgtt cgtggtattg ctcagatcgc aaccgaagct     240
gatattaacg ctggcacgga taacactaag attgttactc gaaactgtt agcataccgt     300 atgcagaacc ctaaagcatc acaaaccgta tggggttata cgaagtattc gactgatgcg     360
gaatctacaa ccgtaactaa cgatgcatcg tctattactc cgcgatcgct gaactatgtg     420
ttcaataacc gcaaaggtac agaatcggtt tggggttctt ctaaaatcgc taccactgca     480
caggcggttg ctggtacaga taacactgta actatgactc cgcttaaagt caagcaagcg     540
atcgcgtctc tggttcctgt tcagtcaagt gcgaccgaaa gctcgcaagg tctggtacaa     600

```
ctggcaacag ttgcacaggt tcaggctggt acgatccgtg aagggtatgc aatttcacct    660
tatacgttta ttcgtttaac tgcaactgaa agcaacctgg gcgttattcg tatcgcatca    720
cagacagaag caaacgcagg tactgatgac accaaagcga ttactgcgaa aaaattaatc    780
aatacccgtg caactggttc ccagttcggt gttgtcaaat tagcaacaac tgttggttat    840
gtggcaaaca ccgcactttc ttctaatgct tatgtattgc ctagcgatcg tagtgcggta    900
attaatggtt ctctttatga gtatagcgca atacataaca caaatatca gacgtggaca    960 gatcttgatt ggcatttccc agtaggtgct attgtcatga ctggtttcca gactgaccac   1020
ggtagtttgt atatttgcga tggacgttca ctgaataaaa ataattaccc gttactgttt   1080
gagcgtatag gttatacatt tggtggtggc ggtgattggt ttaacattcc agactgtcga   1140
ggcgttgcag tacgtggtca tgaccgtggg cgtggactaa accctaatcg tgggtatggt   1200
acatatgaag gagatatgtt gggatggcac gaacacccat acaacttat ctaccagaac   1260 ggcggtaaca ttccgaaatg gcaagcagtt tacgaactga aaagcgccga agaatgac    1320 caaagcgctc gcgtatttga tgcttctata actaaagcta ctggtgtggg cggtgaagaa   1380
acccgcatga aaaatatcgc attaaactac gtaattcgcg tattataa              1428
```

<210> SEQ ID NO 12
<211> LENGTH: 475
<212> TYPE: PRT
<213> ORGANISM: Artificial Sequence
<220> FEATURE:
<223> OTHER INFORMATION: N-Strep Effe04p12

<400> SEQUENCE: 12

```
Met Ala Ser Ala Ser Trp Ser His Pro Gln Phe Glu Lys Gly Ala Ser
1               5                   10                  15

Asn Asn Thr Ile Asn His Val Ser Asp Lys Ser Ile Tyr Val Thr Phe
            20                  25                  30

Asp Pro Thr Gly Thr Asp Trp Pro Asp Thr Ile Thr Asn Val Gln Asp
        35                  40                  45

Ala Leu Glu Lys Ile Gly Ser Trp Ala Arg Thr Asp Thr Gly Leu Pro
    50                  55                  60

Ile Ala Thr Thr Ser Val Arg Gly Ile Ala Gln Ile Ala Thr Glu Ala
65                  70                  75                  80

Asp Ile Asn Ala Gly Thr Asp Asn Thr Lys Ile Val Thr Pro Lys Leu
                85                  90                  95

Leu Ala Tyr Arg Met Gln Asn Pro Lys Ala Ser Gln Thr Val Trp Gly
            100                 105                 110

Tyr Thr Lys Tyr Ser Thr Asp Ala Glu Ser Thr Thr Val Thr Asn Asp
        115                 120                 125

Ala Ser Ser Ile Thr Pro Arg Ser Leu Asn Tyr Val Phe Asn Asn Arg
    130                 135                 140

Lys Gly Thr Glu Ser Val Trp Gly Ser Ser Lys Ile Ala Thr Thr Ala
145                 150                 155                 160

Gln Ala Val Ala Gly Thr Asp Asn Thr Val Thr Met Thr Pro Leu Lys
                165                 170                 175

Val Lys Gln Ala Ile Ala Ser Leu Val Pro Val Gln Ser Ser Ala Thr
            180                 185                 190

Glu Ser Ser Gln Gly Leu Val Gln Leu Ala Thr Val Ala Gln Val Gln
        195                 200                 205

Ala Gly Thr Ile Arg Glu Gly Tyr Ala Ile Ser Pro Tyr Thr Phe Ile
    210                 215                 220
```

```
Arg Leu Thr Ala Thr Glu Ser Asn Leu Gly Val Ile Arg Ile Ala Ser
225                 230                 235                 240

Gln Thr Glu Ala Asn Ala Gly Thr Asp Thr Lys Ala Ile Thr Ala
        245                 250                 255

Lys Lys Leu Ile Asn Thr Arg Ala Thr Gly Ser Gln Phe Gly Val Val
            260                 265                 270

Lys Leu Ala Thr Thr Val Gly Tyr Val Ala Asn Thr Ala Leu Ser Ser
        275                 280                 285

Asn Ala Tyr Val Leu Pro Ser Asp Arg Ser Ala Val Ile Asn Gly Ser
    290                 295                 300

Leu Tyr Glu Tyr Ser Ala Ile His Asn Asn Lys Tyr Gln Thr Trp Thr
305                 310                 315                 320

Asp Leu Asp Trp His Phe Pro Val Gly Ala Ile Val Met Thr Gly Phe
                325                 330                 335

Gln Thr Asp His Gly Ser Leu Tyr Ile Cys Asp Gly Arg Ser Leu Asn
            340                 345                 350

Lys Asn Asn Tyr Pro Leu Leu Phe Glu Arg Ile Gly Tyr Thr Phe Gly
        355                 360                 365

Gly Gly Gly Asp Trp Phe Asn Ile Pro Asp Cys Arg Gly Val Ala Val
370                 375                 380

Arg Gly His Asp Arg Gly Arg Gly Leu Asn Pro Asn Arg Gly Tyr Gly
385                 390                 395                 400

Thr Tyr Glu Gly Asp Met Leu Gly Trp His Glu His Pro Leu Gln Leu
                405                 410                 415

Ile Tyr Gln Asn Gly Gly Asn Ile Pro Lys Trp Gln Ala Val Tyr Glu
            420                 425                 430

Leu Lys Ser Ala Glu Lys Asn Asp Gln Ser Ala Arg Val Phe Asp Ala
        435                 440                 445

Ser Ile Thr Lys Ala Thr Gly Val Gly Gly Glu Glu Thr Arg Met Lys
    450                 455                 460

Asn Ile Ala Leu Asn Tyr Val Ile Arg Val Leu
465                 470                 475

<210> SEQ ID NO 13
<211> LENGTH: 1347
<212> TYPE: DNA
<213> ORGANISM: Artificial Sequence
<220> FEATURE:
<223> OTHER INFORMATION: N-Strep AehIp12

<400> SEQUENCE: 13
atggctagct ggagccaccc gcagttcgaa aaaggcgcca gaacaaataa tatcacacag      60
catattagct ctaaagcggg gtcggttgta ttcgaccccg catctgctcc tgcttttgat     120
acgactatca cagatctaca aaagctggga ataaaaatcg atgctcatgc aactaaacca     180
ctaccggtcg catctgaaac tgtatcgggt attgctgaat ggctaccgt tgatgaagtt     240 ctattgggaa atgataaagt tagattagtc actccttata cacttcaaca aaaatgggcg     300
cgtcctaatg cgagcgacac cgtttatggt ctagttagat ataatacagt agcagaacga     360
gaagaagcgg cagcgaaagt tgacgttact gtgaataccg catctttgtg ggacgttgtt     420
cgtaataaat cgattgcaac tgagtccaag cgcggatcag tgagtatttc aactctggta     480
gctgccaaag ctggcgtaga tgatacaaca gcaatgacac cagcgaaagt taaagcggca     540
atcgacacgt tcgcggtaac ttctgtatct ggtgcaactg aaaccgttac gggcacagtt     600
aagaatagtc cggcattaat cactaacgcc gcgcttcata ccggttatgc agttacacct     660
```

```
aaaggtttca ttgaaaccag agccgcacag gctcgcgttg gaacagttcg tatggcaact      720
caagcagaag ctaacgctag aactctggga gacgtggcaa tcagtccagc gacgcttcca      780
atcgcatctg atacacaata tggcatcact gctcttttgc ataacgcgca atccggcgta      840
acaaacaaag cattgagcgc acacggagcg actctgttta tcaacagaaa cggcgactcc      900
atgacgggtg atcttactgt tcataatatc tttactgcta acgggcaaaa cggacgtggc      960
gattcgctga ctagaaagga ttacgttgac ggacttttca atcagaaagc gaatatttcg     1020
catacgcacg aactccaca agaatcatgg cactaatttt ggcagggacc gttagatcgc      1080
ggtaatttcg tgactaatca gccatggtgg aacttcgatg cactcgttat tgaaagttcg     1140
cgtgatggtg gtagctggtt taataccatg gagattagtc gttggcagat cgaacagatg     1200
caagcaaaat atccaaactt caacttggta tcggcacaag aatattattg gtttggtaag     1260
tttagagccg atggtatgta tttcgacacc catacagaga actgctatct gtggagaata     1320
tacggagtta acaaaacttg gagctaa                                         1347
```

<210> SEQ ID NO 14
<211> LENGTH: 448
<212> TYPE: PRT
<213> ORGANISM: Artificial Sequence
<220> FEATURE:
<223> OTHER INFORMATION: N-Strep AehIp12

<400> SEQUENCE: 14

```
Met Ala Ser Trp Ser His Pro Gln Phe Glu Lys Gly Ala Arg Thr Asn
1               5                   10                  15

Asn Ile Thr Gln His Ile Ser Ser Lys Ala Gly Ser Val Val Phe Asp
            20                  25                  30

Pro Ala Ser Ala Pro Ala Phe Asp Thr Thr Ile Thr Asp Leu Gln Lys
        35                  40                  45

Leu Gly Asn Lys Ile Asp Ala His Ala Thr Lys Pro Leu Pro Val Ala
    50                  55                  60

Ser Glu Thr Val Ser Gly Ile Ala Glu Leu Ala Thr Val Asp Glu Val
65                  70                  75                  80

Leu Leu Gly Asn Asp Lys Val Arg Leu Val Thr Pro Tyr Thr Leu Gln
                85                  90                  95

Gln Lys Trp Ala Arg Pro Asn Ala Ser Asp Thr Val Tyr Gly Leu Val
            100                 105                 110

Arg Tyr Asn Thr Val Ala Glu Arg Glu Ala Ala Lys Val Asp
        115                 120                 125

Val Thr Val Asn Thr Ala Ser Leu Trp Asp Val Val Arg Asn Lys Ser
    130                 135                 140

Ile Ala Thr Glu Ser Lys Arg Gly Ser Val Ser Ile Ser Thr Leu Val
145                 150                 155                 160

Ala Ala Lys Ala Gly Val Asp Asp Thr Thr Ala Met Thr Pro Ala Lys
                165                 170                 175

Val Lys Ala Ala Ile Asp Thr Phe Ala Val Thr Ser Val Ser Gly Ala
            180                 185                 190

Thr Glu Thr Val Thr Gly Thr Val Lys Asn Ser Pro Ala Leu Ile Thr
        195                 200                 205

Asn Ala Ala Leu His Thr Gly Tyr Ala Val Thr Pro Lys Gly Phe Ile
    210                 215                 220

Glu Thr Arg Ala Ala Gln Ala Arg Val Gly Thr Val Arg Met Ala Thr
225                 230                 235                 240
```

```
Gln Ala Glu Ala Asn Ala Arg Thr Leu Gly Asp Val Ala Ile Ser Pro
                245                 250                 255
Ala Thr Leu Pro Ile Ala Ser Asp Thr Gln Tyr Gly Ile Thr Ala Leu
            260                 265                 270
Leu His Asn Ala Gln Ser Gly Val Thr Asn Lys Ala Leu Ser Ala His
        275                 280                 285
Gly Ala Thr Leu Phe Ile Asn Arg Asn Gly Asp Ser Met Thr Gly Asp
    290                 295                 300
Leu Thr Val His Asn Ile Phe Thr Ala Asn Gly Gln Asn Gly Arg Gly
305                 310                 315                 320
Asp Ser Leu Thr Arg Lys Asp Tyr Val Asp Gly Leu Phe Asn Gln Lys
                325                 330                 335
Ala Asn Ile Ser His Thr His Gly Thr Pro Gln Glu Ser Trp Thr Leu
            340                 345                 350
Ile Trp Gln Gly Pro Leu Asp Arg Gly Asn Phe Val Thr Asn Gln Pro
        355                 360                 365
Trp Trp Asn Phe Asp Ala Leu Val Ile Glu Ser Ser Arg Asp Gly Gly
    370                 375                 380
Ser Trp Phe Asn Thr Met Glu Ile Ser Arg Trp Gln Ile Glu Gln Met
385                 390                 395                 400
Gln Ala Lys Tyr Pro Asn Phe Asn Leu Val Ser Ala Gln Glu Tyr Tyr
                405                 410                 415
Trp Phe Gly Lys Phe Arg Ala Asp Gly Met Tyr Phe Asp Thr His Thr
            420                 425                 430
Glu Asn Cys Tyr Leu Trp Arg Ile Tyr Gly Val Asn Lys Thr Trp Ser
        435                 440                 445

<210> SEQ ID NO 15
<211> LENGTH: 75
<212> TYPE: DNA
<213> ORGANISM: Artificial Sequence
<220> FEATURE:
<223> OTHER INFORMATION: Synthetic primer

<400> SEQUENCE: 15
gaaggaacta gtcatatggc tagctggagc cacccgcagt tcgaaaaagg cgccgcccag     60
aataactata atcac                                                      75

<210> SEQ ID NO 16
<211> LENGTH: 29
<212> TYPE: DNA
<213> ORGANISM: Artificial Sequence
<220> FEATURE:
<223> OTHER INFORMATION: Synthetic primer

<400> SEQUENCE: 16
cgggatcctc cttacggtct atttgtaca                                       29

<210> SEQ ID NO 17
<211> LENGTH: 76
<212> TYPE: DNA
<213> ORGANISM: Artificial Sequence
<220> FEATURE:
<223> OTHER INFORMATION: Synthetic primer

<400> SEQUENCE: 17
gaaggaacta gtgctagcgc tagctggagc cacccgcagt tcgaaaaagg cgccagtaac     60
aatacaatca accacg                                                     76
```

-continued

<210> SEQ ID NO 18
<211> LENGTH: 26
<212> TYPE: DNA
<213> ORGANISM: Artificial Sequence
<220> FEATURE:
<223> OTHER INFORMATION: Synthetic primer

<400> SEQUENCE: 18
cgggatcccc tctgttataa tacgcg                                         26

<210> SEQ ID NO 19
<211> LENGTH: 75
<212> TYPE: DNA
<213> ORGANISM: Artificial Sequence
<220> FEATURE:
<223> OTHER INFORMATION: Synthetic primer

<400> SEQUENCE: 19
gaaggaacta gtcatatggc tagctggagc cacccgcagt tcgaaaaagg cgccagaaca    60
aataatatca cacag                                                     75

<210> SEQ ID NO 20
<211> LENGTH: 39
<212> TYPE: DNA
<213> ORGANISM: Artificial Sequence
<220> FEATURE:
<223> OTHER INFORMATION: Synthetic primer

<400> SEQUENCE: 20
gaaggaacta gtcatatgag aacaaataat atcacacag                           39

<210> SEQ ID NO 21
<211> LENGTH: 527
<212> TYPE: PRT
<213> ORGANISM: N-Strep  K3p12

<400> SEQUENCE: 21

Met Ser Asn Asn Thr Tyr Gln His Val Ser Asn Glu Ser Arg Tyr Val
1               5                   10                  15

Lys Phe Asp Pro Thr Asp Thr Asn Phe Pro Pro Glu Ile Thr Asp Val
            20                  25                  30

Gln Ala Ala Ile Ala Ala Ile Ser Pro Ala Gly Val Asn Gly Val Pro
        35                  40                  45

Asp Ala Ser Ser Thr Thr Lys Gly Ile Leu Phe Leu Ala Thr Glu Gln
    50                  55                  60

Glu Val Ile Asp Gly Thr Asn Asn Thr Lys Val Thr Pro Ala Thr
65                  70                  75                  80

Leu Ala Thr Arg Leu Ser Tyr Pro Asn Ala Thr Glu Thr Val Tyr Gly
                85                  90                  95

Leu Thr Arg Tyr Ser Thr Asn Asp Glu Ala Ile Ala Gly Val Asn Asn
            100                 105                 110

Glu Ser Ser Ile Thr Pro Ala Lys Phe Thr Val Ala Leu Asn Asn Ala
        115                 120                 125

Phe Glu Thr Arg Val Ser Thr Glu Ser Ser Asn Gly Val Ile Lys Ile
    130                 135                 140

Ser Ser Leu Pro Gln Ala Leu Ala Gly Ala Asp Asp Thr Thr Ala Met
145                 150                 155                 160

Thr Pro Leu Lys Thr Gln Gln Leu Ala Ile Lys Leu Ile Ala Gln Ile
                165                 170                 175

Ala Pro Ser Glu Thr Thr Ala Thr Glu Ser Asp Gln Gly Val Val Gln
            180                 185                 190

Leu Ala Thr Val Ala Gln Val Arg Gln Gly Thr Leu Arg Glu Gly Tyr
        195                 200                 205

Ala Ile Ser Pro Tyr Thr Phe Met Asn Ser Ser Ala Thr Glu Glu Tyr
        210                 215                 220

Lys Gly Val Ile Lys Leu Gly Thr Gln Ser Glu Val Asn Ser Asn Asn
225                 230                 235                 240

Ala Ser Val Ala Val Thr Gly Ala Thr Leu Asn Gly Arg Gly Ser Thr
                245                 250                 255

Thr Ser Met Arg Gly Val Val Arg Leu Thr Thr Thr Ala Gly Ser Gln
                260                 265                 270

Ser Gly Gly Asp Ala Ser Ser Ala Leu Ala Trp Asn Ala Asp Val Ile
                275                 280                 285

His Gln Arg Gly Gly Gln Thr Ile Asn Gly Thr Leu Arg Ile Asn Asn
        290                 295                 300

Thr Leu Thr Ile Ala Ser Gly Ala Asn Ile Thr Gly Thr Val Asn
305                 310                 315                 320

Met Thr Gly Gly Tyr Ile Gln Gly Lys Arg Val Val Thr Gln Asn Glu
                325                 330                 335

Ile Asp Arg Thr Ile Pro Val Gly Ala Ile Met Met Trp Ala Ala Asp
                340                 345                 350

Ser Leu Pro Ser Asp Ala Trp Arg Phe Cys His Gly Thr Val Ser
                355                 360                 365

Ala Ser Asp Cys Pro Leu Tyr Ala Ser Arg Ile Gly Thr Arg Tyr Gly
        370                 375                 380

Gly Ser Ser Ser Asn Pro Gly Leu Pro Asp Met Arg Gly Leu Phe Val
385                 390                 395                 400

Arg Gly Ser Gly Arg Gly Ser His Leu Thr Asn Pro Asn Val Asn Gly
                405                 410                 415

Asn Asp Gln Phe Gly Lys Pro Arg Leu Gly Val Gly Cys Thr Gly Gly
                420                 425                 430

Tyr Val Gly Glu Val Gln Lys Gln Gln Met Ser Tyr His Lys His Ala
                435                 440                 445

Gly Gly Phe Gly Glu Trp Asp Asp Ser Gly Ala Phe Gly Asn Thr Arg
        450                 455                 460

Arg Ser Asn Phe Val Gly Thr Arg Lys Gly Leu Asp Trp Asp Asn Arg
465                 470                 475                 480

Ser Tyr Phe Thr Asn Asp Gly Tyr Glu Ile Asp Pro Ala Ser Gln Arg
                485                 490                 495

Asn Ser Arg Tyr Thr Leu Asn Arg Pro Glu Leu Ile Gly Asn Glu Thr
                500                 505                 510

Arg Pro Trp Asn Ile Ser Leu Asn Tyr Ile Ile Lys Val Lys Glu
        515                 520                 525

<210> SEQ ID NO 22
<211> LENGTH: 527
<212> TYPE: PRT
<213> ORGANISM: N-Strep  T2p12

<400> SEQUENCE: 22

Met Ser Asn Asn Thr Tyr Gln His Val Ser Asn Glu Ser Arg Tyr Val
1               5                   10                  15

Lys Phe Asp Pro Thr Asp Thr Asn Phe Pro Pro Glu Ile Thr Asp Val
                20                  25                  30

Gln Ala Ala Ile Ala Ala Ile Ser Pro Ala Gly Val Asn Gly Val Pro
        35                  40                  45

```
Asp Ala Ser Ser Thr Thr Lys Gly Ile Leu Phe Leu Ala Thr Glu Gln
    50                  55                  60
Glu Val Ile Asp Gly Thr Asn Asn Thr Lys Ala Val Thr Pro Ala Thr
65                  70                  75                  80
Leu Ala Thr Arg Leu Ser Tyr Pro Asn Ala Thr Glu Ala Val Tyr Gly
                85                  90                  95
Leu Thr Arg Tyr Ser Thr Asp Asp Glu Ala Ile Ala Gly Val Asn Asn
                100                 105                 110
Glu Ser Ser Ile Thr Pro Ala Lys Phe Thr Val Ala Leu Asn Asn Val
            115                 120                 125
Phe Glu Thr Arg Val Ser Thr Glu Ser Ser Asn Gly Val Ile Lys Ile
130                 135                 140
Ser Ser Leu Pro Gln Ala Leu Ala Gly Ala Asp Asp Thr Thr Ala Met
145                 150                 155                 160
Thr Pro Leu Lys Thr Gln Gln Leu Ala Val Lys Leu Ile Ala Gln Ile
                165                 170                 175
Ala Pro Ser Lys Asn Ala Ala Thr Glu Ser Glu Gln Gly Val Ile Gln
                180                 185                 190
Leu Ala Thr Val Ala Gln Ala Arg Gln Gly Thr Leu Arg Glu Gly Tyr
            195                 200                 205
Ala Ile Ser Pro Tyr Thr Phe Met Asn Ser Thr Ala Thr Glu Glu Tyr
            210                 215                 220
Lys Gly Val Ile Lys Leu Gly Thr Gln Ser Glu Val Asn Ser Asn Asn
225                 230                 235                 240
Ala Ser Val Ala Val Thr Gly Ala Thr Leu Asn Gly Arg Gly Ser Thr
                245                 250                 255
Thr Ser Met Arg Gly Val Val Lys Leu Thr Thr Thr Ala Gly Ser Gln
                260                 265                 270
Ser Gly Gly Asp Ala Ser Ser Ala Leu Ala Trp Asn Ala Asp Val Ile
            275                 280                 285
His Gln Arg Gly Gly Gln Thr Ile Asn Gly Thr Leu Arg Ile Asn Asn
            290                 295                 300
Thr Leu Thr Ile Ala Ser Gly Gly Ala Asn Ile Thr Gly Thr Val Asn
305                 310                 315                 320
Met Thr Gly Gly Tyr Ile Gln Gly Lys Arg Val Val Thr Gln Asn Glu
                325                 330                 335
Ile Asp Arg Thr Ile Pro Val Gly Ala Ile Met Met Trp Ala Ala Asp
                340                 345                 350
Ser Leu Pro Ser Asp Ala Trp Arg Phe Cys His Gly Gly Thr Val Ser
            355                 360                 365
Ala Ser Asp Cys Pro Leu Tyr Ala Ser Arg Ile Gly Thr Arg Tyr Gly
            370                 375                 380
Gly Thr Ser Ser Asn Pro Gly Leu Pro Asp Met Arg Gly Leu Phe Val
385                 390                 395                 400
Arg Gly Ser Gly Arg Gly Ser His Leu Thr Asn Pro Asn Val Asn Gly
                405                 410                 415
Asn Asp Gln Phe Gly Lys Pro Arg Leu Gly Val Gly Cys Thr Gly Gly
                420                 425                 430
Tyr Val Gly Glu Val Gln Lys Gln Gln Met Ser Tyr His Lys His Ala
            435                 440                 445
Gly Gly Phe Gly Glu Tyr Asp Asp Ser Gly Ala Phe Gly Asn Thr Arg
450                 455                 460
Arg Ser Asn Phe Val Gly Thr Arg Lys Gly Leu Asp Trp Asp Asn Arg
```

```
                465                 470                 475                 480
Ser Tyr Phe Thr Asn Asp Gly Tyr Glu Ile Asp Pro Ala Ser Gln Arg
                    485                 490                 495

Asn Ser Arg Tyr Thr Leu Asn Arg Pro Glu Leu Ile Gly Asn Glu Thr
                500                 505                 510

Arg Pro Trp Asn Ile Ser Leu Asn Tyr Ile Ile Lys Val Lys Glu
                515                 520                 525

<210> SEQ ID NO 23
<211> LENGTH: 473
<212> TYPE: PRT
<213> ORGANISM: N-Strep T4p12

<400> SEQUENCE: 23

Met Ser Asn Asn Thr Tyr Gln His Val Ser Asn Glu Ser Arg Tyr Val
1               5                   10                  15

Lys Phe Asp Pro Thr Asp Thr Asn Phe Pro Pro Glu Ile Thr Asp Val
                20                  25                  30

His Ala Ala Ile Ala Ala Ile Ser Pro Ala Gly Thr Arg Tyr Ser Thr
            35                  40                  45

Asn Asp Glu Ala Ile Ala Gly Val Asn Asn Glu Ser Ser Ile Thr Pro
        50                  55                  60

Ala Lys Phe Thr Val Ala Leu Asn Asn Ala Phe Glu Thr Arg Val Ser
65                  70                  75                  80

Thr Glu Ser Ser Asn Gly Val Ile Lys Ile Ser Ser Leu Pro Gln Ala
                85                  90                  95

Leu Ala Gly Ala Asp Asp Thr Thr Ala Met Thr Pro Leu Lys Thr Gln
                100                 105                 110

Gln Leu Ala Ile Lys Leu Ile Ala Gln Ile Ala Pro Ser Glu Thr Thr
            115                 120                 125

Ala Thr Glu Ser Asp Gln Gly Val Val Gln Leu Ala Thr Val Ala Gln
        130                 135                 140

Val Arg Gln Gly Thr Leu Arg Glu Gly Tyr Ala Ile Ser Pro Tyr Thr
145                 150                 155                 160

Phe Met Asn Ser Ser Ser Thr Glu Glu Tyr Lys Gly Val Ile Lys Leu
                165                 170                 175

Gly Thr Gln Ser Glu Val Asn Ser Asn Asn Ala Ser Val Ala Val Thr
                180                 185                 190

Gly Ala Thr Leu Asn Gly Arg Gly Ser Thr Thr Ser Met Arg Gly Val
            195                 200                 205

Val Lys Leu Thr Thr Thr Ala Gly Ser Gln Ser Gly Gly Asp Ala Ser
210                 215                 220

Ser Ala Leu Ala Trp Asn Ala Asp Val Ile Gln Gln Arg Gly Gly Gln
225                 230                 235                 240

Ile Ile Tyr Gly Thr Leu Arg Ile Glu Asp Thr Phe Thr Ile Ala Asn
                245                 250                 255

Gly Gly Ala Asn Ile Thr Gly Thr Val Arg Met Thr Gly Gly Tyr Ile
                260                 265                 270

Gln Gly Asn Arg Ile Val Thr Gln Asn Glu Ile Asp Arg Thr Ile Pro
            275                 280                 285

Val Gly Ala Ile Met Met Trp Ala Ala Asp Ser Leu Pro Ser Asp Ala
        290                 295                 300

Trp Arg Phe Cys His Gly Gly Thr Val Ser Ala Ser Asp Cys Pro Leu
305                 310                 315                 320

Tyr Ala Ser Arg Ile Gly Thr Arg Tyr Gly Gly Asn Pro Ser Asn Pro
```

```
                    325                 330                 335
Gly Leu Pro Asp Met Arg Gly Leu Phe Val Arg Gly Ser Gly Arg Gly
                340                 345                 350

Ser His Leu Thr Asn Pro Asn Val Asn Gly Asn Asp Gln Phe Gly Lys
            355                 360                 365

Pro Arg Leu Gly Val Gly Cys Thr Gly Gly Tyr Val Gly Glu Val Gln
        370                 375                 380

Ile Gln Gln Met Ser Tyr His Lys His Ala Gly Gly Phe Gly Glu His
385                 390                 395                 400

Asp Asp Leu Gly Ala Phe Gly Asn Thr Arg Arg Ser Asn Phe Val Gly
                405                 410                 415

Thr Arg Lys Gly Leu Asp Trp Asp Asn Arg Ser Tyr Phe Thr Asn Asp
            420                 425                 430

Gly Tyr Glu Ile Asp Pro Glu Ser Gln Arg Asn Ser Lys Tyr Thr Leu
        435                 440                 445

Asn Arg Pro Glu Leu Ile Gly Asn Glu Thr Arg Pro Trp Asn Ile Ser
450                 455                 460

Leu Asn Tyr Ile Ile Lys Val Lys Glu
465                 470

<210> SEQ ID NO 24
<211> LENGTH: 516
<212> TYPE: PRT
<213> ORGANISM: N-Strep RB32-33

<400> SEQUENCE: 24

Met Ser Asn Asn Thr Tyr Gln His Val Ser Asn Glu Ser Lys Tyr Val
1               5                   10                  15

Lys Phe Asp Pro Val Gly Ser Asn Phe Pro Asp Thr Val Thr Thr Val
            20                  25                  30

Gln Ser Ala Leu Ser Lys Ile Ser Asn Ile Gly Val Asn Gly Ile Pro
        35                  40                  45

Asp Ala Thr Met Glu Val Lys Gly Ile Ala Met Ile Ala Ser Glu Gln
    50                  55                  60

Glu Val Leu Asp Gly Thr Asn Asn Ser Lys Ile Val Thr Pro Ala Thr
65                  70                  75                  80

Leu Ala Thr Arg Leu Leu Tyr Pro Asn Ala Thr Glu Thr Lys Tyr Gly
                85                  90                  95

Leu Thr Arg Tyr Ser Thr Asn Glu Glu Thr Leu Glu Gly Ser Asp Asn
            100                 105                 110

Asn Ser Ser Ile Thr Pro Gln Lys Leu Lys Tyr His Thr Asp Asp Val
        115                 120                 125

Phe Gln Asn Arg Tyr Ser Ser Glu Ser Ser Asn Gly Val Ile Lys Ile
    130                 135                 140

Ser Ser Thr Pro Ala Ala Leu Ala Gly Val Asp Asp Thr Thr Ala Met
145                 150                 155                 160

Thr Pro Leu Lys Thr Gln Lys Leu Ala Ile Lys Leu Ile Ser Gln Ile
                165                 170                 175

Ala Pro Ser Glu Asp Thr Ala Ser Glu Ser Val Arg Gly Val Val Gln
            180                 185                 190

Leu Ser Thr Val Ala Gln Thr Arg Gln Gly Thr Leu Arg Glu Gly Tyr
        195                 200                 205

Ala Ile Ser Pro Tyr Thr Phe Met Asn Ser Val Ala Thr Gln Glu Tyr
    210                 215                 220

Lys Gly Val Ile Arg Leu Gly Thr Gln Ser Glu Ile Asn Ser Asn Leu
```

```
                225                 230                 235                 240
Gly Asp Val Ala Val Thr Gly Glu Thr Leu Asn Gly Arg Gly Ala Thr
                245                 250                 255

Ser Ser Met Arg Gly Val Val Lys Leu Thr Thr Gln Ala Gly Ile Ala
                260                 265                 270

Pro Glu Gly Asp Gly Ser Gly Ala Leu Ala Trp Asn Ala Asp Val Ile
                275                 280                 285

Asn Thr Arg Gly Gly Gln Thr Ile Asn Gly Ser Leu Asn Leu Asp His
                290                 295                 300

Leu Thr Ala Asn Gly Ile Trp Ser Arg Gly Gly Met Trp Lys Asn Gly
305                 310                 315                 320

Asp Gln Pro Val Ala Thr Glu Arg Tyr Ala Ser Glu Arg Val Pro Val
                325                 330                 335

Gly Thr Ile Met Met Phe Ala Gly Asp Ser Ala Pro Pro Gly Trp Ile
                340                 345                 350

Met Cys His Gly Gly Thr Val Ser Gly Asp Gln Tyr Pro Asp Tyr Arg
                355                 360                 365

Asn Thr Val Gly Ala Arg Phe Gly Gly Asp Trp Asn Asn Pro Gly Ile
                370                 375                 380

Pro Asp Met Arg Gly Leu Phe Val Arg Gly Ala Gly Thr Gly Gly His
385                 390                 395                 400

Ile Leu Asn Gln Arg Gly Gln Asp Gly Tyr Gly Lys Asp Arg Leu Gly
                405                 410                 415

Val Gly Cys Asp Gly Met His Val Gly Gly Val Gln Ala Gln Gln Met
                420                 425                 430

Ser Tyr His Lys His Ala Gly Gly Trp Gly Glu Tyr Gln Arg His Glu
                435                 440                 445

Ala Pro Phe Gly Ala Ser Val Tyr Gln Gly Tyr Leu Gly Thr Arg Lys
                450                 455                 460

Tyr Ser Asp Trp Asp Asn Ala Ser Tyr Phe Thr Asn Asp Gly Phe Glu
465                 470                 475                 480

Leu Gly Gly Pro Arg Asp Ala Leu Gly Thr Leu Asn Arg Glu Gly Leu
                485                 490                 495

Ile Gly Tyr Glu Thr Arg Pro Trp Asn Ile Ser Leu Asn Tyr Ile Ile
                500                 505                 510

Lys Ile His Tyr
            515

<210> SEQ ID NO 25
<211> LENGTH: 516
<212> TYPE: PRT
<213> ORGANISM: N-Strep AR1p12

<400> SEQUENCE: 25

Met Ser Asn Asn Thr Tyr Gln His Val Ser Asn Glu Ser Lys Tyr Val
1               5                   10                  15

Lys Phe Asp Pro Thr Gly Ser Asn Phe Pro Asp Thr Val Thr Thr Val
                20                  25                  30

Gln Ser Ala Leu Ser Lys Ile Ser Asn Ile Gly Val Asn Gly Ile Pro
                35                  40                  45

Asp Ala Thr Met Glu Val Lys Gly Ile Ala Met Ile Ala Ser Glu Gln
                50                  55                  60

Glu Val Leu Asp Gly Thr Asn Asn Ser Lys Ile Val Thr Pro Ala Thr
65                  70                  75                  80

Leu Ala Thr Arg Leu Leu Tyr Pro Asn Ala Thr Glu Thr Lys Tyr Gly
```

```
                85                  90                  95
Leu Thr Arg Tyr Ser Thr Asn Glu Glu Thr Leu Glu Gly Ser Asp Asn
            100                 105                 110

Asn Ser Ser Ile Thr Pro Gln Lys Leu Lys Tyr His Thr Asp Asp Val
            115                 120                 125

Phe Gln Asn Arg Tyr Ser Ser Glu Ser Ser Asn Gly Val Ile Lys Ile
            130                 135                 140

Ser Ser Thr Pro Ala Ala Leu Ala Gly Val Asp Thr Thr Ala Met
145                 150                 155                 160

Thr Pro Leu Lys Thr Gln Lys Leu Ala Ile Lys Leu Ile Ser Gln Ile
                165                 170                 175

Ala Pro Ser Glu Asp Thr Ala Ser Glu Ser Val Arg Gly Val Val Gln
            180                 185                 190

Leu Ser Thr Val Ala Gln Thr Arg Gln Gly Thr Leu Arg Glu Gly Tyr
            195                 200                 205

Ala Ile Ser Pro Tyr Thr Phe Met Asn Ser Val Ala Thr Gln Glu Tyr
            210                 215                 220

Lys Gly Val Ile Arg Leu Gly Thr Gln Ser Glu Ile Asn Ser Asn Leu
225                 230                 235                 240

Gly Asp Val Ala Val Thr Gly Thr Leu Asn Gly Arg Gly Ala Thr
                245                 250                 255

Gly Ser Met Arg Gly Val Val Lys Leu Thr Thr Gln Ala Gly Ile Ala
            260                 265                 270

Pro Glu Gly Asp Ser Ser Gly Ala Leu Ala Trp Asn Ala Asp Val Ile
            275                 280                 285

Asn Thr Arg Gly Gly Gln Thr Ile Asn Gly Ser Leu Asn Leu Asp His
            290                 295                 300

Leu Thr Ala Asn Gly Ile Trp Ser Arg Gly Gly Met Trp Lys Asn Gly
305                 310                 315                 320

Asp Gln Pro Val Ala Thr Glu Arg Tyr Ala Ser Glu Arg Val Pro Val
                325                 330                 335

Gly Thr Ile Met Met Phe Ala Gly Asp Ser Ala Pro Pro Gly Trp Ile
            340                 345                 350

Met Cys His Gly Gly Thr Val Ser Gly Asp Gln Tyr Pro Asp Tyr Arg
            355                 360                 365

Asn Thr Val Gly Thr Arg Phe Gly Gly Asp Trp Asn Asn Pro Gly Ile
            370                 375                 380

Pro Asp Met Arg Gly Leu Phe Val Arg Gly Ala Gly Thr Gly Gly His
385                 390                 395                 400

Ile Leu Asn Gln Arg Gly Gln Asp Gly Tyr Gly Lys Asp Arg Leu Gly
                405                 410                 415

Val Gly Cys Asp Gly Met His Val Gly Gly Val Gln Ala Gln Gln Met
            420                 425                 430

Ser Tyr His Lys His Ala Gly Gly Trp Gly Glu Tyr Asn Arg Ser Glu
            435                 440                 445

Gly Pro Phe Gly Ala Ser Val Tyr Gln Gly Tyr Leu Gly Thr Arg Lys
            450                 455                 460

Tyr Ser Asp Trp Asp Asn Ala Ser Tyr Phe Thr Asn Asp Gly Phe Glu
465                 470                 475                 480

Leu Gly Gly Pro Arg Asp Ala Leu Gly Thr Leu Asn Arg Glu Gly Leu
                485                 490                 495

Ile Gly Tyr Glu Thr Arg Pro Trp Asn Ile Ser Leu Asn Tyr Ile Ile
            500                 505                 510
```

```
Lys Ile His Tyr
        515

<210> SEQ ID NO 26
<211> LENGTH: 518
<212> TYPE: PRT
<213> ORGANISM: N-Strep PP01p12
<220> FEATURE:
<221> NAME/KEY: misc_feature
<222> LOCATION: (399)..(399)
<223> OTHER INFORMATION: Xaa can be any naturally occurring amino acid

<400> SEQUENCE: 26

Met Ser Asn Asn Thr Tyr Gln His Val Ser Asn Glu Ser Lys Tyr Val
1               5                   10                  15

Lys Phe Asp Pro Val Gly Ser Asn Phe Pro Asp Thr Val Thr Thr Val
            20                  25                  30

Gln Ser Ala Leu Ser Lys Ile Ser Asn Ile Gly Val Asn Gly Ile Pro
        35                  40                  45

Asp Ala Ser Met Glu Val Lys Gly Ile Ala Met Ile Ala Ser Glu Gln
    50                  55                  60

Glu Val Leu Asp Gly Thr Asn Asn Ser Lys Ile Val Thr Pro Ala Thr
65                  70                  75                  80

Leu Ala Thr Arg Leu Leu Tyr Pro Asn Ala Thr Glu Thr Lys Tyr Gly
                85                  90                  95

Leu Thr Arg Tyr Ser Thr Asn Glu Glu Thr Leu Glu Gly Ser Asp Asn
            100                 105                 110

Asn Ser Ser Ile Thr Pro Gln Lys Leu Lys Tyr His Thr Asp Asp Val
        115                 120                 125

Phe Gln Asn Arg Tyr Ser Ser Glu Ser Ser Asn Gly Val Ile Lys Ile
    130                 135                 140

Ser Ser Thr Pro Ala Ala Leu Ala Gly Val Asp Asp Thr Thr Ala Met
145                 150                 155                 160

Thr Pro Leu Lys Thr Gln Lys Leu Ala Ile Lys Leu Ile Ser Gln Ile
                165                 170                 175

Ala Pro Ser Glu Asp Thr Ala Ser Glu Ser Val Arg Gly Val Val Gln
            180                 185                 190

Leu Ser Thr Val Ala Gln Thr Arg Gln Gly Thr Leu Arg Glu Gly Tyr
        195                 200                 205

Ala Ile Ser Pro Tyr Thr Phe Met Asn Ser Val Ala Thr Gln Glu Tyr
    210                 215                 220

Lys Gly Val Ile Arg Leu Gly Thr Gln Ser Glu Ile Asn Ser Asn Leu
225                 230                 235                 240

Gly Asp Val Ala Val Thr Gly Glu Thr Leu Asn Gly Arg Gly Ala Thr
                245                 250                 255

Gly Ser Met Arg Gly Val Val Lys Leu Thr Thr Gln Ala Gly Ile Ala
            260                 265                 270

Pro Glu Gly Asp Ser Ser Gly Ala Leu Ala Trp Asn Ala Asp Val Ile
        275                 280                 285

Asn Thr Arg Gly Gly Gln Thr Ile Asn Gly Ser Leu Asn Leu Asp His
    290                 295                 300

Leu Thr Ala Asn Gly Ile Trp Ser Arg Gly Met Trp Lys Asn Gly
305                 310                 315                 320

Asp Gln Pro Val Ala Thr Glu Arg Tyr Ala Ser Glu Arg Val Pro Val
                325                 330                 335

Gly Thr Ile Met Met Phe Ala Gly Asp Ser Ala Pro Pro Gly Trp Ile
            340                 345                 350
```

```
Met Cys His Gly Gly Thr Val Ser Gly Asp Gln Tyr Pro Asp Tyr Arg
            355                 360                 365

Asn Thr Val Gly Thr Arg Phe Gly Gly Asp Trp Asn Asn Pro Gly Ile
        370                 375                 380

Pro Asp Met Arg Gly Leu Phe Val Arg Gly Ala Gly Thr Gly Xaa His
385                 390                 395                 400

Ile Leu Asn Gln Arg Gly Gln Asp Gly Tyr Gly Lys Asp Arg Leu Gly
                405                 410                 415

Val Gly Cys Asp Gly Met His Val Gly Val Gln Ala Gln Gln Ile
                420                 425                 430

Ser Tyr His Lys His Ala Gly Ala Trp Gly Glu Asn Gly Asn Asn Arg
            435                 440                 445

Gly Tyr Ala Pro Phe Gly Ala Ser Asn Gly Ser Gly Tyr Leu Gly Asn
        450                 455                 460

Gly Arg Ser Ala Asp Trp Asp Asn His Leu Phe Phe Thr Asn Asp Gly
465                 470                 475                 480

Phe Glu Met Gly Gly Pro Arg Asp Ser Phe Gly Thr Leu Asn Arg Glu
                485                 490                 495

Gly Leu Ile Gly Tyr Glu Thr Arg Pro Trp Asn Ile Ser Leu Asn Tyr
            500                 505                 510

Ile Ile Lys Ile His Tyr
            515

<210> SEQ ID NO 27
<211> LENGTH: 516
<212> TYPE: PRT
<213> ORGANISM: N-Strep RB69

<400> SEQUENCE: 27

Met Ser Asn Asn Thr Tyr Gln His Val Ser Asn Glu Ser Val Tyr Val
1               5                   10                  15

Glu Phe Asp Pro Thr Gly Ser Asn Phe Asp Ser Ser Ile Thr Asn Val
                20                  25                  30

Gln Ala Ala Leu Ala Ser Ile Ser Ala Tyr Gly Val Lys Gly Val Pro
            35                  40                  45

Asp Ala Ser Glu Ala Glu Lys Gly Val Ile Gln Leu Ala Thr Glu Gln
        50                  55                  60

Glu Val Leu Asp Gly Phe Asn Ser Thr Lys Ala Val Thr Pro Ala Thr
65                  70                  75                  80

Leu Asn Ala Arg Leu Gln Tyr Pro Asn Ala Ser Glu Thr Gln Tyr Gly
                85                  90                  95

Val Thr Lys Tyr Ala Thr Gln Glu Glu Ala Ile Ala Gly Thr Leu Asp
                100                 105                 110

Thr Val Ser Ile Thr Pro Leu Lys Leu Asn Gln Thr Ile Asp Asn Thr
            115                 120                 125

Phe Ser Thr Arg Tyr Ser Thr Glu Thr Thr Asn Gly Val Ile Lys Ile
        130                 135                 140

Ala Thr Gln Thr Ala Ala Leu Ala Gly Ser Asp Asp Thr Thr Ala Met
145                 150                 155                 160

Thr Pro Leu Lys Thr Gln Gln Leu Ala Ile Lys Leu Ile Ser Gln Ile
                165                 170                 175

Ala Pro Asn Asn Asp Pro Ala Ser Glu Ser Ile Thr Gly Val Val Arg
            180                 185                 190

Leu Ala Thr Val Ala Gln Thr Arg Gln Gly Thr Leu Arg Glu Gly Tyr
        195                 200                 205
```

Ala Ile Ser Pro Tyr Thr Phe Met Asn Ser Val Ala Thr Gln Glu Tyr
    210                 215                 220

Lys Gly Val Ile Arg Leu Gly Thr Gln Ala Glu Ile Asn Ser Asn Leu
225                 230                 235                 240

Gly Asp Val Ala Val Thr Gly Glu Thr Leu Asn Gly Arg Gly Ala Thr
                245                 250                 255

Gly Ser Met Arg Gly Val Val Lys Leu Thr Thr Gln Ala Gly Val Ala
            260                 265                 270

Pro Glu Gly Asp Ser Ser Gly Ala Leu Ala Trp Asn Ala Asp Val Ile
        275                 280                 285

Asn Thr Arg Gly Gly Gln Thr Ile Asn Gly Ser Leu Asn Leu Asp His
    290                 295                 300

Leu Thr Ala Asn Gly Ile Trp Ser Arg Gly Gly Met Trp Lys Asn Gly
305                 310                 315                 320

Asp Gln Pro Val Ala Thr Glu Arg Tyr Ala Ser Glu Arg Val Pro Val
                325                 330                 335

Gly Thr Ile Gln Met Phe Ala Gly Asp Ser Ala Pro Pro Gly Trp Val
            340                 345                 350

Leu Cys His Gly Gly Thr Ile Ser Gly Asp Gln Phe Pro Asp Tyr Arg
        355                 360                 365

Asn Val Val Gly Thr Arg Phe Gly Gly Asp Trp Asn Asn Pro Gly Ile
    370                 375                 380

Pro Asp Met Arg Gly Leu Phe Val Arg Gly Ala Gly Thr Gly Ser His
385                 390                 395                 400

Ile Leu Asn Asn Arg Gly Gln Asp Gly Tyr Gly Lys Asp Arg Leu Gly
                405                 410                 415

Val Gly Cys Asp Gly Met His Val Gly Gly Val Gln Ala Gln Gln Met
            420                 425                 430

Ser Tyr His Lys His Ala Gly Gly Trp Gly Glu Phe Gln Arg His Glu
        435                 440                 445

Ala Pro Phe Gly Ala Ser Val Tyr Gln Gly Tyr Leu Gly Thr Arg Lys
    450                 455                 460

Tyr Ser Asp Trp Asp Asn Ala Ser Tyr Phe Thr Asn Asp Gly Phe Glu
465                 470                 475                 480

Leu Gly Gly His Arg Asp Ala Thr Gly Thr Leu Asn Arg Glu Gly Leu
                485                 490                 495

Ile Gly Tyr Glu Thr Arg Pro Trp Asn Ile Ser Leu Asn Tyr Ile Ile
            500                 505                 510

Lys Val His Tyr
        515

<210> SEQ ID NO 28
<211> LENGTH: 463
<212> TYPE: PRT
<213> ORGANISM: N-Strep RB43p12

<400> SEQUENCE: 28

Met Ser Asn Asn Thr Ile Asn His Val Ser Asp Ala Ser Val Tyr Val
1               5                   10                  15

Thr Phe Asp Pro Ala Gly Thr Gln Trp Pro Ser Thr Phe Val Asn Val
                20                  25                  30

Gln Gln Ala Leu Ala Ser Ile Gly Pro Trp Ala Arg Thr Asp Val Gly
            35                  40                  45

Leu Pro Asn Ala Ala Pro Gly Met Arg Gly Ile Ala Ala Ile Ala Thr
        50                  55                  60

Glu Ala Met Ile Asp Ala Gly Thr Asp Asn Glu Thr Ile Val Thr Pro
 65                  70                  75                  80

Ala Leu Leu Ala Tyr Arg Leu Gln Asn Pro His Ala Ser Gln Thr Val
                 85                  90                  95

Trp Gly Tyr Thr Lys Tyr Ala Thr Asp Ala Glu Ala Val Asp Val Ala
            100                 105                 110

Asn Asp Leu Val Ser Leu Thr Pro Arg Ser Ile Asn Val Val Phe Asn
        115                 120                 125

Thr Arg His Ala Ser Glu Thr Val Trp Gly Ser Ser Lys Leu Ser Thr
130                 135                 140

Thr Ala Gln Ala Thr Ala Gly Thr Asp Thr Thr Ser Met Thr Pro
145                 150                 155                 160

Leu Lys Val Lys Gln Ala Ile Ser Ala Leu Val Pro Gln Ser Asn
                165                 170                 175

Ala Thr Glu Ser Ala Phe Gly Leu Val Gln Leu Ala Thr Val Ser Glu
            180                 185                 190

Val Arg Ala Gly Thr Ile Arg Asp Gly Phe Ala Ile Ser Pro Tyr Thr
        195                 200                 205

Phe Ile Arg Leu Asn Ala Thr Glu Ser Asp Leu Gly Ile Val Arg Leu
210                 215                 220

Ala Ser Gln Ala Glu Val Asn Ala Gly Thr Asp Asp Thr Lys Ala Val
225                 230                 235                 240

Thr Pro Leu Lys Leu Ala Asn Leu Lys Gly Ser Gly Ser Phe Gly
                245                 250                 255

Leu Val Lys Leu Ser Thr Glu Val Asn Ala Gly Leu Ala Asn Thr Ala
            260                 265                 270

Leu Ser Ala Gly Ala Asn Val Val Pro Ser Asn Arg Asp Ser Ala Ile
        275                 280                 285

Thr Gly Gly Ala Leu Tyr Gln Gly Ser Val Ala Ala Asn Lys Tyr
            290                 295                 300

Gln Thr His Ser Asp Ile Glu Ala Ser Leu Pro Ile Gly Cys Met Met
305                 310                 315                 320

Met Ala Ala Phe Asn Ser Asp Tyr Gly Asn Leu Cys Ile Ala Asn Gly
                325                 330                 335

Arg Gly Met Tyr Thr Tyr Glu Tyr Pro Glu Leu Phe Ala Leu Ile Gly
            340                 345                 350

Tyr Thr Tyr Gly Gly Ser Gly Asn Ile Phe Asn Leu Pro Asp Met Arg
        355                 360                 365

Gly Val Val Ala Arg Gly Phe Asp Ala Gly Arg Gly Leu Asp Pro Gly
370                 375                 380

Arg Gly Phe Gly Thr Tyr Gln His His Glu Val Gln Ser His Glu His
385                 390                 395                 400

Pro Leu Gln Met Ile Tyr Gln Ser Gly Gly Asn Leu Pro Ser Trp Gln
                405                 410                 415

Cys Val Tyr Glu Leu Arg Thr Ala Glu Lys Asn Asp Gln Gln Leu Tyr
            420                 425                 430

Trp Pro Asp Pro Ser Leu Ser Lys Ala Met Ala Val Gly Gly Asn Glu
        435                 440                 445

Thr Arg Met Lys Asn Leu Ala Ile Asn Tyr Val Ile Arg Val Arg
    450                 455                 460

<210> SEQ ID NO 29
<211> LENGTH: 464
<212> TYPE: PRT

<213> ORGANISM: N-Strep RB49p12

<400> SEQUENCE: 29

```
Met Ala Asn Asn Thr Ile Asn His Val Lys Asp Asp Ala Gln Tyr Val
1               5                   10                  15

Lys Phe Asn Pro Val Asn Asp Trp Pro Gln Ser Ile Thr Asn Val Gln
            20                  25                  30

Ala Ala Leu Ala Ala Ile Asn Gly Phe Ala Val Asn Gly Leu Pro Asp
        35                  40                  45

Ala Thr Glu Asp Thr Ala Gly Ile Ala Ala Ile Ala Thr Gln Glu Glu
    50                  55                  60

Val Asn Asp Gly Thr Val Asp Asn Lys Ile Val Thr Pro Lys Thr Leu
65                  70                  75                  80

Ala Val Lys Met Ser Arg Pro Asp Ala Thr Lys Glu Val Lys Gly Ile
                85                  90                  95

Thr Arg Phe Ala Thr Met Glu Glu Ser Leu Gln Glu Ser Asn Glu Asn
            100                 105                 110

Met Ala Ile Gly Pro Asp Thr Leu Asn His Tyr Phe Thr Thr Lys Lys
        115                 120                 125

Ala Ser Glu Ser Val Gln Gly Thr Ile Lys Ile Cys Ser Leu Glu Ala
    130                 135                 140

Ala Lys Ile Gly Ser Asp Asp Thr Met Ala Val Thr Pro Lys Lys Met
145                 150                 155                 160

His Thr Ala Ile Ala Gln Ile Val Pro Gly Leu Ile Pro Asp Gln Asn
                165                 170                 175

Thr Ala Thr Glu Ser Ala Gln Gly Leu Val Gln Leu Ala Thr Asn Ala
            180                 185                 190

Gln Val Leu Gln Gly Gln Ile Arg Glu Gly Phe Ala Ile Ser Pro Tyr
        195                 200                 205

Ala Phe Ala Asn Ala Arg Ala Asn Glu Asn Gln Ala Gly Thr Val Lys
    210                 215                 220

Ile Ala Ser Gln Ser Gln Met Asn Ala Gly Ser Asp Asp Thr Val Val
225                 230                 235                 240

Val Ser Ala Lys Lys Phe Ala Ser Thr Lys Ala Thr Thr Ser Gln Tyr
                245                 250                 255

Gly Ile Val Lys Leu Arg Asp Thr Val Gly Ser Glu Asn Ala Ala
            260                 265                 270

Leu Ser Ala Asn Ala Lys Val Leu Pro Ser Thr Gly Thr Val Ser
        275                 280                 285

Gly Asn Val Tyr Lys Gly Ser Asn Ser Asp Gly Asn Gln Phe Val Thr
    290                 295                 300

Lys Asn Glu Leu Ala Asn His Ala Met Pro Ile Gly Gly Ile Ile Leu
305                 310                 315                 320

Ser Gly Phe Asn Ala Asp Arg Gly Asp Phe Leu Ile Cys Asn Gly Arg
                325                 330                 335

Ser Leu Asn Lys Asn Gln Tyr Pro Gln Leu Phe Ser Ala Ile Gly Tyr
            340                 345                 350

Thr Phe Gly Gly Ser Gly Asp Asn Phe Asn Leu Pro Asp Met Arg Gly
        355                 360                 365

Leu Val Ala Arg Gly Cys Asp His Gly Arg Asn Leu Asp Pro Gly Arg
    370                 375                 380

Arg Phe Gly Ser Tyr Gln Glu Asp Ala Met Gln Arg Ile Thr Gly Lys
385                 390                 395                 400

Phe Pro Val Ala Asp Arg Trp Arg Gly Trp Tyr Gly Gly Ala Phe Thr
```

```
                         405                 410                 415
Ala Gln Arg Gly Gln Trp Ser Thr Asn Tyr Lys Asn Gly Gly Asp
            420                 425                 430

Asp Trp Gly Thr Thr Val Asn Phe Asp Ser Gly Arg Ser Val Ala Asn
            435                 440                 445

Glu Thr Arg Val Lys Ser Leu Ala Leu Asn Tyr Ile Ile Arg Val Arg
    450                 455                 460

<210> SEQ ID NO 30
<211> LENGTH: 466
<212> TYPE: PRT
<213> ORGANISM: N-Strep  44R2

<400> SEQUENCE: 30

Met Val Ala Asn Asn Ile Lys Asn His Ile Ser Asp Ser Ala Glu Ser
1               5                   10                  15

Val Asn Tyr Thr Gly Asp Asn Trp Pro Ala Ile Val Thr Thr Val Ala
            20                  25                  30

Asp Ala Leu Asp Arg Val Ala Pro Trp Ala Ile Ile Asp Asn Gly Leu
        35                  40                  45

Pro Leu Ala Thr Thr Gln Ile Ala Gly Ile Ile Arg Ile Ala Thr Thr
    50                  55                  60

Ala Glu Met Gln Ala Gly Thr Ser Ala Asn Thr Ala Ile Thr Pro Ala
65              70                  75                  80

Leu Leu Lys Leu Ala Met Glu Thr Pro Gln Ala Ser Glu Thr Ile Val
                85                  90                  95

Gly Asn Thr Arg Tyr Ala Thr Asn Ala Glu Ala Leu Ala Leu Thr Leu
            100                 105                 110

Asn Thr Ala Ala Ile Thr Pro Ala Asn Leu Gly Tyr Val Phe Ala Asn
        115                 120                 125

Lys Ala Ala Thr Glu Ser Ala Arg Gly Thr Met Arg Ile Ser Thr Gln
    130                 135                 140

Ala Gln Ala Thr Ser Gly Thr Asp Asp Ala Thr Thr Met Thr Pro Leu
145                 150                 155                 160

Lys Thr Lys Leu Ala Ile Gln Ala Leu Ser Gln Ala Trp Gly Thr Ala
                165                 170                 175

Thr Glu Ser Ala Arg Gly Val Val Gln Met Ala Thr Val Ala Gln Ala
            180                 185                 190

Leu Gln Gly Thr Leu Arg Asp Gly Phe Ala Ile Ser Pro Tyr Thr Leu
        195                 200                 205

Ser Lys Met Ala Gly Thr Glu Ser Ala Ala Gly Met Phe Lys Ile Ala
    210                 215                 220

Ser Asn Ser Gln Ile Leu Ala Leu Ala Asp Asn Thr Val Val Val Thr
225                 230                 235                 240

Pro Ala Lys Leu Asp Ile Leu Lys Ala Thr Ala Ser Gln Leu Gly Leu
                245                 250                 255

Val Lys Leu Ser Gly Val Ser Thr Ala Ala Asn Thr Ala Leu Ala
            260                 265                 270

Ala Ser Ala Pro Val Leu Tyr Thr Ser Gly Ile Ile Thr Gly Asp
        275                 280                 285

Val Thr Phe Thr Gly Asn Met Gln Gly Ile Gln Trp Ser Arg Asn Thr
    290                 295                 300

Asp Met Ala His Ile Val Phe Lys Asn Asp Ser Asn Ala Asp Ser Asn
305                 310                 315                 320

Ser Phe Met Gln Phe Cys Val Gly Asp Asp Asn Asn Glu Tyr Phe Arg
```

```
                    325                 330                 335
Trp Val Asn Arg Phe Ser Gly Ser Asp Asn Leu Met Ala Thr Leu Arg
                340                 345                 350

Pro Gly Gly His Met Trp Leu Ala Gly Asn Ile Asp Val Asn Asp Phe
            355                 360                 365

Tyr Ile Arg Ser Asp Arg Arg Leu Lys His Gly Phe Lys Pro Ile Glu
        370                 375                 380

Asn Ala Leu Asp Lys Ile Asp Leu Leu Asn Pro Gly Thr Tyr His Lys
385                 390                 395                 400

Gln Tyr Ser Leu Thr Asp Asp Arg Ile Val Gly Leu Glu Ala Gly Ile
                405                 410                 415

Phe Ala Gln Asp Phe Gln Lys Ala Met Pro Glu Gly Val Arg Ser Leu
            420                 425                 430

Glu Asp Gly Thr Leu Thr Val Ser Pro Met Gly Ala Ile Ala Phe Leu
        435                 440                 445

Ile Gln Cys Asn Lys Glu Leu Lys Ala Arg Leu Glu Lys Leu Glu Gly
    450                 455                 460

Ile Lys
465

<210> SEQ ID NO 31
<211> LENGTH: 466
<212> TYPE: PRT
<213> ORGANISM: N-Strep  PHG31p12

<400> SEQUENCE: 31

Met Val Ala Asn Asn Ile Lys Asn His Ile Ser Asp Ser Ala Glu Ser
1               5                   10                  15

Val Asn Tyr Thr Gly Asp Thr Trp Pro Ala Ile Val Thr Thr Val Ala
            20                  25                  30

Asp Ala Leu Asp Arg Val Ala Pro Trp Ala Ile Ile Asp Asn Gly Leu
        35                  40                  45

Pro Leu Ala Thr Thr Gln Ile Ala Gly Ile Ile Arg Ile Ala Thr Thr
    50                  55                  60

Ala Glu Met Gln Ala Gly Thr Ser Ala Asn Thr Ala Ile Thr Pro Ala
65                  70                  75                  80

Leu Leu Lys Leu Ala Met Glu Thr Pro Gln Ala Ser Glu Thr Ile Val
                85                  90                  95

Gly Asn Thr Arg Tyr Ala Thr Asn Ala Glu Leu Ala Leu Thr Leu
            100                 105                 110

Asn Thr Ala Ala Ile Thr Pro Ala Asn Leu Gly Tyr Val Phe Ala Asn
        115                 120                 125

Lys Ala Ala Thr Glu Ser Ala Arg Gly Thr Met Arg Ile Ser Thr Gln
    130                 135                 140

Ala Gln Ala Thr Ser Gly Thr Asp Asp Ala Thr Thr Met Thr Pro Leu
145                 150                 155                 160

Lys Thr Lys Leu Ala Ile Gln Ala Leu Ser Gln Ala Trp Gly Thr Ala
                165                 170                 175

Thr Glu Ser Ala Arg Gly Val Val Gln Met Ala Thr Val Ala Gln Ala
            180                 185                 190

Leu Gln Gly Thr Leu Arg Asp Gly Phe Ala Ile Ser Pro Tyr Thr Leu
        195                 200                 205

Ser Lys Met Ala Gly Thr Glu Ser Ala Ala Gly Met Phe Lys Ile Ala
    210                 215                 220

Ser Asn Ser Gln Ile Leu Ala Leu Ala Asp Asn Thr Val Val Thr
```

```
                225                 230                 235                 240
Pro Ala Lys Leu Asp Ile Leu Lys Ala Thr Ala Ser Gln Leu Gly Leu
                245                 250                 255

Val Lys Leu Ser Gly Val Ser Thr Ala Ala Asn Thr Ala Leu Ala
            260                 265                 270

Ala Ser Ala Pro Val Leu Tyr Thr Ser Gly Gly Ile Ile Thr Gly Asp
            275                 280                 285

Val Thr Phe Thr Gly Asn Met Gln Gly Ile Gln Trp Ser Arg Asn Thr
290                 295                 300

Asp Met Ala His Ile Val Phe Lys Asn Asp Ser Asn Ala Asp Ser Asn
305                 310                 315                 320

Ser Phe Met Gln Phe Cys Val Gly Asp Asp Asn Asn Glu Tyr Phe Arg
                325                 330                 335

Trp Val Asn Arg Phe Ser Gly Ser Asp Asn Ile Met Ala Thr Leu Arg
                340                 345                 350

Pro Gly Gly His Met Trp Leu Ala Gly Asn Ile Asp Val Asn Asp Phe
            355                 360                 365

Tyr Ile Arg Ser Asp Arg Arg Leu Lys His Gly Phe Lys Pro Ile Glu
370                 375                 380

Asn Ala Leu Asp Lys Ile Asp Leu Leu Asn Pro Gly Thr Tyr His Lys
385                 390                 395                 400

Gln Tyr Ser Leu Thr Asp Asp Arg Ile Val Gly Leu Glu Ala Gly Ile
                405                 410                 415

Phe Ala Gln Asp Phe Gln Lys Ala Met Pro Glu Gly Val Arg Ser Leu
            420                 425                 430

Glu Asp Gly Thr Leu Thr Val Ser Pro Met Gly Ala Ile Ala Phe Leu
            435                 440                 445

Ile Gln Cys Asn Lys Glu Leu Lys Ala Arg Leu Glu Lys Leu Glu Gly
            450                 455                 460

Ile Lys
465

<210> SEQ ID NO 32
<211> LENGTH: 473
<212> TYPE: PRT
<213> ORGANISM: N-Strep  KVP40p12

<400> SEQUENCE: 32

Met Ser Lys Gly Thr Gln Ile Phe Asn His Val Ile Asp Asp Ala Gly
1               5                   10                  15

Thr Val Thr Val Glu Val Ala Gly Thr Ala Phe Asp Gly Gln Thr Gly
            20                  25                  30

Gly Asn Asp Asp Leu Gln Thr Cys Leu Glu Leu Ile Gln Asp His Ala
        35                  40                  45

Val Gln Pro Leu Pro Asp Tyr Pro Val Ala Ser Thr Thr Val Ala Gly
50                  55                  60

Ile Thr Lys Leu Ser Asp Glu Ala Ala Val Val Asp Pro Leu Asn Thr
65                  70                  75                  80

Asp Ser Ala Val Thr Pro Ser Ser Leu Asp Tyr Trp Met Gln Asn His
                85                  90                  95

Ala Thr Ala Thr Glu Leu Gln Tyr Gly Phe Val Lys Leu Ile Thr Glu
            100                 105                 110

Ser Thr Ile Asp Thr Val Ala Pro Ser Asp Pro Val Glu Ala Ala Gln
        115                 120                 125

Lys His Ala Phe Thr Leu Lys Thr Leu Asn Tyr Ala Leu Asn Thr Arg
```

-continued

```
                130                 135                 140
Phe Tyr Ala Thr Glu Ser Asp Pro Gly Ala Val Arg Leu Ala Thr Asn
145                 150                 155                 160

Ala Gln Ala Thr Thr Thr Gly Thr Leu Ser Thr Thr Val Ala Met Thr
                165                 170                 175

Pro Gln Arg Val Lys Glu Met Leu Asp Val Trp Ala Asn Thr Thr Ala
                180                 185                 190

Ser Asp Ala Ser Glu Thr Thr Lys Gly Leu Ile Arg Leu Ala Asn Gly
                195                 200                 205

Thr Glu Val Asn Ser Thr Leu Ala Thr Glu Asp Asn Leu Ala Ile Ser
    210                 215                 220

Pro Tyr Arg Phe Asn Phe Arg Thr Ala Thr Thr Thr Arg Lys Ala Gly
225                 230                 235                 240

Phe Tyr Leu Pro Asp Ala Thr Val Ala Asn Ala Arg Ala Ser Asn Glu
                245                 250                 255

His Ala Val Thr Val Gly Thr Leu Asn Leu Phe Ser Ala Asn Ser Ser
                260                 265                 270

Arg Val Gly Val Ala Lys Ile Ala Asn Asn Leu Thr Thr Asn Asp Pro
                275                 280                 285

Leu Gln Ala Leu Ser Ala Ala Met Gly Tyr Lys Leu Asn Asn Glu Lys
    290                 295                 300

Ile Gly Asp Ala Gly Gly Thr Val Thr Gly Thr Leu Lys Ile Asn Asn
305                 310                 315                 320

Val Gln Ser Val Gly Gly Thr Gln Leu Met Thr Asn Gly Leu Ile Glu
                325                 330                 335

Ser Gln Ala Met Leu Asn Met Tyr Pro Val Gly Ser Val Tyr Met Ser
                340                 345                 350

Leu Val Ser Thr Ser Pro Ala Thr Leu Phe Gly Gly Thr Trp Ala Arg
    355                 360                 365

Leu Ala Gln Gly Arg Val Leu Val Ser Glu Gly Ser Tyr Gly Gly Arg
    370                 375                 380

Thr Phe Ala Val Arg Gln Thr Gly Gly Glu Tyr Glu Val Gln Leu Thr
385                 390                 395                 400

Glu Ala Thr Ile Pro Ala His Lys His Ala Gly Trp Gly Glu His Tyr
                405                 410                 415

Asp Gly Asn Gly Ile Gly Phe Gly Val Ala Lys Gln Tyr Gly Arg Asn
                420                 425                 430

Asn Pro Gly Ser Arg Arg Thr Asp Ser Asp Asn Tyr Leu Tyr Tyr Thr
    435                 440                 445

Ser Pro Val Gly Gly Asn Gln Ala His Asn Asn Val Gln Pro Tyr Tyr
450                 455                 460

Thr Val Tyr Met Trp Glu Arg Thr Ala
465                 470
```